(12) United States Patent
Quattropani et al.

(10) Patent No.: US 7,799,814 B2
(45) Date of Patent: Sep. 21, 2010

(54) THIAZOLE DERIVATIVES AND USE THEREOF

(75) Inventors: Anna Quattropani, Geneva (CH); Jerome Dorbais, Annecy (FR); David Covini, Neydens (FR); Gwenaelle Desforges, Annemasse (FR); Thomas Rueckle, Geneva (CH)

(73) Assignee: Merck Serono S.A., Coinsins, Vaud (CH)

( * ) Notice: Subject to any disclaimer, the term of this patent is extended or adjusted under 35 U.S.C. 154(b) by 147 days.

(21) Appl. No.: 11/915,476

(22) PCT Filed: May 24, 2006

(86) PCT No.: PCT/EP2006/062595

§ 371 (c)(1),
(2), (4) Date: Nov. 26, 2007

(87) PCT Pub. No.: WO2006/125805

PCT Pub. Date: Nov. 30, 2006

(65) Prior Publication Data

US 2008/0188531 A1    Aug. 7, 2008

Related U.S. Application Data

(60) Provisional application No. 60/686,270, filed on Jun. 1, 2005.

(30) Foreign Application Priority Data

May 24, 2005    (EP) .................................. 05104394

(51) Int. Cl.
*A61K 31/425*    (2006.01)
*C07D 277/00*    (2006.01)

(52) U.S. Cl. ...................................... 514/370; 548/190
(58) Field of Classification Search .................. 514/370; 548/190
See application file for complete search history.

(56) References Cited

U.S. PATENT DOCUMENTS

| 7,163,952 | B2 * | 1/2007 | Inaba et al. ................. 514/370 |
| 2003/0158199 | A1 * | 8/2003 | Stieber et al. ............... 514/242 |
| 2008/0200463 | A1 | 8/2008 | Quattropani et al. |
| 2008/0221180 | A1 | 9/2008 | Quattropani et al. |

FOREIGN PATENT DOCUMENTS

| EP | 0 117 082 | 8/1984 |
| WO | WO 00/75120 | 12/2000 |
| WO | WO 03/072557 | 9/2003 |
| WO | WO 2004/078754 | 9/2004 |
| WO | WO 2004/096797 | 11/2004 |
| WO | WO 2005/021519 | 3/2005 |

OTHER PUBLICATIONS

Inaba et al., 2002, CAS:136:177998.*
Sawhney, S. N. et al. "Thiazole Derivatives: Part I—Synthesis & Anti-Inflammatory Activity of some 2'-Alkyl/Aryl-2-Aryl-4-Methyl-4'5-Bithiazolyls & 2'Amino/Substituted Amino-2-Aryl-4-Methyl-4'5-Bithiazolyls" *Indian Journal of Chemistry*, Jul. 1976, pp. 552-555, vol. 14B, No. 7.
Cantley, L. C. "The Phosphoinositide 3-Kinase Pathway" *Science*, May 31, 2002, pp. 1655-1657, vol. 296.
Fraser, J.D. et al. "Regulation of Interleukin-2 Gene Enhancer Activity by the T Cell Accessory Molecule CD28" *Science*, Jan. 18, 1991, pp. 313-316, vol. 251.
Fruman, D.A. et al. "Phosphoinositide Kinases" *Annu. Rev. Biochem.*, 1998, pp. 481-507, vol. 67.
Gerard, C. et al. "Chemokines and disease" *Nature Immunology*, Feb. 2001, pp. 108-115, vol. 2, No. 2, Nature Publishing Group.
Grant, S. "Targeted Therapies in Cancer—Second International Congress" *Current Drugs*, 2003, pp. 946-948, vol. 6, No. 10.
Guarna, A. et al. "Synthesis and Reactivity of Bicycles Derived from Tartaric Acid and α-Amino Acids: A Novel Class of Conformationally Constrained Dipeptide Isosteres Based upon Enantiopure 3-Aza-6, 8-dioxabicyclo [3.2.1] octane-7-carboxylic Acid" *J. Org. Chem.*, 1999, pp. 7347-7364, vol. 64.
Herr, R. J. et al. "A Convenient Method for the Preparation of Primary and Symmetrical N,N'-Disubstituted Thioureas" *Synthesis*, 2000, pp. 1569-1574, No. 11.
Hirsch, E. et al. "Central Role for G Protein-Coupled Phosphoinositide 3-Kinase γ in Inflammation" *Science*, Feb. 11, 2000, pp. 1049-1053, vol. 287.
Hirsch, E. et al. "Resistance to thromboembolism in PI3 Kγ-deficient mice" *FASEB J.*, Jul. 9, 2001, pp. 2019-2021, vol. 15, No. 11.
Kodomari, M. et al. "One-pot synthesis of 2-aminothiazoles using supported reagents" *Tetrahedron Letters*, 2002, pp. 1717-1720, vol. 43.
Laffargue, M. et al. "Phosphoinositide 3-Kinase γ Is an Essential Amplifier of Mast Cell Function" *Immunity*, Mar. 2002, pp. 441-451, vol. 16.
Lawlor, M.A. et al. "PKB/Akt: a key mediator of cell proliferation, survival and insulin responses?" *Journal of Cell Science*, 2001, pp. 2903-2910, vol. 114.
Parker, P. J. "PI 3-kinase puts GTP on the Rac" *Current Biology*, 1995, pp. 577-599, vol. 5, No. 6.
Pirrung, M.C. et al. "Trityl Isothiocyanate Support for Solid-Phase Synthesis" *J. Comb. Chem.*, 2001, pp. 90-96, vol. 3.

(Continued)

*Primary Examiner*—Rei-tsang Shiao
(74) *Attorney, Agent, or Firm*—Saliwanchik, Lloyd & Saliwanchik

(57) ABSTRACT

The present invention is related to thiazole derivatives of Formula (I) in particular for the treatment and/or prophylaxis of autoimmune disorders and/or inflammatory diseases, cardiovascular diseases, neurodegenerative diseases, bacterial or viral infections, kidney diseases, platelet aggregation, cancer, transplantation, graft rejection or lung injuries.

28 Claims, No Drawings

OTHER PUBLICATIONS

Sayed, S.M. et al. "Synthesis and Reactivity of Cyanomethyl 2-Amino-4-methylthiazolyl Ketone. A Facile Synthesis of Novel Pyrazolo [5,1-c] 1,2,4-triazine, 1,2,4-Triazolo [5,1-c] 1, 2,4,-triazine, 1,2,4-Triazino [4,3-a] benzimidazole, Pyridazine-6-imine and 6-Oxopyridazinone Derivatives" *Heteroatom Chemistry*, 1999, pp. 385-390, vol. 10, No. 5.

Stein, R.C. et al. "PI3-kinase inhibition: a target for drug development?" *Molecular Medicine Today*, Sep. 2000, pp. 347-357, vol. 6.

Thelen, M. et al. "Wortmannin binds specifically to 1-phosphatidylinositol 3-kinase while inhibiting guanine nucleotide-binding protein-coupled receptor signaling in neutrophil leukocytes" *Proc. Natl. Acad. Sci. USA*, May 1994, pp. 4960-4964, vol. 91.

Toker, A. "Phosphoinositides and signal transduction" *Cellular and Molecular Life Sciences*, 2002, pp. 761-779, vol. 59.

Vanhaesebroeck, B. et al. "Phosphoinositide 3-kinases: a conserved family of signal transducers" *Trends Biochem. Sci.*, Jul. 1997, pp. 267-272, vol. 22, No. 7.

Vanhaesebroeck, B. et al. "Synthesis and Function of 3-Phosphorylated Inositol Lipids" *Ann. Rev. Biochem*, 2001, pp. 535-602, vol. 70.

Wilson, K.J. et al. "Synthesis of Thiophene-2-carboxamidines Containing 2-Amino-thiazoles and their Biological Evaluation as Urokinase Inhibitors" *Bioorganic & Medicinal Chemistry Letters*, 2001, pp. 915-918, vol. 11.

Wittenberger, S.J. et al. "Dialkyltin Oxide Mediated Addition of Trimethylsilyl Azide to Nitriles. A Novel Preparation of 5-Substituted Tetrazoles" *J.Org. Chem*.1993, pp. 4139-4141, vol. 58.

Wymann, M.P. et al. "Lipids on the move: phosphoinositide 3-kinases in leukocyte function" *Immunology Today*, Jun. 2000, pp. 260-264, vol. 21, No. 6.

* cited by examiner

THIAZOLE DERIVATIVES AND USE THEREOF

CROSS-REFERENCE TO RELATED APPLICATION

This application is the U.S. national stage application of International Patent Application No. PCT/EP2006/062595, filed May 24, 2006, which claims the benefit of U.S. Provisional Patent Application No. 60/686,270, filed Jun. 1, 2005, the disclosures of which are hereby incorporated by reference in their entireties, including all figures, tables and amino acid or nucleic acid sequences.

FIELD OF THE INVENTION

This present invention is related to the use of thiazole derivatives of Formula (I) for the treatment and/or prophylaxis of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries. Specifically, the present invention is related to thiazole derivatives for the modulation, notably the inhibition of the activity or function of the phosphoinositide-3-kinases, PI3Ks.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657 and Vanhaesebroeck et al., 2001, *Annu. Rev. Biochem.*, 70, 535-602).

The term PI3K is given to a family of lipid kinases which, in mammals, consists of eight identified PI3Ks that are divided into three sub-families according to their structure and their substrate specificity.

Class I group of PI3Ks consists of two sub-groups, Class IA and Class IB.

Class IA consists of an 85 kDa regulatory unit (responsible for protein-protein interactions via the interaction of Src homology 2 (SH2) domain with phosphotyrosine residues of other proteins) and a catalytic sub-unit of 110 kDa. Three catalytic forms (p110α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic subunit complexed with a 101-kDa regulatory protein, p101).

Class II PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the hematopoietic cell system, smooth muscle cells, myocytes and endothelial cells (Vanhaesebraeck et al., 1997, *Trends Biochem Sci.*, 22(7), 267-72). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)$P_2$), respectively generating three lipid products, namely phosphatidylinositol 3-monophosphate (PI(3)P), phosphatidylinositol 3,4-bisphosphate (PI(3,4)$P_2$) and phosphatidylinositol 3,4,5-trisphosphate (PI(3,4,5)$P_3$ (see Scheme A below).

Scheme A

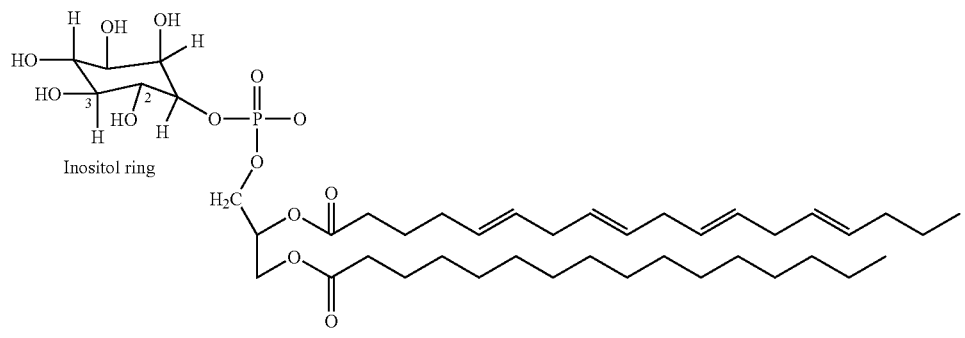

PtdIns (Phosphatidylinositol)

↓ PI3K

-continued

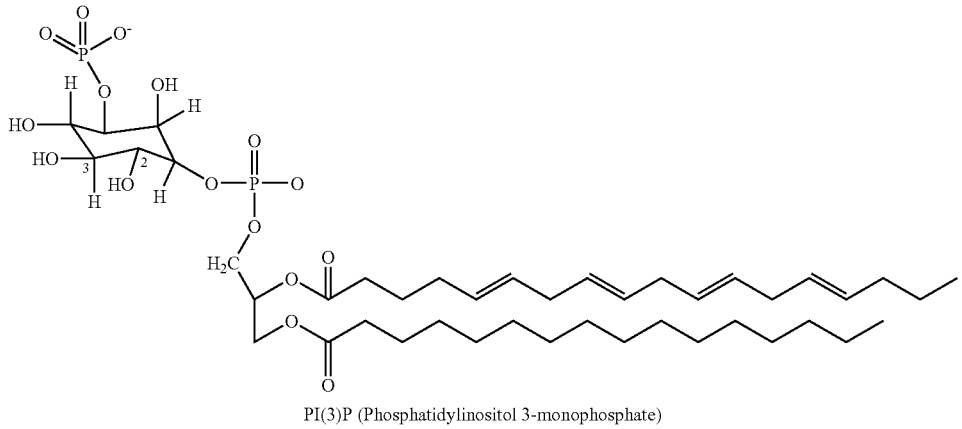

PI(3)P (Phosphatidylinositol 3-monophosphate)

The preferred substrate for Class I PI3Ks is PI(4,5)P$_2$. Class II PIKs have a strong preference for PtdIns as substrate over PI(4)P and PI(4,5)P$_2$. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimerization, transactivation by heterologous receptor (e.g. receptor tyrosine kinase) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, Cell Mol. Life. Sci. 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, Mol. Med. Today 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, Immunol Today 21(6) 260-4; Hirsch et al., 2000, Science 287(5455) 1049-53; Hirsch et al., 2001, FASEB J. 15(11) 2019-21 and Gerard et al., 2001, Nat. Immunol. 2(2) 108-15).

PI3-kinase activation, is therefore believed to be involved in a range of cellular responses including cell growth, differentiation and apoptosis (Parker et al., 1995, Current Biology, 5, 577-99).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen. These effects are linked to increases in the transcription of a number of genes including interleukin-2 (IL-2), an important T cell growth factor (Fraser et al., 1991, Science, 251, 313-16). Mutation of CD28 such that it can longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3Kγ has been identified as a mediator of G beta-gamma-dependent regulation of JNK activity wherein G beta-gamma are subunits of heterotrimeric G proteins.

Recently, it has been described that PI3Kγ relays inflammatory signals through various G(i)-coupled receptors (Laffargue et al., 2002, Immunity 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, J. Cell. Sci., 114 (Pt 16) 2903-1).

Specific inhibitors against individual members of a family of enzymes provide valuable tools for deciphering functions of each enzyme.

Two compounds, LY294002 and wortmannin (cf.hereinafter), have been widely used as PI3-kinase inhibitors. These compounds are non-specific PI3K inhibitors, as they do not distinguish among the four members of Class I PI3-kinases.

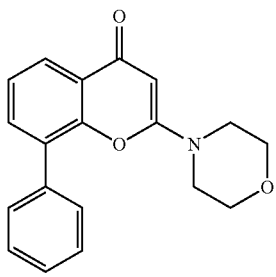

LY 294002

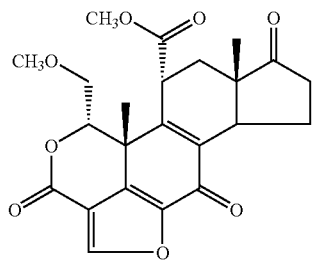

Wortmannin $IC_{50}$ values of wortmannin against each of the various Class I PI3-kinases are in the range of 1-10 mM and $IC_{50}$ values for LY294002 against each of these PI3-kinases are about 15-µM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using wortmannin, there is evidence that PI3-kinase function is also required for some aspects of leukocyte signaling through G-protein coupled receptors (Thelen et al., 1994). Moreover, it has been shown that wortmannin and LY294002 block neutrophil migration and superoxide release. However, inasmuch as these compounds do not distinguish among the various isoforms of PI3K, it remains unclear which particular PI3K isoform or isoforms are involved in these phenomena.

Some results have indicated that PI3K inhibitors, for example, LY294002, can increase the in vivo antitumor activity of certain cytotoxic agents (e.g. paclitaxel) (Grant, 2003, *Current Drugs*, 6(10), 946-948).

Recently, thiazole derivatives have been recently developed as PI3K inhibitors (WO 2005/021519; WO 04/078754 and WO 04/096797).

WO 2005/021519 discloses thiazole derivatives of the following structure:

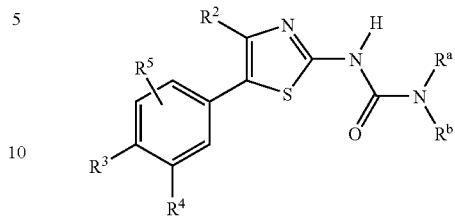

WO 04/078754 discloses thiazole derivatives of the following structure:

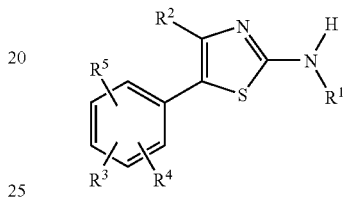

WO 04/096797 discloses thiazole derivatives of the following structure:

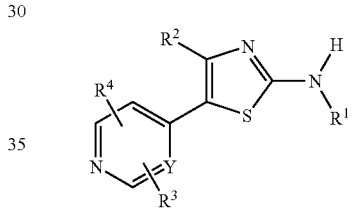

The high relevance of the PI3K pathway in some widely spread diseases stresses the need to develop inhibitors, including selective inhibitors, of PIKs.

SUMMARY OF THE INVENTION

One embodiment of the present invention provides substances which are suitable for the treatment and/or prevention of disorders related to phosphoinositide-3-kinases, PI3Ks.

Another embodiment of the present invention provides substances which are suitable for the treatment and/or prevention of auto-immune and/or inflammatory disorders.

Another embodiment of the present invention provides substances which are suitable for the treatment and/or prevention of cardiovascular diseases.

Another embodiment of the present invention provides substances which are suitable for the treatment and/or prevention of neurodegenerative disorders.

Another embodiment of the present invention provides substances which are suitable for the treatment and/or prevention of a disorder selected from bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

Another embodiment of the present invention provides chemical compounds which are able to modulate, especially inhibit the activity or function of phosphoinositide-3-kinases, PI3Ks in disease states in mammals, especially in humans.

Another embodiment of the present invention provides a new category of pharmaceutical formulations for the treatment of and/or diseases selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

Another embodiment of the present invention provides a method for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

In one embodiment, the invention provides thiazole derivatives of Formula (I):

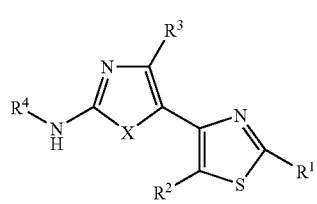

(I)

wherein $R^1$, $R^2$, $R^3$, $R^4$ and X are defined in the detailed description below.

In another embodiment, the invention provides a compound according to Formula (I) for use as a medicament.

In another embodiment, the invention provides a use of a compound according to Formula (I) for the preparation of a pharmaceutical composition for the treatment of a disorder selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions and other diseases and disorders associated with the phosphoinositide-3-kinases, PI3Ks, comprising PI3K α and γ.

In another embodiment, the invention provides a pharmaceutical composition comprising at least one a compound according to Formula (I) and a pharmaceutically acceptable carrier, diluent or excipient thereof.

In another embodiment, the invention provides a method for treating a patient suffering from a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks. The method comprises administering a compound according to Formula (I).

In another embodiment, the invention provides a method of synthesis of a compound according to Formula (I).

In another embodiment, the invention provides compounds according to Formula (Ia).

In another embodiment, the invention provides compounds according to Formula (P3).

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenylpropanoyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH═CH$_2$), n-2-propenyl (allyl, —CH$_2$CH═CH$_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having a carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "heteroaryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having a $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethylacetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$RR'R", where each R, R', R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Substituted" refers to groups substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfanyl", "halogen", trihalomethyl, cyano, hydroxy, mercapto, nitro, and the like "Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R', R''$^+$Z$^-$, wherein R, R', R'' is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism.

It has now been found that compounds of the present invention are modulators of the Phosphatoinositides 3-kinases (PI3Ks), comprising PI3K α and γ. When the phosphatoinositides 3-kinase (PI3K) enzyme is inhibited by the compounds of the present invention, PI3K is unable to exert its enzymatic, biological and/or pharmacological effects.

The compounds of the present invention are therefore useful in the treatment and prevention of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and paratoluenesulfonate salts.

The compounds according to Formula (I) are suitable for the modulation, notably the inhibition of the activity of phosphatoinositides 3-kinases (PI3K). It is therefore believed that the compounds of the present invention are also particularly useful for the treatment and/or prevention of disorders, which are mediated by PI3Ks, particularly PI3K α and/or PI3K γ. Said treatment involves the modulation—notably the inhibition or the down regulation—of the phosphatoinositides 3-kinases.

The compounds according to Formula (I) are suitable for use as a medicament.

One embodiment of the present invention provides thiazole derivatives of Formula (I):

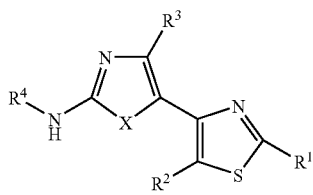

wherein $R^1$ is selected from —$C(O)R^5$; optionally substituted $C_1$-$C_6$-alkyl, including cyanomethyl, hydroxymethyl; optionally substituted $C_2$-$C_6$-alkenyl; optionally substituted $C_2$-$C_6$-alkynyl; optionally substituted aryl $C_1$-$C_6$-alkyl; optionally substituted heteroaryl $C_1$-$C_6$-alkyl, including tetrazolyl methyl (e.g. 2H-tetrazol-5yl-methyl); optionally substituted $C_3$-$C_8$ cycloalkyl $C_1$-$C_6$-alkyl and optionally substituted heterocycloalkyl $C_1$-$C_6$-alkyl;

$R^2$ is selected from H; halogen; optionally substituted $C_1$-$C_6$-alkyl; optionally substituted $C_2$-$C_6$-alkenyl and optionally substituted $C_2$-$C_6$-alkynyl;

$R^3$ is selected from H; halogen; optionally substituted $C_1$-$C_6$-alkyl, including methyl; optionally substituted $C_2$-$C_6$-alkenyl and optionally substituted $C_2$-$C_6$-alkynyl;

$R^4$ is selected from —$C(O)R^6$; optionally substituted aryl, including; optionally substituted heteroaryl, including pyrazinyl (e.g. pyrazin-2-yl) and pyrazolyl (e.g. pyrazol-3-yl);

optionally substituted heterocycloalkyl and optionally substituted $C_3$-$C_8$ cycloalkyl;

$R^5$ is selected from H; hydroxy; optionally substituted alkoxy, including ethoxy; optionally substituted amino, including allylamine, methoxyethylamine (e.g. 2-methoxyethylamine), methoxy propyl amine (e.g. 3-methoxy-propylamine), hydroxy ethyl amine (e.g. 2-hydroxyethylamine), hydroxylpropyl amine (e.g. 2,3-dihydroxypropyl amine), cyano ethyl amine (e.g. 2-cyanoethylamine), propylamine (e.g. n-propylamine), prop-2-ynylamine, tetrahydrofuran methylamine (e.g. tetrahydrofuran-2-yl-methylamine), dimethyl amino ethyl amine (e.g. 2-(dimethylamino)ethyl amine), dimethyl amino propyl amine (e.g. 3-(dimethylamino)propyl amine), tetrazolyl amine (e.g. 1H-tetrazol-5-yl amine, 1H-tetrazol-3-yl amine), amino-benzoic acid (e.g. 4-amino-benzoic acid, 3-amino-benzoic acid, 3-amino-2-hydroxy-benzoic acid, 4-amino-2-hydroxy-benzoic acid, 4-amino-2-fluorobenzoic acid, 5-amino-2-hydroxy-benzoic acid), tetrazolyl phenyl amine (e.g. 3-(1H-tetrazol-5-yl)phenyl amine, 3-(1H-tetrazol-3-yl) phenyl amine, 4-(1H-tetrazol-5-yl)phenyl amine, 4-(1H-tetrazol-3-yl)phenyl amine), thiadiazolyl phenyl amine (e.g. 3-(5-amino-1,3,4-thiadiazol-2-yl)phenyl amine), oxadiazolyl phenyl amine (e.g. 3-(5-hydroxy-1,3,4-oxadiazol-2-yl)phenyl amine, 4-(5-hydroxy-1,3,4-oxadiazol-2-yl)phenyl amine), benzyl amine (e.g. N-benzyl amine), 1H-1,2,3, benzotriazol-5-yl amine;

optionally substituted aryl; optionally substituted heteroaryl; optionally substituted $C_3$-$C_8$ cycloalkyl;

optionally substituted heterocycloalkyl, including morpholinyl (e.g. morpholin-4-yl), piperazinyl (e.g. 4-methylpiperazin-1-yl, 4-acetylpiperazin-1-yl, 3-oxopiperazin-1-yl, piperidinyl (e.g. 3-carboxylic acid piperidin-1-yl, 4-carboxylic acid piperidin-1-yl, 4-(hydroxylmethyl)piperidin-1-yl, 3-hydroxypiperidin-1-yl, 4-hydroxypiperidin-1-yl, 4-(2-hydroxyethyl)piperidin-1-yl, 4-fluoropiperidin-1-yl, 4-oxopiperidin-1-yl), 1,4-dioaxa-8-azaspiro[4.5]decan-8-yl, 7-(hydroxymethyl)-6,8-dioxa-3-azabicyclo[3.2.1]oct-3-yl, pyrrolidinyl (e.g. 3-hydroxypyrrolidin-1-yl);

$R^6$ selected from H; optionally substituted $C_1$-$C_6$-alkyl, including methyl; optionally substituted $C_2$-$C_6$-alkenyl; optionally substituted $C_2$-$C_6$-alkynyl; optionally substituted aryl $C_1$-$C_6$-alkyl; optionally substituted heteroaryl $C_1$-$C_6$-alkyl and optionally substituted amino, including optionally substituted $C_1$-$C_6$ alkyl amine such as methoxyethylamine (e.g. 2-methoxy-ethylamine), 2-amino-N,N-dimethyl-acetamide, 3-amino-propionic acid and 3-amino-propionic acid alkyl ester (e.g. 3-amino-propionic acid ethyl ester, 3-amino-propionic acid t-butyl ester);

X is selected from S and O; as well as its geometrical isomers, its optically active forms as enantiomers, diastereomers and its racemate forms, as well as pharmaceutically acceptable salts thereof.

Another embodiment of the present invention provides thiazole derivatives of Formula (I) wherein $R^1$ is —$C(O)R^5$.

Another embodiment of the present invention provides thiazole derivatives of Formula (I) wherein $R^1$ is selected from optionally substituted $C_1$-$C_6$-alkyl; optionally substituted $C_2$-$C_6$-alkenyl; optionally substituted $C_2$-$C_6$-alkynyl; optionally substituted aryl $C_1$-$C_6$-alkyl; optionally substituted heteroaryl $C_1$-$C_6$-alkyl; optionally substituted $C_3$-$C_8$ cycloalkyl $C_1$-$C_6$-alkyl and optionally substituted heterocycloalkyl $C_1$-$C_6$-alkyl;

Another embodiment of the present invention provides thiazole derivatives of Formula (I) wherein $R^2$ is H.

Another embodiment of the present invention provides thiazole derivatives of Formula (I) wherein $R^3$ is methyl.

Another embodiment of the present invention provides thiazole derivatives of Formula (I) wherein $R^4$ is selected from optionally substituted aryl, including; optionally substituted heteroaryl, including pyrazinyl (e.g. pyrazin-2-yl) and pyrazolyl (e.g. pyrazol-3-yl); optionally substituted heterocycloalkyl and optionally substituted $C_3$-$C_8$ cycloalkyl.

Another embodiment of the present invention provides thiazole derivatives of Formula (I) wherein $R^4$ is selected from —$C(O)R^6$.

Another embodiment of the present invention provides thiazole derivatives of Formula (I) wherein $R^5$ is selected from hydroxyl and optionally substituted alkoxy.

Another embodiment of the present invention provides thiazole derivatives of Formula (I) wherein $R^5$ is optionally substituted amino.

Another embodiment of the present invention provides thiazole derivatives of Formula (I) wherein $R^5$ is selected from optionally substituted aryl; optionally substituted heteroaryl; optionally substituted $C_3$-$C_8$ cycloalkyl and optionally substituted heterocycloalkyl.

Another embodiment of the present invention provides thiazole derivatives of Formula (I) wherein $R^6$ is selected from optionally substituted $C_1$-$C_6$-alkyl, optionally substituted $C_2$-$C_6$-alkenyl, optionally substituted $C_2$-$C_6$-alkynyl, optionally substituted aryl $C_1$-$C_6$-alkyl and optionally substituted heteroaryl $C_1$-$C_6$-alkyl.

Another embodiment of the present invention provides thiazole derivatives of Formula (I) wherein $R^6$ is optionally substituted amino.

Another embodiment of the present invention provides thiazole derivatives of Formula (I) wherein X is S.

Compounds of the present invention include in particular those of the group consisting of:

| Example N° | Name |
|---|---|
| 1 | Ethyl 2'-(acetylamino)-4'-methyl-4,5'-bi-1,3-thiazole-2-carboxylate; |
| 2 | 2'-(acetylamino)-N-allyl-4'-methyl-4,5'-bi-1,3-thiazole-2-carboxamide; |
| 3 | N-[2-(cyanomethyl)-4'-methyl-4,5'-bi-1,3-thiazol-2'-yl]acetamide; |
| 4 | 2'-(acetylamino)-4'-methyl-4,5'-bi-1,3-thiazole-2-carboxylic acid; |
| 5 | 2'-(acetylamino)-N-(2-methoxyethyl)-4'-methyl-4,5'-bi-1,3-thiazole-2-carboxamide; |
| 6 | 2'-(acetylamino)-4'-methyl-N-(tetrahydrofuran-2-ylmethyl)-4,5'-bi-1,3-thiazole-2-carboxamide; |
| 7 | 2'-(acetylamino)-N-[2-(dimethylamino)ethyl]-4'-methyl-4,5'-bi-1,3-thiazole-2-carboxamide; |
| 8 | N-[4'-methyl-2-(morpholin-4-ylcarbonyl)-4,5'-bi-1,3-thiazol-2'-yl]acetamide; |
| 9 | N-{4'-methyl-2-[(4-methylpiperazin-1-yl)carbonyl]-4,5'-bi-1,3-thiazol-2'-yl}acetamide; |
| 10 | 2'-(acetylamino)-N-[3-(dimethylamino)propyl]-4'-methyl-4,5'-bi-1,3-thiazole-2-carboxamide; |
| 11 | 2'-(acetylamino)-N-(2-hydroxyethyl)-4'-methyl-4,5'-bi-1,3-thiazole-2-carboxamide; |
| 12 | 2'-(acetylamino)-N-(2-cyanoethyl)-4'-methyl-4,5'-bi-1,3-thiazole-2-carboxamide; |
| 13 | 2'-(acetylamino)-4'-methyl-N-1H-tetrazol-5-yl-4,5'-bi-1,3-thiazole-2-carboxamide; |
| 14 | 4-({[2'-(acetylamino)-4'-methyl-4,5'-bi-1,3-thiazol-2-yl]carbonyl}amino)benzoic acid; |
| 15 | 3-({[2'-(acetylamino)-4'-methyl-4,5'-bi-1,3-thiazol-2-yl]carbonyl}amino)benzoic acid; |
| 16 | 2'-(acetylamino)-4'-methyl-N-[3-(1H-tetrazol-5-yl)phenyl]-4,5'-bi-1,3-thiazole-2-carboxamide; |
| 17 | 2'-(acetylamino)-N-benzyl-4'-methyl-4,5'-bi-1,3-thiazole-2-carboxamide; |
| 18 | 2'-(acetylamino)-4'-methyl-N-propyl-4,5'-bi-1,3-thiazole-2-carboxamide; |
| 19 | 2'-(acetylamino)-4'-methyl-N-[4-(1H-tetrazol-5-yl)phenyl]-4,5'-bi-1,3-thiazole-2-carboxamide; |
| 20 | 3-({[2'-(acetylamino)-4'-methyl-4,5'-bi-1,3-thiazol-2-yl]carbonyl}amino)-2-hydroxybenzoic acid; |
| 21 | 1-{[2'-(acetylamino)-4'-methyl-4,5'-bi-1,3-thiazol-2-yl]carbonyl}piperidine-3-carboxylic acid; |
| 22 | 5-({[2'-(acetylamino)-4'-methyl-4,5'-bi-1,3-thiazol-2-yl]carbonyl}amino)-2-hydroxybenzoic acid; |
| 23 | N-[4'-methyl-2-(2H-tetrazol-5-ylmethyl)-4,5'-bi-1,3-thiazol-2'-yl]acetamide; |
| 24 | 1-{[2'-(acetylamino)-4'-methyl-4,5'-bi-1,3-thiazol-2-yl]carbonyl}piperidine-4-carboxylic acid; |
| 25 | 2'-(acetylamino)-N-[3-(5-amino-1,3,4-thiadiazol-2-yl)phenyl]-4'-methyl-4,5'-bi-1,3-thiazole-2-carboxamide; |
| 26 | N-{2-[(3-hydroxypiperidin-1-yl)carbonyl]-4'-methyl-4,5'-bi-1,3-thiazol-2'-yl}acetamide; |
| 27 | N-(2-{[4-(hydroxymethyl)piperidin-1-yl]carbonyl}-4'-methyl-4,5'-bi-1,3-thiazol-2'-yl)acetamide; |
| 28 | N-(2-{[4-(2-hydroxyethyl)piperidin-1-yl]carbonyl}-4'-methyl-4,5'-bi-1,3-thiazol-2'-yl)acetamide; |
| 29 | N-{2-[(4-hydroxypiperidin-1-yl)carbonyl]-4'-methyl-4,5'-bi-1,3-thiazol-2'-yl}acetamide; |
| 30 | 2'-(acetylamino)-N-1H-1,2,3-benzotriazol-5-yl-4'-methyl-4,5'-bi-1,3-thiazole-2-carboxamide; |
| 31 | 4-({[2'-(acetylamino)-4'-methyl-4,5'-bi-1,3-thiazol-2-yl]carbonyl}amino)-2-hydroxybenzoic acid; |
| 32 | 4-({[2'-(acetylamino)-4'-methyl-4,5'-bi-1,3-thiazol-2-yl]carbonyl}amino)-2-fluorobenzoic acid; |
| 33 | 2'-(acetylamino)-N-[3-(5-hydroxy-1,3,4-oxadiazol-2-yl)phenyl]-4'-methyl-4,5'-bi-1,3-thiazole-2-carboxamide; |
| 34 | 2'-(acetylamino)-N-[4-(5-hydroxy-1,3,4-oxadiazol-2-yl)phenyl]-4'-methyl-4,5'-bi-1,3-thiazole-2-carboxamide; |

-continued

| Example Nº | Name |
|---|---|
| 35 | N-[2-(hydroxymethyl)-4'-methyl-4,5'-bi-1,3-thiazol-2'-yl]acetamide; |
| 36 | N-(2-methoxyethyl)-N'-[4'-methyl-2-(morpholin-4-ylcarbonyl)-4,5'-bi-1,3-thiazol-2'-yl]urea; |
| 37 | Ethyl N-({[4'-methyl-2-(morpholin-4-ylcarbonyl)-4,5'-bi-1,3-thiazol-2'-yl]amino}carbonyl)-beta-alaninate; |
| 38 | N-[2-(1,4-dioxa-8-azaspiro[4.5]dec-8-ylcarbonyl)-4'-methyl-4,5'-bi-1,3-thiazol-2'-yl]acetamide; |
| 39 | 2'-(acetylamino)-N-(2,3-dihydroxypropyl)-4'-methyl-4,5'-bi-1,3-thiazole-2-carboxamide; |
| 40 | N-[4'-methyl-2-(morpholin-4-ylcarbonyl)-4,5'-bi-1,3-thiazol-2'-yl]urea; |
| 41 | N-{4'-methyl-2-[(3-oxopiperazin-1-yl)carbonyl]-4,5'-bi-1,3-thiazol-2'-yl}acetamide; |
| 42 | N-{4'-methyl-2-[(4-oxopiperidin-1-yl)carbonyl]-4,5'-bi-1,3-thiazol-2'-yl}acetamide; |
| 43 | N-{2-[(3-hydroxypyrrolidin-1-yl)carbonyl]-4'-methyl-4,5'-bi-1,3-thiazol-2'-yl}acetamide; |
| 44 | 2'-(acetylamino)-4'-methyl-N-prop-2-yn-1-yl-4,5'-bi-1,3-thiazole-2-carboxamide; |
| 45 | N-{2-[(4-acetylpiperazin-1-yl)carbonyl]-4'-methyl-4,5'-bi-1,3-thiazol-2'-yl}acetamide; |
| 46 | N~1~,N~1~-dimethyl-N~2~-({[4'-methyl-2-(morpholin-4-ylcarbonyl)-4,5'-bi-1,3-thiazol-2'-yl]amino}carbonyl)glycinamide; |
| 47 | N-({[4'-methyl-2-(morpholin-4-ylcarbonyl)-4,5'-bi-1,3-thiazol-2'-yl]amino}carbonyl)-beta-alanine; |
| 48 | N-{2-[(4-fluoropiperidin-1-yl)carbonyl]-4'-methyl-4,5'-bi-1,3-thiazol-2'-yl}acetamide; |
| 49 | N-(2-{[(1S,5S,7S)-7-(hydroxymethyl)-6,8-dioxa-3-azabicyclo[3.2.1]oct-3-yl]carbonyl}-4'-methyl-4,5'-bi-1,3-thiazol-2'-yl)acetamide; |
| 50 | ethyl N-({[2-(cyanomethyl)-4'-methyl-4,5'-bi-1,3-thiazol-2'-yl]amino}carbonyl)-beta-alaninate; |
| 51 | N-(2-{[(1R,5R,7R)-7-(hydroxymethyl)-6,8-dioxa-3-azabicyclo[3.2.1]oct-3-yl]carbonyl}-4'-methyl-4,5'-bi-1,3-thiazol-2'-yl)acetamide; |
| 52 | Tert-butyl N-({[2-(cyanomethyl)-4'-methyl-4,5'-bi-1,3-thiazol-2'-yl]amino}carbonyl)-beta-alaninate; |
| 53 | [4'-methyl-2'-(pyrazin-2-ylamino)-4,5'-bi-1,3-thiazol-2-yl]acetonitrile; |
| 54 | Ethyl 4'-methyl-2'-(pyrazin-2-ylamino)-4,5'-bi-1,3-thiazole-2-carboxylate; |
| 55 | [4'-methyl-2'-(1H-pyrazol-3-ylamino)-4,5'-bi-1,3-thiazol-2-yl]acetonitrile; |
| 56 | N-[4'-methyl-2-(2-morpholin-4-yl-2-oxoethyl)-4,5'-bi-1,3-thiazol-2'-yl]acetamide; |
| 57 | 2-[2'-(acetylamino)-4'-methyl-4,5'-bi-1,3-thiazol-2-yl]acetamide; |
| 58 | tert-butyl 4-{[2-(cyanomethyl)-4'-methyl-4,5'-bi-1,3-thiazol-2'-yl]amino}-4-oxobutanoate; |
| 59 | methyl 5-{[2-(cyanomethyl)-4'-methyl-4,5'-bi-1,3-thiazol-2'-yl]amino}-5-oxopentanoate; |
| 60 | methyl 6-{[2-(cyanomethyl)-4'-methyl-4,5'-bi-1,3-thiazol-2'-yl]amino}-6-oxohexanoate; |
| 61 | 2'-(acetylamino)-N,N,4'-trimethyl-4,5'-bi-1,3-thiazole-2-carboxamide; |
| 62 | 2'-(acetylamino)-4'-methyl-4,5'-bi-1,3-thiazole-2-carboxamide; |
| 63 | 4-{[2-(cyanomethyl)-4'-methyl-4,5'-bi-1,3-thiazol-2'-yl]amino}-4-oxobutanoic acid; |
| 64 | 5-{[2-(cyanomethyl)-4'-methyl-4,5'-bi-1,3-thiazol-2'-yl]amino}-5-oxopentanoic acid; |
| 65 | tert-butyl N-({[2-(cyanomethyl)-4'-methyl-4,5'-bi-1,3-thiazol-2'-yl]amino}carbonyl)glycinate; |
| 66 | tert-butyl 4-[({[2-(cyanomethyl)-4'-methyl-4,5'-bi-1,3-thiazol-2'-yl]amino}carbonyl)amino]butanoate; |
| 67 | N~2~-({[2-(cyanomethyl)-4'-methyl-4,5'-bi-1,3-thiazol-2'-yl]amino}carbonyl)-N~1~,N~1~-dimethylglycinamide; |
| 68 | tert-butyl N-({[4'-methyl-2-(morpholin-4-ylcarbonyl)-4,5'-bi-1,3-thiazol-2'-yl]amino}carbonyl)-beta-alaninate; |
| 69 | N-[4'-methyl-2-(morpholin-4-ylcarbonyl)-4,5'-bi-1,3-thiazol-2'-yl]-N-(2-morpholin-4-yl-2-oxoethyl)urea; |
| 70 | N-[2-(cyanomethyl)-4'-methyl-4,5'-bi-1,3-thiazol-2'-yl]-N-(2-morpholin-4-yl-2-oxoethyl)urea; |
| 71 | methyl N-({[2-(cyanomethyl)-4'-methyl-4,5'-bi-1,3-thiazol-2'-yl]amino}carbonyl)-beta-alaninate; |
| 72 | N~3~-({[2-(cyanomethyl)-4'-methyl-4,5'-bi-1,3-thiazol-2'-yl]amino}carbonyl)-N~1~,N~1~-diisopropyl-beta-alaninamide; |
| 73 | N~3~-({[2-(cyanomethyl)-4'-methyl-4,5'-bi-1,3-thiazol-2'-yl]amino}carbonyl)-N~1~-(2-hydroxy-1,1-dimethylethyl)-beta-alaninamide; |
| 74 | N~1~-(tert-butyl)-N~3~-({[2-(cyanomethyl)-4'-methyl-4,5'-bi-1,3-thiazol-2'-yl]amino}carbonyl)-beta-alaninamide; |
| 75 | N-[2-(cyanomethyl)-4'-methyl-4,5'-bi-1,3-thiazol-2'-yl]-N-[3-(2,2-dimethyl-1,3-thiazolidin-3-yl)-3-oxopropyl]urea; |
| 76 | N-[2-(cyanomethyl)-4'-methyl-4,5'-bi-1,3-thiazol-2'-yl]-N-[3-(4,4-dimethyl-1,3-oxazolidin-3-yl)-3-oxopropyl]urea; |

| Example N° | Name |
|---|---|
| 77 | N~2~-({[2-(cyanomethyl)-4'-methyl-4,5'-bi-1,3-thiazol-2'-yl]amino}carbonyl)-N~1~-(2,2-dimethylpropyl)glycinamide; |
| 78 | N-(3-azocan-1-yl-3-oxopropyl)-N-[2-(cyanomethyl)-4'-methyl-4,5'-bi-1,3-thiazol-2'-yl]urea; |
| 79 | N-[2-(cyanomethyl)-4'-methyl-4,5'-bi-1,3-thiazol-2'-yl]-N'-[2-(1-isopropyl-1H-imidazol-4-yl)ethyl]urea; |
| 80 | N-[2-(cyanomethyl)-4'-methyl-4,5'-bi-1,3-thiazol-2'-yl]-N'-[2-(1-ethyl-1H-imidazol-4-yl)ethyl]urea; |
| 81 | N-[2-(5-tert-butyl-1,2,4-oxadiazol-3-yl)ethyl]-N'-[2-(cyanomethyl)-4'-methyl-4,5'-bi-1,3-thiazol-2'-yl]urea; |
| 82 | N-[2-(cyanomethyl)-4'-methyl-4,5'-bi-1,3-thiazol-2'-yl]-N'-[2-(5-isopropyl-1,2,4-oxadiazol-3-yl)ethyl]urea; |
| 83 | N-(4'-methyl-2-{[5-(1-methylpiperidin-4-yl)-1,2,4-oxadiazol-3-yl]methyl}-4,5'-bi-1,3-thiazol-2'-yl)acetamide. |

The compounds of the present invention are useful as medicaments. They may be used for the preparation of a medicament for the prophylaxis and/or treatment of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including Alzheimer's disease, Huntington's disease, CNS trauma, stroke or ischemic conditions.

In still a further embodiment according to the invention, the compounds of Formula (I) are useful for the treatment and/or prophylaxis of cardiovascular diseases such as atherosclerosis, heart hypertrophy, cardiac myocyte dysfunction, elevated blood pressure or vasoconstriction.

In still a further embodiment according to the invention, the compounds of Formula (I) are useful for the treatment and/or prophylaxis of erythrocyte deficiency such as an anaemia, including haemolytic anaemia, aplastic anaemia and pure red cell anaemia.

In still another embodiment according to the invention, the compounds of Formula (I) are useful for the treatment and/or prophylaxis of chronic obstructive pulmonary disease, anaphylactic shock, fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Kaposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In another embodiment according to the invention, is provided a process for the preparation of thiazole derivatives according to Formula (I), comprising the step of reacting an amine of Formula (Ia) with a derivative of Formula ClC(O)R⁶ group in presence of a base, e.g. pyridine, DIEA, TEA, etc.

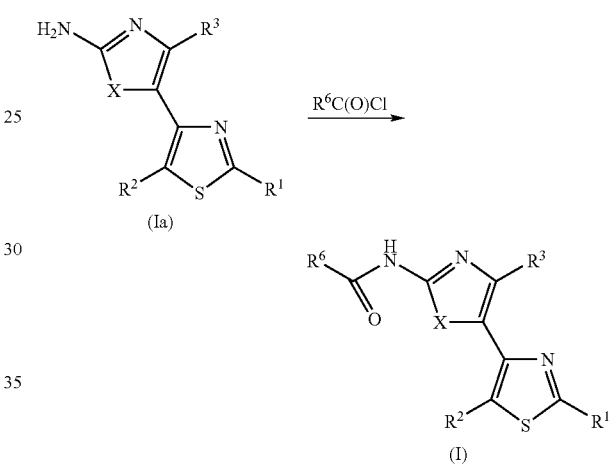

wherein $R^1$, $R^2$, $R^3$, $R^6$ and X are defined in the description.

In another embodiment according to the invention, is provided a process for the preparation of thiazole derivatives according to Formula (I), comprising the step of heating an amine of Formula (Ia) in formic acid or in any alkyl formate, with optionally a co-solvent.

In another embodiment according to the invention, is provided a process for the preparation of thiazole derivatives according to Formula (I), comprising the step of reacting an amine of Formula (Ia) with a derivative of Formula $R^7R^8NC(O)$ in presence of a base, e.g. DIEA, TEA, etc., wherein $R^7$ and $R^8$ are selected from H; optionally substituted $C_1$-$C_6$-alkyl, such as methoxyethyl (e.g. 2-methoxyethyl), carboxylic acid alkyl (e.g. 3-carboxylic acid ethyl), 3-carboxylic acid alkyl ester ethyl (e.g. 3-carboxylic acid ethyl ester ethyl, 3-carboxylic acid t-butyl ester ethyl), amino carbonyl methyl (e.g. N,N-dimethylamino carbonyl methyl).

In another embodiment according to the invention, is provided a process for the preparation of thiazole derivatives according to Formula (I), comprising the step of reacting an amine of Formula (Ia) with CDI, followed by the addition of an amine of Formula $R^7R^8NH$, wherein $R^7$ and $R^8$ are selected from H; optionally substituted $C_1$-$C_6$-alkyl such as methoxyethyl (e.g. 2-methoxyethyl), carboxylic acid alkyl (e.g. 3-carboxylic acid ethyl), 3-carboxylic acid alkyl ester ethyl (e.g. 3-carboxylic acid ethyl ester ethyl, 3-carboxylic acid t-butyl ester ethyl), amino carbonyl methyl (e.g. N,N-dimethylamino carbonyl methyl).

In another embodiment according to the invention, is provided a process for the preparation of thiazole derivatives according to Formula (I), comprising the step of reacting a derivative of formula (P3) with an amine of formula $HNR^9R^{10}$, in the presence of a base, e.g. pyridine, DIEA, TEA, etc

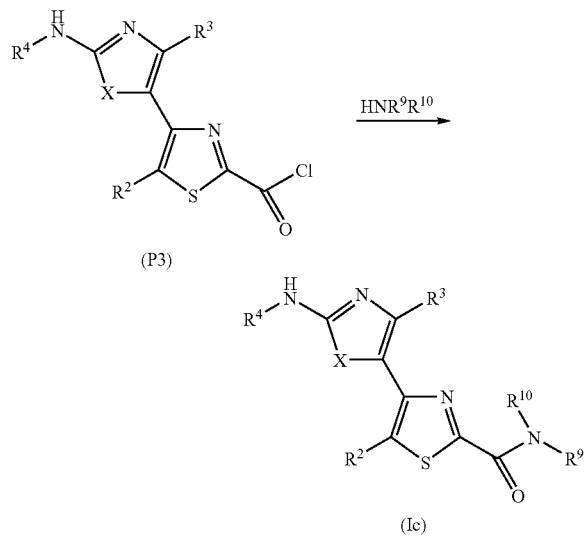

wherein $R^1$, $R^2$, $R^3$, $R^4$ and X are defined in the description and $R^9$ and $R^{10}$ are selected from H; optionally substituted $C_1$-$C_6$-alkyl such as allyl, methoxyethyl (e.g. 2-methoxyethyl), methoxy propyl (e.g. 3-methoxy-propyl), hydroxy ethyl (e.g. 2-hydroxyethyl), hydroxyl propyl (e.g. 2,3-dihydroxypropyl), cyano ethyl (e.g. 2-cyanoethyl), propyl (e.g. n-propyl), prop-2-ynyl, tetrahydrofuran methyl (e.g. tetrahydrofuran-2-yl-methyl), dimethyl amino ethyl (e.g. 2-(dimethylamino)ethyl), dimethyl amino propyl (e.g. 3-(dimethylamino)propyl), tetrazolyl (e.g. 1H-tetrazol-5-yl, 1H-tetrazol-3-yl), benzoic acid (e.g. 4-benzoic acid, 3-benzoic acid, 2-hydroxy-3-benzoic acid, 3-hydroxy-4-benzoic acid, 3-fluoro-4-benzoic acid, 4-hydroxy-3-benzoic acid), tetrazolyl phenyl (e.g. 3-(1H-tetrazol-5-yl)phenyl, 3-(1H-tetrazol-3-yl)phenyl, 4-(1H-tetrazol-5-yl)phenyl, 4-(1H-tetrazol-3-yl)phenyl), thiadiazolyl phenyl (e.g. 3-(5-amino-1,3,4-thiadiazol-2-yl)phenyl), oxadiazolyl phenyl (e.g. 3-(5-hydroxy-1,3,4-oxadiazol-2-yl)phenyl, 4-(5-hydroxy-1,3,4-oxadiazol-2-yl)phenyl), benzyl (e.g. benzyl, 1H-1,2,3, benzotriazol-5-yl; optionally substituted aryl; optionally substituted heteroaryl; optionally substituted $C_3$-$C_8$ cycloalkyl;

optionally —$NR^9R^{10}$ may form a ring, and may be selected from substituted heterocycloalkyl, including morpholinyl (e.g. morpholin-4-yl), piperazinyl (e.g. 4-methylpiperazin-1-yl, 4-acetylpiperazin-1-yl, 3-oxopiperazin-1-yl), piperidinyl (e.g. 3-carboxylic acid piperidin-1-yl, 4-carboxylic acid piperidin-1-yl, 4-(hydroxylmethyl)piperidin-1-yl, 3-hydroxypiperidin-1-yl, 4-hydroxypiperidin-1-yl, 4-(2-hydroxyethyl)piperidin-1-yl, 4-fluoropiperidin-1-yl, 4-oxopiperidin-1-yl), 1,4-dioaxa-8-azaspiro[4.5]decan-8-yl, 7-(hydroxymethyl)-6,8-dioxa-3-azabicyclo[3.2.1]oct-3-yl, pyrrolidinyl (e.g. 3-hydroxypyrrolidin-1-yl);

In another embodiment according to the invention, is provided a process for the preparation of thiazole derivatives according to Formula (I), comprising the step of reducing a derivative of formula (P3) with addition of hydride such as lithium tri-tert-butoxyaluminohydride ((tBuO)$_3$AlHLi).

In another embodiment according to the invention, are provided compounds according to Formula (Ia):

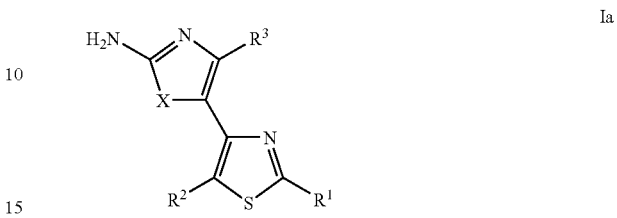

wherein $R^1$, $R^2$, $R^3$ and X are as defined in the description and with the proviso that the compounds of formula Ia are not the following compounds:
[4,5'-Bithiazole]-2-acetonitrile, 2'-amino-4'-methyl- (Registry n°: 299171-15-6);
2'-amino-4'-methyl-(phenylhydrazono)-[4,5'-Bithiazole]-2-acetonitrile, (Registry n°: 299171-18-9);
2'-amino-[(4-chlorophenyl)hydrazono]-4'-methyl-[4,5'-Bithiazole]-2-acetonitrile (Registry n°: 299171-19-0); or
[4,5'-Bithiazole]-4'-carboxylic acid, 2'-amino-2-methyl-, ethyl ester (Registry n°: 94273-53-7).

In a further embodiment according to the invention, are provided compounds according to Formula (Ia) selected from the following group:
ethyl 2'-amino-4'-methyl-4,5'-bi-1,3-thiazole-2-carboxylate; and
4'-methyl-2-(morpholin-4-ylcarbonyl)-4,5'-bi-1,3-thiazol-2'-amine.

In a further embodiment according to the invention, are provided compounds according to Formula (P3) from the group:

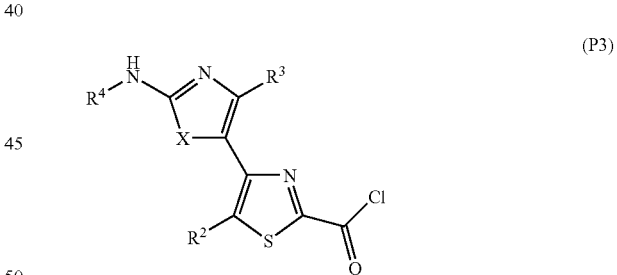

wherein $R^2$, $R^3$ and $R^4$ are defined in the description.

In a further embodiment according to the invention, is provided a compound according to Formula (P3):
2'-(Acetylamino)-4'-methyl-4,5'-bi-1,3-thiazole-2-carbonyl chloride.

The thiazole derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing thiazole derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the thiazole derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the thiazole derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences, 20th Edition*, 2000, Marck Publishing Company, Easton, Pa., which is incorporated herein by reference. The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel thiazole derivatives according to Formula (I) can be prepared from readily available starting materials by several synthetic approaches, using both solution-phase and solid-phase chemistry protocols. Examples of synthetic pathways for the will be described.

The following abbreviations refer respectively to the definitions below:

Å (Angström), eq (equivalent), h (hour), g (gram), M (molar), MHz (Megahertz), µl (microliter), min (minute), mg (milligram), ml (milliliter), mm (millimeter), mmol (millimole), mM (millimolar), nm (nanometer), rt (room temperature), BSA (Bovine Serum Albumin), CDI (N,N'-carbonyldiimidazole), DCC (dicyclohexyl carbodiimide), DCM (dichloromethane), DIEA (diisopropyl ethylamine), DMEM (Dulbecco's Modified Eagle Medium), DMF (dimethyl formamide), EDC (1-(3-dimethylaminopropy1)-3-ethyl-carbo diimidehydro-chloride), HPLC (High Performance Liquid Chromatography), HOBt (1-hydroxybenzo triazole), IHC (immunohistochemistry), Ins1P (D-myo-inositol-1-phosphate), LC (Liquid chromatography), MS (mass spectrometry), NBS (N-bromo succinimide), NIS (N-iodo succinimide), NMR (Nuclear Magnetic Resonance), PBS (Phosphate Buffered Saline), PIs (Phosphoinositides), PI3Ks (Phosphoinositide 3-kinases), PI(3)P (Phosphatidylinositol 3-monophosphate), PI(3,4)P$_2$(Phosphatidylinositol 3,4-bisphosphate), PI(3,4,5)P$_3$ (Phosphatidylinositol 3,4.5-trisphosphate), PI(4)P (Phosphatidylinositol-4-phosphate), PI(4,5)P$_2$) (Phosphatidyl inositol-4,5-biphosphate), PtdIns (Phosphatidylinositol), TEA (triethylamine), TFA (trifluoroacetic acid), TFAA (trifluoroanhydride), THF (tetrahydrofuran), UV (Ultraviolet).

The thiazole derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In the process illustrated in the following schemes $R^1$, $R^2$, $R^3$, $R^4$, $R^5$, $R^6$, $R^7$, $R^8$, $R^9$, $R^{10}$ and X as above-defined in the description.

Generally, the thiazole derivatives according to the general Formula (I) could be obtained by several synthetic approaches, using both solution-phase and solid-phase chemistry protocols (Kodomari et al., 2002; Pirrung et al., 2001, above), either by conventional methods or by microwave-assisted techniques.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

Methods of preparing intermediates of compounds of Formula (I).

Depending on the nature of $R^1$, $R^2$, $R^3$, $R^4$, $R^5$, $R^6$, $R^7$, $R^8$, $R^9$, $R^{10}$ and X different synthetic strategies may be selected for the synthesis of compounds of Formula (I).

One synthetic approach (Scheme 1 below) consists of reacting approximately equimolar amounts of an α-bromoketone reactant (P1) with an alkyl thiooxamate, such as ethyl thiooxamate, or a thioamide, such as 2-cyanothioacetamide (P2), in a solvent, preferably polar such as alcoholic solvent, to afford a compound of Formula (I). The temperature of the reaction depends on the nature of (P1) and (P2), ranging between −20° C. and reflux. The use of a base to trap the liberated HBr, such as DIEA or TEA, is optional.

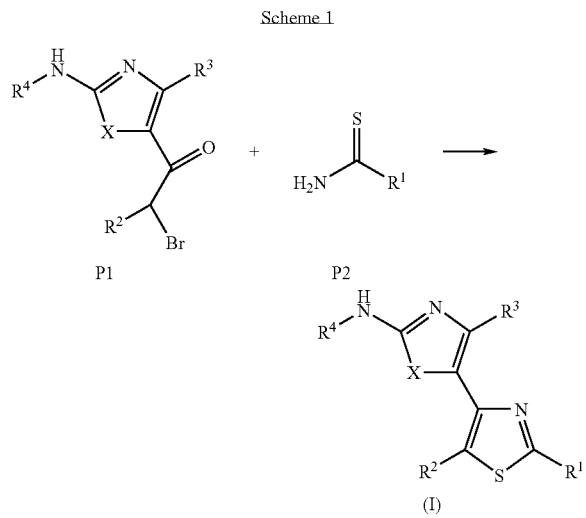

When $R^4$ is —C(O)$R^6$, as defined above, a different approach may be also used for the preparation of Compounds of Formula (I), as it is described in Scheme 2 below. It consists of reacting amine derivative (P1a), with an alkyl thiooxamate, such as ethyl thiooxamate, or a thioamide, such as 2-cyanothioacetamide (P2), affording the corresponding bis-thiazole or oxazole-thiazole of Formula (Ia).

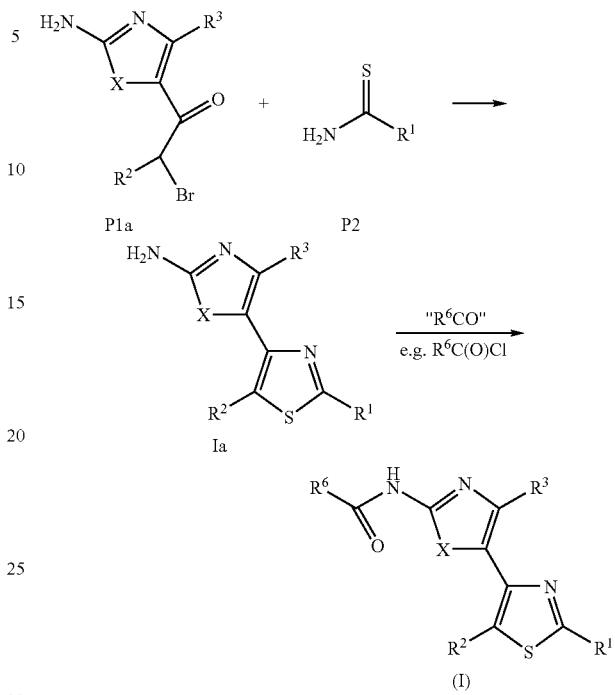

Functionalization of the primary amine (Ia) with —C(O)$R^6$ as defined above in the description may be then performed, using conditions known by the person skilled in the art, affording compounds of Formula (I).

When —C(O)$R^6$ group is an acyl group, the corresponding acyl chloride or acyl anhydride may be added to intermediate (Ia) in the presence of a base, e.g. pyridine, DIEA, TEA, etc. The corresponding carboxylic acid can be also added in the presence of an activating agent such as DCC, EDC, etc.

A formyl group, i.e. —C(O)$R^6$=—C(O)H, can be introduced by heating intermediate (Ia) in formic acid or in any alkyl formate, with or without a co-solvent.

A substituted urea may be prepared by addition of an isocyanate $R^7R^8$NC(O), wherein $R^7$ and $R^8$ have been defined above, to intermediate (Ia) in the presence of a base, e.g. DIEA, TEA, etc. The sequential addition of CDI and a substituted primary or secondary amine HN$R^7R^8$ to intermediate (Ia) may also afford compounds of Formula (I) with —C(O)$R^6$=—C(O)N$R^7R^8$, wherein $R^7$ and $R^8$ have been defined above.

Compounds of Formula (I) with —C(O)$R^6$=—C(O)N$R^7R^8$, as defined above, may be converted to alternative compounds of Formula (I), by transforming —NHC(O)N$R^7R^8$ moiety into an alternative urea —NHC(O)N$R^7R^8$, employing suitable interconversion techniques well known by a person skilled in the art.

Depending on the nature of $R^1$, compounds of Formula (I) can be transformed into alternative compounds of Formula (I) by modifying group $R^1$ as defined above.

When $R^1$ is an ester ($R^1$=—C(O)$R^5$ where $R^5$ is an alkoxy —OAlk, e.g. ethoxy), compounds of Formula (Ib) can be transformed into an amide of Formula (Ic), with $R^5$=—N$R^9R^{10}$, as defined above. This transformation can be achieved in one or two steps, depending on the nature of the amine HN$R^9R^{10}$, wherein $R^9$ and $R^{10}$ have been defined above (Scheme 3, below).

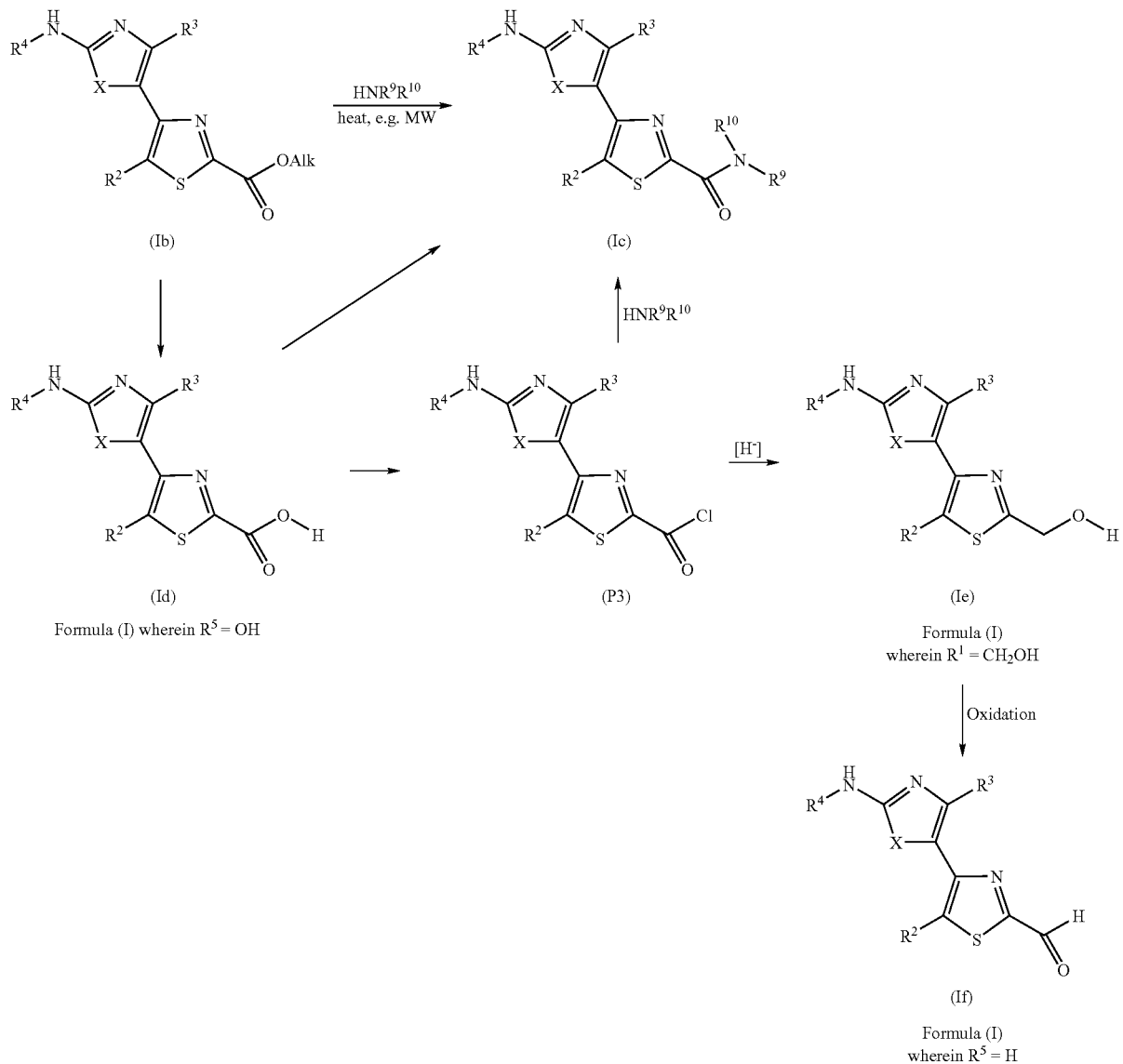

Scheme 3

For amines with low boiling points, amide (Ic) may be obtained by heating ester of formula (Ib) with the amine $HNR^9R^{10}$ used as solvent under microwave action, wherein $R^9$ and $R^{10}$ have been defined above. Amide (Ic) can be typically obtained after 10 to 30 min at 80° C. in the microwave.

An alternative procedure consists in the preparation of the corresponding carboxylic acid (Id) with $R^5$=OH under basic conditions, followed by the formation of an amide bond with amine $HNR^9R^{10}$, as defined above. For this second step, different activating agents may be used, such as DCC, EDC, HOBt, etc. Addition of a base, such as TEA or DIEA, may be needed, depending on the nature of the coupling agent. Solvents may be chosen between DCM, DMF, MeCN or any other solvents suitable for such transformation.

Carboxylic acid (Id) may be first transformed into the corresponding acid chloride (P3), using a suitable reagent such as oxalyl chloride or thionyl chloride. Reaction of the resulting acid chloride with amine $HNR^9R^{10}$, in the presence of a base, e.g. pyridine, DIEA, TEA, etc, may afford compounds of Formula (Ic) wherein $R^1$=—C(O)$R^5$=—C(O)$NR^9R^{10}$, as defined above.

Amines $HNR^9R^{10}$ may be commercially available from various sources or synthesized, as it will be detailed below in the examples, using conditions known to the person skilled in the art.

Alcohol of Formula (Ie) ($R^1$=CH$_2$OH) may be prepared by reduction of intermediate (P3), with addition of hydride such as lithium tri-tert-butoxyaluminohydride (tBuO)$_3$AlHLi). The corresponding aldehyde of Formula (If), with $R^1$=C(O)$R^5$=C(O)H, may be obtained by oxidation of alcohol (Ie), using conditions know by the person skills in the art, such as Swern or Dess Martin oxidation.

Depending on the nature of $R^1$, different reagent (P2) may be used for the preparation of compounds of Formula (I).

When $R^1$ is —C(O)$R^5$, where $R^5$ is substituted alkoxy, e.g. ethoxy, compounds of Formula (Ib) may be obtained by reaction of approximately equimolar amounts of an α-bromoketone (P1) with an alkyl thiooxamate, such as ethyl thiooxamate (P2a) (see Scheme 4, below).

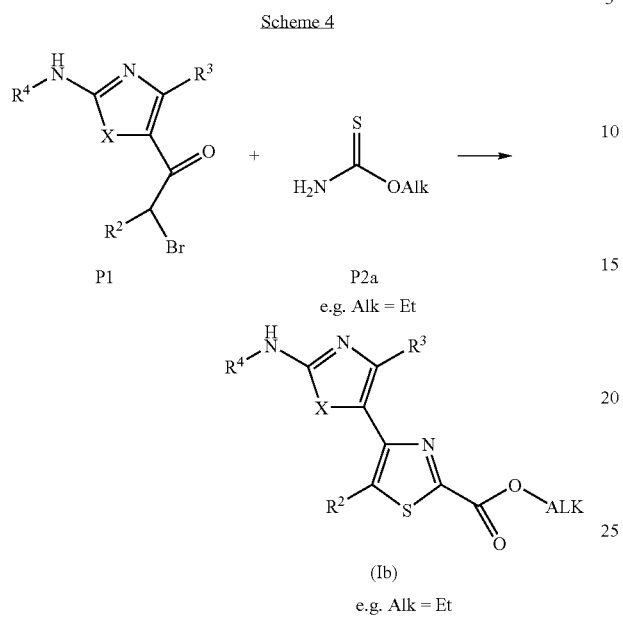

Scheme 4

When R¹ is a substituted $C_1$-$C_6$-alkyl, e.g. cyanomethyl, compounds of Formula (I) may be obtained by reaction of approximately equimolar amounts of an α-bromoketone (PI) with an alkyl thioamide $R^1C(S)NH_2$, (P2b), such as 2-cyanothioacetamide (see Scheme 5, below).

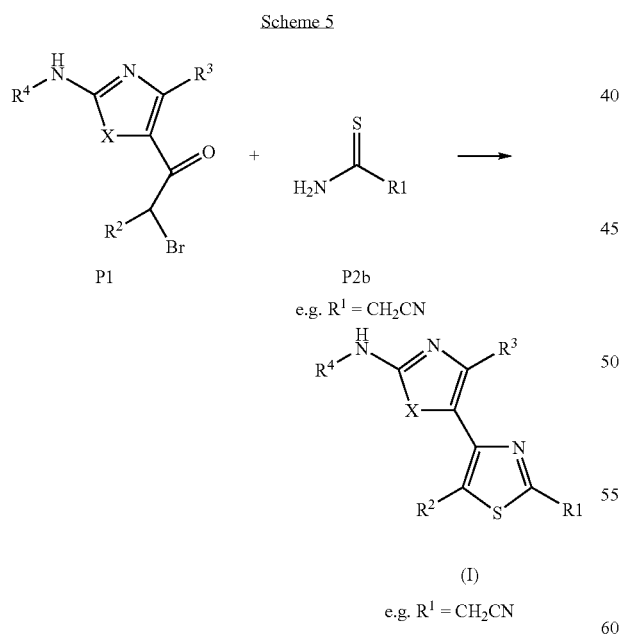

Scheme 5

Compounds of Formula (I) may be transformed into alternative compounds of Formula (I). For example, when $R^1$=$CH_2CN$, compounds of Formula (Ig) may be transformed into tetrazolyl methyl derivatives such as 2H-tetrazol-5-yl-methyl (Ih), using conditions known by a person skilled in this art (Scheme 6, below).

For instance, compounds of Formula (I) wherein R¹ is —$CH_2$-tetrazolyl, i.e. compound of formula (Ih) may be obtained by the reaction of (Ig) with an azide, such as sodium azide in the presence of $Bu_3SnCl$ (4 eq.), or $TMSN_3$ in the presence of a catalytic amount of $Bu_2SnO$ (Wittenberger et al., 1993, *J. Org. Chem.*, 58, 4139).

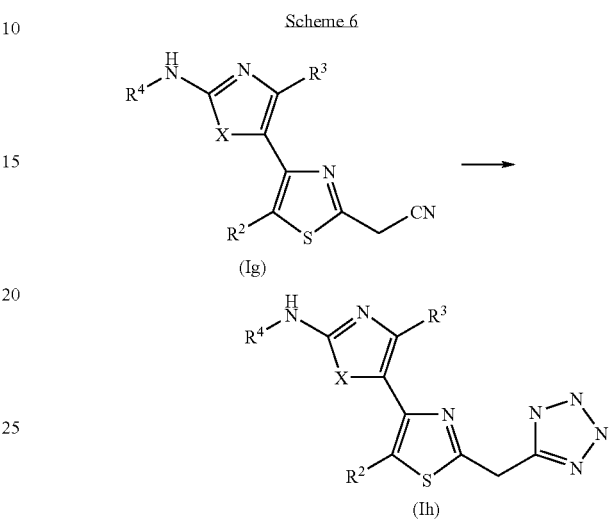

Scheme 6

α-Bromoketone (P1) may be obtained by a α-bromination of ketone (P4) (Scheme 7, below). Different bromination agents can be used, such as $Br_2$, in the optional presence of HBr, or NBS.

Depending on the nature of R⁴, the free NH group may be first protected, before proceeding to the bromination (Scheme 7 below). It can be then removed using conditions known by a person skilled in the art, affording intermediate (P1). PG may be any protecting group that can be easily removed, e.g. an acetyl group.

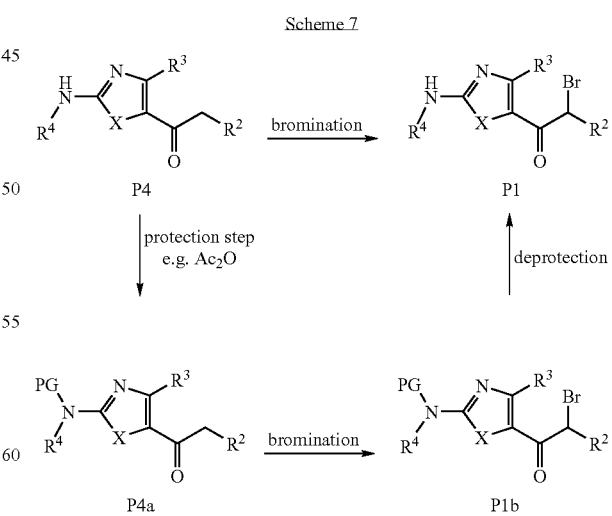

Scheme 7

When R⁴ is —$C(O)R^6$, α-bromoketone (P1c) may be obtained in two steps, from substituted 5-acyl-2-amino thiazole (P5) as shown on Scheme 8 below.

Scheme 8

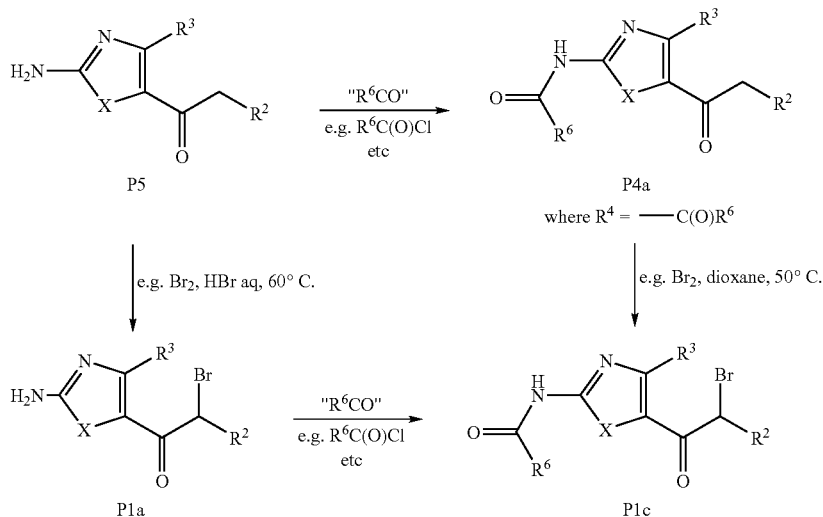

Functionalization of the primary amine in (P5), with —C(O)R$^6$ as defined above in the description, can be performed first, affording (P4a).

When —C(O)R$^6$ is an acyl group, the corresponding acyl chloride or acyl anhydride may be added to intermediate (P5) in the presence of a base, e.g. pyridine, DIEA, TEA, etc. The corresponding carboxylic acid may be also added in the presence of an activating agent such as DCC, EDC, etc.

A formyl group, —C(O)R$^6$=—C(O)H, can be introduced by heating intermediate (P5) in formic acid or in any alkyl formate, with or without a co-solvent.

A substituted urea may be prepared by addition of an isocyanate, R$^7$R$^8$NC(O), to intermediate (P5) in the presence of a base, e.g. DIEA, TEA, etc, wherein R$^7$ and R$^8$ have been defined above. The sequential addition of CDI and a substituted primary or secondary amine HNR$^7$R$^8$ to intermediate (P5) may also afford intermediate (P4a) with —C(O)R$^6$=—C(O)NR$^7$R$^8$, as defined above Compounds of Formula (P4a) with —C(O)R$^6$=—C(O)NR$^7$R$^8$ may be converted to alternative compounds of Formula (P4a), by transforming —NHC(O)NR$^7$R$^8$ moiety into an alternative urea —NHC(O)NR$^7$R$^8$, wherein R$^7$ and R$^8$ have been defined above, employing suitable interconversion techniques well known by a person skilled in the art.

This first acylation step may be followed by a α-bromination of the 5-acyl group to afford intermediate (P1c) (Scheme 8, above).

These two steps can be performed in the reverse order (Scheme 8, above). Bromination of intermediate (P5) may be performed first, affording intermediate (P1a). Intermediate (P1c) may be then obtained after introduction of —C(O)R$^6$ group as defined above in the description, using the conditions described above.

In both synthetic pathways, different bromination agents can be used, such as Br$_2$, in the optional presence of HBr or NBS.

Intermediates according to Formula (P4) and (P5) are either commercially available from various sources or can be obtained by different synthetic approaches, using both solution-phase and solid-phase chemistry protocols.

Examples of intermediate (P4) and (P5) synthesis are proposed on Scheme 9 hereinafter.

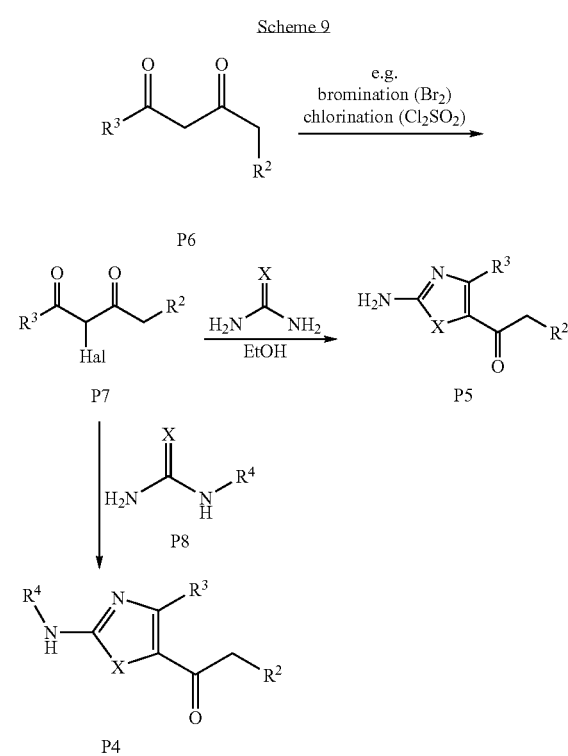

A substituted bi-ketone (P6) may be halogenated, using for example Br$_2$ for a bromination or thionyl chloride for α-chlorination, affording an intermediate (P7). "Hal" in intermediate (P7) can be also a tosyloxy group, which may be introduced with suitable reagents such as hydroxy(tosyloxy)iodobenzene. Intermediate (P7) may be then added to a solution of thiourea or urea in a suitable solvent, preferably a polar solvent, e.g. EtOH, leading to intermediate (P5).

The specific reaction conditions, temperature, time, etc, may depend on the nature of X and substituents $R^2$ and $R^3$, according to the literature and as it will be detailed below in the examples (Sayed et al., 1999, *Heteroatom Chemistry*, 10, 385-390).

Intermediate (P4) can be directly obtained from the reaction of (P7) with the suitable thiourea or urea (P8), substituted with a —$R^4$ group as it has been defined above in the description. Thioureas or ureas (P8) are either commercially available or obtained, using conditions known to a person skilled in the art.

Some conditions are described in the examples below or in Herr et al., 2000, *Synthesis*, 2000, 1569-1574 and Wilson et al., 2001, *J. Bioorg. Med. Chem. Lett.*, 11, 915-918.

When $R^3$=H, (P6a) is prepared in one step, as sodium salt, by the condensation of a methyl ketone with ethyl formate, as described on Scheme 10 below. It is then directly brominated, affording intermediate (P7a), according to the literature and as it will be detailed below in the examples.

Scheme 10

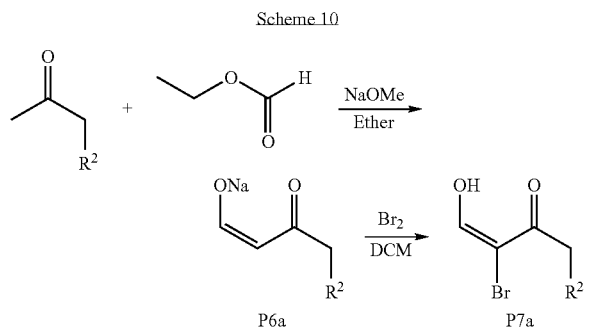

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3rd Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The following starting materials commercially available were used:

5-Acetyl-2-amino-4-methylthiazole (Flrochem), 3-chloro-2,4-pentanedione (Fluka), 2-amino pyrazine (Aldrich), 3-amino pyrazole (Aldrich), 2-hydroxy-5-nitro-benzoique acid (Aldrich), 3-aminobenzonitrile (Aldrich), 4-aminosalicylic acid (Aldrich), 3-nitrobenzoic acid (Aldrich), 4-nitrobenzoic acid (Aldrich), ethyl thiooxamate (Aldrich), allylamine (Fluka), 2-cyanothioacetamide (Aldrich), 2-methoxyethylamine (Fluka), tetrahydrofurfurylamine (Fluka), 2-dimethylaminoethylamine (Fluka), morpholine (Fluka), 1-methylpiperazine(Fluka), N,N-dimethyl-1,3-propanediamine (Fluka), ethanolamine (Fluka), N-(2-cyanoethyl) amine (Lancaster), 5-aminotetrazole (Aldrich), 4-aminobenzoic acid (Aldrich), 3-aminobenzoic acid (Emkachem), 5-(3-aminophenyl)tetrazole (Avocado), benzylamine (Fluka), N-propylamine (Fluka), 4-(2H-tetrazol-3-yl)aniline hydrochloride (Asimex), 3-aminosalicylic acid (TCI-US), nipecotic acid (Emkachem), isonipecotic acid (Fluka), 3-hydroxypiperidine (Fluka), 4-(hydroxymethyl)piperidine (Maybridge), 4-piperidineethanol (Aldrich), 4-hydroxypiperidine (Fluka), 5-aminobenzotriazole (Aldrich), 4-amino-2-fluorobenzoic acid (Apollo), lithium tri-tert-butoxyaluminohydride (Aldrich), ethyl 2-isocyanatopropionate (Aldrich), 1,4-dioxa-8-azaspiro[4.5]decane (Aldrich), 2,2-dimethyl-1,3-dioxolane-4-methanamine (Aldrich), piperazin-2-one (Aldrich), 4-piperidone hydrochloride monohydrate (Aldrich), 3-pyrrolidinol (Fluka), propargylamine (Fluka), 1-acetylpiperazine (Aldrich), glycine dimethylamide acetate (Chem-Impex), beta-alanine (Aldrich), 4-fluoropyperidine (Flrochem), β-alanine t-butyl ester hydrochloride (Bachem). (1S,5S,7S)-6,8-dioxa-3-azabicyclo[3.2.1]oct-7-ylmethanol and (1R,5R,7R)-6,8-Dioxa-3-azabicyclo[3.2.1]oct-7-ylmethanol were synthesized according published procedures (see Guarna et al, 1999, *J. Org. Chem.*, 64, 7347).

The HPLC, NMR and MS data provided in the examples described below are obtained as followed: HPLC: Method A: column Waters Symmetry C8 50×4.6 mm, Conditions: MeCN 0.05% TFA/$H_2O$ 0.1% TFA, 5 to 100% (8 min), max plot 230-400 nm; Method B: column C18 BDS 250×4.6 mm, SC\243, Conditions: MeCN/$H_2O$ 0.1% TFA, 5 to 100% (15 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep NOVA-PAK HR C18 6μm 60 Å, 40×30mm (up to 100 mg) or with XTERRA Prep MS C8, 10 μm, 50×300 mm (up to 1 g). All the purifications are performed with a gradient of MeCN/$H_2O$ 0.09% TFA. The semi-preparative reverse-phase HPLC are performed with the Biotage Parallex Flex System equipped with columns SUPELCOSIL ABZ+Plus (25 cm×21.2 mm, 12 μm); UV detection at 254 nm and 220 nm; flow 20 ml/min (up to 50 mg). TLC Analysis is performed on Merck Precoated 60 $F_{254}$ plates. Purifications by flash chromatography are performed on $SiO_2$ support, using cyclohexane/EtOAc or DCM/MeOH mixtures as eluents.

The microwave chemistry is performed on a single mode microwave reactor Emrys™ Optimiser from Personal Chemistry.

Intermediate 1: Preparation of N-[5-(bromoacetyl)-4-methyl-1,3-thiazol-2-yl]acetamide, hydrobromide salt (Intermediate (PI) wherein $R^2$ is H, $R^3$ and $R^6$ are methyl and X is S)

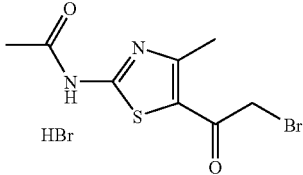

Intermediate 1

Step I: N-(5-acetyl-4-methyl-1,3-thiazol-2-yl)acetamide (Intermediate (P6) wherein $R^2$ is H, $R^3$ and $R^4$ are methyl and X is S)

5-Acetyl-2-amino-4-methylthiazole (P5)(Flrochem)(12.4 g, 79 mmol) is suspended in THF/DCM 3:2 mixture (150 ml). The mixture is cooled down to 0° C. and pyridine (16 ml) is added, followed by the dropwise addition of acetyl chloride (8.43 ml, 119 mmol, 1.5 eq.). The mixture is stirred 2 hours at 0° C. As the acetylation is complete, the reaction is quenched with addition of water (70 ml) and diluted with EtOAc (100 ml). The two phases are separated and the organic phase is washed with one portion of 10% citric acid solution. Organic layer is dried over $MgSO_4$, filtrated and evaporated. The resulting crude mass is purified by crystallization in EtOAc/Cyclohexane mixture, to obtain N-(5-acetyl-4-methyl-1,3-thiazol-2-yl)acetamide (P6) as a colorless powder (13.1 g, 83.6% yield). $^1$H NMR (DMSO-$d_6$) δ: 2.17 (s, 3H), 2.47 (s, 3H), 2.56 (s, 3H), 12.44 (br s, 1H). M$^-$ (ESI): 197.3; M$^+$ (ESI): 199.3. HPLC (method A), Rt: 1.7 min (purity: 99.7%).

Step II: N-[5-(bromoacetyl)-4-methyl-1,3-thiazol-2-yl]acetamide, hydrobromide salt (Intermediate 1)

A solution of $Br_2$ (3.35 ml, 65.6 mmol) in 75 ml dioxane is added dropwise to a solution of N-(5-acetyl-4-methyl-1,3-thiazol-2-yl)acetamide (P6), obtained in Step I as described above, (10.40 g, 52.5 mmol) in 200 ml dioxane. The resulting mixture is heated at 50° C. for 19 hours. The solution turns from dark red to beige and remains a heterogeneous mixture. By analytical HPLC, only 2.8% of starting material is detected. The suspension is filtered, washed with a 1:2 EtOAc/hexanes mixture (50 ml) and air dried for 15 min, to give Intermediate 1 as a beige solid (11.2 g, 60%). It is used in bis-thiazol synthesis as HBr salt or as parent, after 5 min treatment with Amberlyst A21 in DCM/MeOH mixture.

$^1$H NMR (DMSO-$d_6$) δ: 2.04 (s, 3H), 2.44 (s, 3H), 4.52 (s, 2H), 12.44 (br s, 1H). M$^-$ (ESI): 276; M$^+$ (ESI): 278. HPLC (method A), Rt: 2.2 min (purity: 97.4%).

Intermediate 2: Preparation of 1-(2-amino-4-methyl-1,3-thiazol-5-yl)-2-bromo ethanone, hydrobromide salt (Intermediate (P1a) wherein $R^2$ is H, $R^3$ is methyl and X is S)

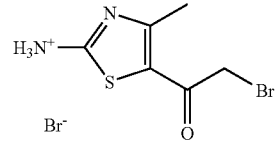

Intermediate 2

5-Acetyl-2-amino-4-methylthiazole (P5)(Flrochem)(1.0 g, 6.4 mmol) is suspended in 48% HBr solution in water (20 ml, 6.4 mmol). The mixture is warmed to 60° C. and a solution of $Br_2$ (0.262 ml, 5.12 mmol, 0.8 eq.) in dioxane (20 ml) is added dropwise. The mixture is stirred at 60° C. for 3 hours. The progression of the reaction is followed by LC/MS. When it is complete, the solvents are evaporated, and the water is removed by azeotropic distillation with toluene. The resulting solid is recrystallized in isopropanol/$Et_2O$ mixture, affording Intermediate 2 as colorless solid (890 mg, 74% yield). It is used in bis-thiazol synthesis as HBr salt or as parent, after 5 min treatment with Amberlyst A21 in DCM/MeOH mixture.

$^1$H NMR (DMSO-$d_6$) δ: 2.46 (s, 3H), 4.50 (s, 3H), 6.90 (br s, 1H), 9.18 (br s, 2H). M$^-$ (ESI): 234.1; M$^+$ (ESI): 236.1.

Intermediate 3: Preparation of 2-bromo-1-[4-methyl-2-(pyrazin-2-ylamino)-1,3-thiazol-5-yl]ethanone, hydrobromide salt (Intermediate (P1) wherein $R^4$ is 2-pyrazinyl, $R^2$ is H, $R^3$ is methyl and X is S)

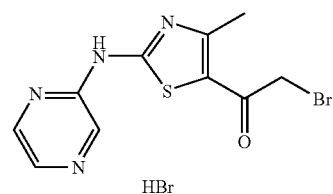

Intermediate 3

Step I: Preparation of N-Pyrazin-2-ylthiourea

To a solution of ammonium thiocyanate (17.8 g, 0.234 mol) in dry acetone (200 ml) at 0° C. under nitrogen is added benzoyl chloride (30 g, 0.213 mol) slowly over a period of 15 min. The reaction mixture is stirred at room temperature for 30 min and filtered. To the filtrate is added 2-amino pyrazine (16.2 g, 0.17 mol) dropwise and stirred for 3 h at room temperature. The solvent is removed under vacuum and the residue is diluted with water. The solid precipitated is filtered and dried to afford N-[(pyrazin-2-ylamino)carbonothioyl]benzamide as a solid (33 g; 76%). TLC—Chloroform/methanol (9/1): $R_f$–0.5.

A solution of N-[(pyrazin-2-ylamino) carbonothioyl]benzamide (25 g, 0.096 mol) in 10% NaOH solution (200 ml) is stirred at 80° C. for 20 min. The reaction mixture is cooled and the solvent is removed under vacuum. The residue is acidified with 2M HCl to pH=1 and then basified with ammonium hydroxide. The solid precipitated is collected by filtration and dried under suction affording N-Pyrazin-2-ylthiourea as a solid (12 g; 80%). $^1$H NMR (DMSO-$d_6$, 300 MHz): δ 8.24 (br s, 2H), 8.54 (s, 1H), 9.10 (m, 1H), 9.95 (m, 1H), 10.66 (br s, 1H). M$^+$ (ESI): 154.9. HPLC (Method B), Rt: 3.47 min (purity: 98.23%). TLC: Chloroform/methanol (9/1): $R_f$–0.25. Mp: 234° C.-235° C.

Step II: Preparation of 1-[4-Methyl-2-(pyrazin-2-ylamino)-1,3-thiazol-5-yl]ethanone, hydrochloride salt To a solution of N-pyrazin-2-ylthiourea (5 g, 0.032 mol) in absolute ethanol (50 ml) is added 3-chloro-2,4-pentanedione (4.4 g, 0.032 mol). The mixture is refluxed for 20 h under nitrogen. The reaction mixture is cooled down to rt and the resulting precipitate is filtered, washed with ethanol (25 ml) and dried under suction to afford 1-[4-Methyl-2-(pyrazin-2-ylamino)-1,3-thiazol-5-yl]ethanone, hydrochloride salt as white-off solid (7 g; 92%). $^1$H NMR (DMSO-$d_6$, 300 MHz): δ 2.47 (s, 3H), 2.57 (s, 3H), 8.21 (s, 1H), 8.41 (s, 1H), 8.48 (s, 1H), 12.2 (br s, 1H). M$^+$ (ESI): 234.9. HPLC (Method B), Rt: 1.56 min (purity: 97.75%). TLC: Chloroform/methanol (9/1): $R_f$–0.25. Mp: 224° C.-229° C.

Step III: Preparation of N-(5-acetyl-4-methyl-1,3-thiazol-2-yl)-N-pyrazin-2-ylacetamide In a tube, 1-[4-Methyl-2-(pyrazin-2-ylamino)-1,3-thiazol-5-yl]ethanone, hydrochloride salt (500 mg; 1.85 mmol; 1 eq.) is mixed with acetic anhydride (2.16 ml; 22.90 mmol; 12.40 eq.). The tube is sealed and is heated at 150° C. with an oil bath. After 15 min, the mixture becomes yellow. The reaction is complete. The solvents are removed and N-(5-acetyl-4-methyl-1,3-thiazol-2-yl)-N-pyrazin-2-ylacetamide is used as such without further purification (510.3 mg; quantitative).

Step IV: 2-bromo-1-[4-methyl-2-(pyrazin-2-ylamino)-1,3-thiazol-5-yl]ethanone, hydrobromide salt (Intermediate 3)

N-(5-acetyl-4-methyl-1,3-thiazol-2-yl)-N-pyrazin-2-ylacetamide (511.2 mg; 1.85 mmol; 1 eq.) is dissolved in AcOH (10 ml). Hydrobromic acid (32 µl; 0.19 mmol; 0.10 eq.) is added, followed by a solution of bromine (95 µl; 1.85 mmol; 1 eq.) in AcOH (2 ml). The mixture is stirred 3 h at rt and 2 h at 60° C. To complete the reaction, bromine (95 µl; 1.85 mmol; 1 eq.) is added and the mixture is stirred 4 h at 60° C. Solvents are evaporated and the resulting dark brown solid is suspended in THF, filtered and washed with cyclohexane, affording Intermediate 3 as yellow solid (467.7 mg; 64%). It is used in bisthiazol synthesis as HBr salt or as parent, after 5 min treatment with Amberlyst A21 in DCM/MeOH mixture. $^1$H NMR (DMSO-$d_6$, 300 MHz) δ 2.60 (s, 3H), 4.64 (s, 2H), 8.24 (d, J=2.6 Hz, 1H), 8.43 (dd, J=1.5 Hz, J=2.6 Hz, 1H), 8.50 (d, J=1.5 Hz, 1H). M$^+$ (ESI): 312.9. HPLC (Method A), Rt: 2.80 min (purity: 97%).

Intermediate 4: Preparation of 1-{2-[(1-acetyl-1H-pyrazol-3-yl)amino]-4-methyl-1,3-thiazol-5-yl}-2-bromoethanone, hydrobromide salt (Intermediate (P1) wherein R$^4$ is 1-acetyl-1H-pyrazol-3-yl, R$^2$ is H, R$^3$ is methyl and X is S)

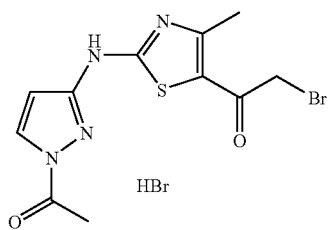

Intermediate 4

Step I: Preparation of N-1H-Pyrazol-3-ylthiourea

To a solution of ammonium thiocyanate (17.8 g, 0.234 mol) in dry acetone (200 ml) at 0° C. under nitrogen is added benzoylchloride (30 g, 0.213 mol) over a period of 15 min. The reaction mixture is stirred at rt for 30 min and filtered. To the filtrate is added 3-aminopyrazole (14.1 g, 0.17 mol) dropwise and stirred 3 h at room temperature. The solvents are removed under vacuum and the residue is purified by flash chromatography using chloroform/methanol (9/1) as eluent. N-[(1H-pyrazol-3-ylamino)carbonothioyl]benzamide is isolated as a solid (22 g; 52%). M$^+$ (ESI): 246.9. TLC—Chloroform/methanol (9/1): $R_f$–0.45.

A solution of N-[(1H-pyrazol-3-ylamino)carbonothioyl] benzamide (22 g, 0.089 mol) in 10% NaOH solution (200 ml) is stirred at 80° C. for 45 min. The reaction mixture is cooled down to rt and the solvents are removed under vacuum. The residue is acidified with 2M HCl to pH=1 and then basified with ammonium hydroxide. The product is extracted with dichloromethane (4×100 ml). The combined extracts are dried and evaporated. The solid residue is purified by flash chromatography using chloroform/methanol (9/1) as eluent. N-1H-Pyrazol-3-ylthiourea is isolated as a solid (9 g; 75%). $^1$H NMR (DMSO-$d_6$, 300 MHz): δ 5.88 (br s, 1H), 7.64 (s, 1H), 8.44 (br s, 1H), 9.02 (br s, 1H), 10.30 (br s, 1H), 12.47 (br s, 1H). HPLC (Method B), Rt: 3.88 min (purity: 99.4%). TLC: Chloroform/methanol (9/1): $R_f$–0.2. Mp: 130-132° C.

Step II: Preparation of 1-[4-Methyl-2-(1H-pyrazol-3-ylamino)-1,3-thiazol-5-yl]ethanone To a solution of N-1H-pyrazol-3-ylthiourea (5 g, 0.0352 mol) in absolute ethanol (50 ml) is added 3-chloro-2,4-pentanedione (4.78 g, 0.0352 mol) and the mixture is refluxed for 20 h under nitrogen. The reaction mixture is cooled down to rt and the resulting precipitate is filtered, washed with ethanol (25 ml) and dried under suction to afford the desired product as hydrochloride salt. It is neutralized with 10% solution of sodium bicarbonate, filtered and dried to afford 1-[4-Methyl-2-(1H-pyrazol-3-ylamino)-1,3-thiazol-5-yl]ethanone as pale brown solid (5 g, 64%). $^1$H NMR (CD$_3$OD, 300 MHz): δ 2.49 (s, 3H), 2.61 (s, 3H), 6.14 (br s, 1H), 7.62 (br s, 1H). HPLC (Method B), Rt: 4.31 min (purity: 98.07%). TLC—Chloroform/methanol (8/2): $R_f$ 0.4. Mp: 224-227° C.

Step III: N-(5-acetyl-4-methyl-1,3-thiazol-2-yl)-N-(1-acetyl-1H-pyrazol-3-yl)acetamide In a tube, 1-[4-Methyl-2-(1H-pyrazol-3-ylamino)-1,3-thiazol-5-yl]ethanone (500 mg; 2.25 mmol; 1 eq.) is mixed with acetic anhydride (2.64 ml; 27.89 mmol; 12.40 eq.). The tube is sealed and is heated at 150° C. with an oil bath. After 10 min, the reaction is complete. The solvents are evaporated, affording N-(5-acetyl-4-methyl-1,3-thiazol-2-yl)-N-(1-acetyl-1H-pyrazol-3-yl)acetamide which is used in the next step without further purification (689.1 mg; quantitative).

Step IV: 1-{2-[(1-acetyl-1H-pyrazol-3-yl)amino]-4-methyl-1,3-thiazol-5-yl}-2-bromoethanone, hydrobromide salt (Intermediate 4)

N-(5-acetyl-4-methyl-1,3-thiazol-2-yl)-N-(1-acetyl-1H-pyrazol-3-yl)acetamide (689.3 mg; 2.25 mmol; 1 eq.) is dissolved in AcOH (10 ml) and hydrobromic acid (39 µl; 0.22 mmol; 0.10 eq.). A solution of bromine (115 µl; 2.25 mmol; 1 eq.) in AcOH (2 ml) is added dropwise. The reaction mixture is stirred 3 h at rt and 2 h at 60° C. In order to complete the reaction, a solution of bromine (58 μl; 1.12 mmol; 0.50 eq.) in AcOH (2 ml) is added and the mixture is stirred 4 h at 60° C. It is cooled down to rt and the resulting precipitate is filtered, washed with cyclohexane and dried under reduced pressure to give, affording Intermediate 4 (695.7 mg; 73%). It is used in bis-thiazol synthesis as HBr salt or as parent, after 5 min treatment with Amberlyst A21 in DCM/MeOH mixture. $^1$H NMR (DMSO-$d_6$, 300 MHz) δ 2.57 (s, 3H), 2.64 (s, 3H), 4.63 (s, 2H), 6.36 (d, J=6 Hz, 1H), 8.35 (d, J=6 Hz, 1H). M$^-$ (ESI): 342.96; M$^+$ (ESI): 344.94. HPLC (Method A), Rt: 3.08 min (purity: 91.91%).

Intermediate 5: Preparation of (2-Amino-4-methyl-[4,5]bisthiazolyl-2-yl)acetonitrile

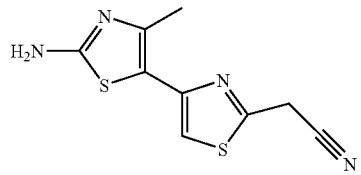

Intermediate 5

To a solution of 1-(2-amino-4-methyl-1,3-thiazol-5-yl)-2-bromo-ethanone, hydrobromide salt Intermediate 2 (5340 mg; 16.9 mmol; 1 eq) in ethanol (150 ml), is added 2-cyanothioacetamide (1692.2 mg; 16.9 mmol; 1 eq). The reaction mixture is stirred at RT for 20 h. The precipitate formed is filtered off affording Intermediate 5 as an orange solid (4400 mg; quantitative yield). It is used in the next step without further purification. 1H NMR (DMSO-$d_6$, 300 MHz) δ 2.40 (s, 3H), 4.61 (s, 2H), 7.83 (s, 1H), 9.05 (s, 2H), M$^-$ (ESI): 235.13; M$^+$ (ESI): 237.06. HPLC (method A), Rt: 1.30 min (purity: 97.79%).

Intermediate 6: Preparation of N-[2-cyanomethyl)-4'-methyl-4,5'-bi-1,3-thiazol-2'-yl]-1H-imidazole-1-carboxamide

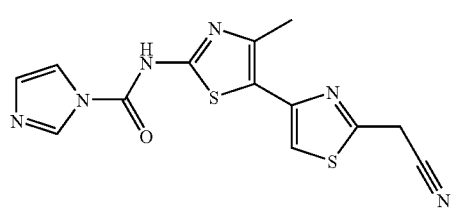

Intermediate 6

In a 250 ml flask under Ar, triethylamine (0.65 ml; 4.69 mmol; 1.49 eq.) is added to a stirred suspension of Intermediate 5 (1 000 mg; 3.15 mmol; 1 eq.) and CDI (1 372 mg; 8.46 mmol; 2.68 eq.) in dry DCM (65 ml). DMF (4 ml) is added to help the solubility. The mixture is stirred at 45° C. overnight. No starting material can be detected by HPLC. The reaction mixture is cooled down to RT. The resulting precipitate is isolated by filtration, washed with diethyl ether and dried under vacuum, affording Intermediate 6 (822.8 mg; 79%). It is used in the next step without further purification.

Intermediate 7: Preparation of N-[4'-methyl-2-morpholin-4-ylcarbonyl)-4,5'-bi-1,3-thiazol-2'-yl]-1H-imidazole-1-carboxamide

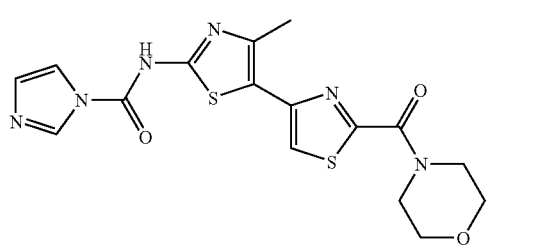

Intermediate 7

Step I: Ethyl 2'-amino-4'-methyl-4,5'-bi-1,3-thiazole-2-carboxylate

In a 20 ml microwave vial, Intermediate 2 (400 mg; 1.27 mmol; 1 eq.) is suspended in EtOH (7 ml). Ethyl thiooxamate (168.6 mg; 1.27 mmol; 1 eq.) is added and the mixture is heated under microwave irradiation at 120° C. for 15 min. The reaction mixture is filtered to give the HBr salt of the title compound (201 mg; 45%). The compound is suspended in 2:1 DCM/EtOH (9 ml) and Amberlyst A-21 (200 mg; 4.54 mmol; 3.58 eq.) is added. After 2h30 shaking at RT, the mixture is filtered and the resin is rinsed with DCM and EtOH, affording ethyl 2'-amino-4'-methyl-4,5'-bi-1,3-thiazole-2-carboxylate which is used in the next step without further purification (146.2 mg; 43%).

$^1$H NMR (DMSO-$d_6$, 300 MHz) δ 1.30 (t, J=9 Hz, 3H), 2.32 (s, 3H), 4.38 (q, J=9 Hz, 2H), 7.17 (br s, 2H), 7.82 (s, 1H). M$^-$ (ESI): 268.17; M$^+$ (ESI): 270.16. HPLC (method A), Rt: 1.83 min (purity: 99.31%).

Step II: 4'-methyl-2-(morpholin-4-ylcarbonyl)-4,5'-bi-1,3-thiazol-2'-amine

To ethyl 2'-amino-4'-methyl-4,5'-bi-1,3-thiazole-2-carboxylate, obtained in step I, as describe above (188 mg; 0.70 mmol; 1 eq.) is added morpholine (6 ml) in a 5-10 ml microwave vial. The resulting solution is heated under microwave irradiation at 130° C. for 60 min. Morpholine is removed under reduce pressure and the crude product is purified by preparative HPLC, affording 4'-methyl-2-(morpholin-4-ylcarbonyl)-4,5'-bi-1,3-thiazol-2'-amine as TFA salt (171.7 mg; 58%).

$^1$H NMR (DMSO-$d_6$, 300 MHz) δ 2.36 (s, 3H), 3.67 (m, 6H), 4.28 (m, 2H), 7.94 (s, 1H), 8.27 (br s, 2H). M$^-$ (ESI): 309.04; M$^+$ (ESI): 311.09. HPLC (method A), Rt: 1.54 min (purity: 99.57%).

Step III: N-[4'-methyl-2-(morpholin-4-ylcarbonyl)-4,5'-bi-1,3-thiazol-2'-yl]-1H-imidazole-1-carboxamide (Intermediate 7)

In a 20 ml vial under Ar, triethylamine (51 μl; 0.37 mmol; 1.10 eq.) is added to a stirred suspension of 4'-methyl-2-(morpholin-4-ylcarbonyl)-4,5'-bi-1,3-thiazol-2'-amine, obtained in step II as describe above (142.4 mg; 0.34 mmol; 1 eq.), and CDI (54.4 mg; 0.34 mmol; 1 eq.) in dry DCM (5 ml). DMF (0.30 ml) is added to help the solubility. The mixture is stirred at 45° C. overnight. No starting material can be detected by HPLC. The reaction mixture is cooled down to RT. The resulting precipitate is isolated by filtration, washed with diethyl ether and dried under vacuum, affording Intermediate 7 (107.1 mg; 79%). It is used in the next step without further purification.

Amine 1: Preparation of 6-Amino-2,2-dimethyl-benzo[1,3]dioxin-4-one

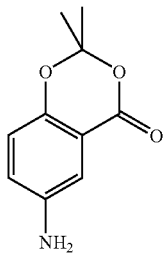

Amine 1

Step I: 6-[hydroxy(oxido)amino]-2,2-dimethyl-4H-1,3-benzodioxin-4-one

2-Hydroxy-5-nitro-benzoique acid (Aldrich) is suspended in TFA (900 ml) and trifluoroacetic anhydride (300 ml). Acetone is added in portions over 15 min (300 ml). The mixture is slowly heated up to 100° C. during 45 min. The solvents are evaporated, the resulting crude product is dissolved in AcOEt, washed with a saturated solution of $NaHCO_3$ (250 ml) and brine, and dried over $MgSO_4$. After evaporation of the solvents, the desired product is crystallized in $AcOEt/Et_2O$/heptane. It is filtrated, washed with heptane and dried under vacuo, affording 6-[hydroxy(oxido)amino]-2,2-dimethyl-4H-1,3-benzodioxin-4-one as a beige solid (152.2 g; 82%). HPLC (method A), Rt: 2.94 min (purity: 99.86%).

Step II: 6-amino-2,2-dimethyl-4H-1,3-benzodioxin-4-one (6-amino-2,2-dimethyl-4H-1,3-benzodioxin-4-one (Amine 1)

In an autoclave, 6-[hydroxy(oxido)amino]-2,2-dimethyl-4H-1,3-benzodioxin-4-one (75.0 g) is dissolved in AcOEt (250 ml) and MeOH (80 ml). Under Argon, Pd/C 10% (2.8 g) is added. The reaction mixture is put under hydrogen atmosphere (10 bars). As the reaction is exothermic, the reactor is cooled down with an ice bath. After 30 min, the reduction is complete. The solution is filtered on Celite and concentrated. The resulting solid is filtered, washed with pentane and dried under vacuo, affording Amine 1 as yellow solid (58.2 g; 90%). $^1$H NMR (DMSO-$d_6$, 300 MHz) δ 1.61 (s, 6H), 5.15 (br s, 2H), 6.80 (d, J=9 Hz, 1H), 6.88 (dd, J=9 Hz, J=3 Hz, 1H), 7.01 (d, J=3 Hz, 1H). M$^+$ (ESI): 194. HPLC (method A), Rt: 1.93 min (purity: 99.52%).

Amine 2: Preparation of 5-(3-aminophenyl)-1,3,4-thiadiazol-2-amine

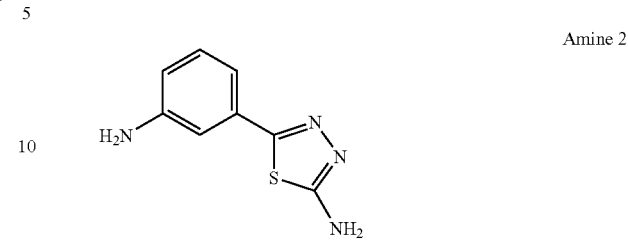

Amine 2

Thiosemicarbazide (455.7 mg; 5 mmol; 1 eq.) and 3-aminobenzonitrile (Aldrich)(590.7 mg; 5 mmol; 1 eq.) are heated in TFA (2.50 ml) at 60° C. for 4 hours. The mixture becomes a thick yellowish solution. The reaction mixture is poured into ice-water (15 ml) and neutralized with saturated $NaHCO_3$ aqueous solution. The resulting precipitate is filtered, affording 5-(3-aminophenyl)-1,3,4-thiadiazol-2-amine, Amine 2, as white-off solid (291 mg; 30%).

Amine 3: Preparation of 7-Amino-2,2-dimethyl-4H-1,3-benzodioxine-4-one

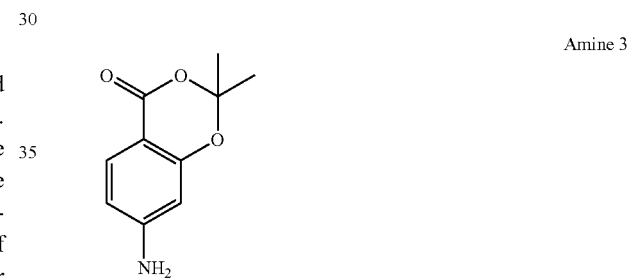

Amine 3

Step I: 4-{([(benzyloxy)carbonyl]amino}-2-hydroxy benzoic acid

To a solution of sodium-p-aminosalicylate (Aldrich)(100 g, 0.65 mol) in 10% aqueous NaOH solution (1000 ml) is added 50% wt solution of benzylchloroformate (670 g, 1.96 mol in toluene) at 0° C. The resulting mixture is stirred at rt for 48 h. The progression of the reaction is followed by NMR. The reaction mixture is cooled down to 0° C. and acidified with 10% aqueous HCl. The solid obtained is filtered and washed with cold water and dried. It is further treated with petroleum ether and filtered to give crude 4-{[(benzyloxy)carbonyl]amino}-2-hydroxy benzoic acid (128 g, 68%).

Step II: 7-N-Cbz-amino-2,2-dimethyl-4H-1,3-benzodioxin-4-one

To a suspension of 4-{[(benzyloxy)carbonyl]amino}-2-hydroxy benzoic acid (25 g, 0.087 mol) in TFA (108 ml) is added trifluoroacetic anhydride (TFAA, 35 ml, 0.249 mol) at rt with stirring. Dry acetone (60 ml) is added in portions, over 4 h interval, and the reaction mixture is heated at 60° C. for 24 h. Excess TFA and TFAA are removed under vacuum and the resulting crude product is purified by flash chromatography over silica gel (treated with triethylamine) with CH$_2$Cl$_2$ as eluent. Two products are isolated, 7-N-Cbz-amino-2,2-dimethyl-4H-1,3-benzodioxin-4-one (3.5 g) and 7-amino-2,2-dimethyl-4H-1,3-benzodioxin-4-one (1.6 g).

Step III:
7-amino-2,2-dimethyl-4H-1,3-benzodioxin-4-one
(Amine 3)

In an autoclave, Pd/C (350 mg) is added to a solution of 7-N-Cbz-amino-2,2-dimethyl-4H-1,3-benzodioxin-4-one (3.5 g) in methanol (250 ml). The reaction mixture is put under hydrogen atmosphere (10 bars) and is stirred 24 h at rt. The reaction mixture is filtered over Celite and concentrated, affording 7-amino-2,2-dimethyl-4H-1,3-benzodioxin-4-one (1.6 g). An overall yield of 20% is obtained for these three steps. $^1$H NMR (DMSO-d$_6$, 300 MHz) δ 1.60 (s, 6H), 6.03 (d, J=2 Hz, 1H), 6.30 (dd, J=8 Hz, J=2 Hz, 1H), 6.36 (br s, 2H), 7.45 (d, J=8 Hz, 1H). M$^-$ (ESI): 192; M$^+$ (ESI): 194. HPLC (method A), Rt: 0.95 min (purity: 100%).

Amine 4: Preparation of
5-(3-aminophenyl)-1,3,4-oxadiazol-2-ol

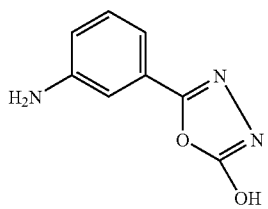

Amine 4

Step I: Methyl 3-nitrobenzoate

3-Nitrobenzoic acid (Aldrich)(1 g; 5.98 mmol; 1 eq.) is dissolved in toluene (15 ml). Timethylsilyl diazomethane in toluene and MeOH (1/1)(9.0 ml; 2 M; 17.95 mmol; 3 eq.) is added dropwise. The solution is stirred at rt for 1.5 h. Solvents are removed affording methyl 3-nitrobenzoate as a yellow powder (940.7 mg; 87%).
$^1$H NMR (DMSO-d$_6$) δ: 3.92 (s, 3H), 7.84 (m, 1H), 8.35 (m, 1H), 8.50 (m, 1H), 8.62 (m, 1H). HPLC (method A), Rt: 1.8 min (purity: 99.1%).

Step II: 3-Nitrobenzohydrazide

Methyl 3-nitrobenzoate (940.7 mg; 5.19 mmol; 1 eq.) is dissolved in EtOH (24 ml). Hydrazine hydrate (4.04 ml; 83.09 mmol; 16 eq.) is added and the mixture is stirred 1 hour at rt. It is stirred at 60° C. for 6 hours and rt overnight. The precipitate formed is filtrated and dried under vacuo, affording 3-nitrobenzohydrazide as white-off solid (815.9 mg; 87%).
$^1$H NMR (DMSO-d$_6$) δ: 4.62 (s, 2H), 7.76 (m, 1H), 8.24 (m, 1H), 8.36 (m, 1H), 8.63 (s, 1H), 10.15 (s, 1H).

Step III: 5-(3-nitrophenyl)-1,3,4-oxadiazol-2-ol 1,1'-Carbonyldiimidazole (641.2 mg; 3.95 mmol; 1 eq.) is added to a 0° C. solution of 3-nitrobenzohydrazide (715.9 mg; 3.95 mmol; 1 eq.) and triethylamine (822 µl; 5.93 mmol; 1.50 eq.) in DMF (30 ml). The reaction mixture is stirred between 0° C. and rt for 4 hours. Solvents are removed under vacuo affording an orange oil which is solubilized in DCM and washed with HCl 0.1 M. The organic phase is concentrated. The resulting precipitate is recovered by filtration, affording 5-(3-nitrophenyl)-1,3,4-oxadiazol-2-ol as a white solid (469.9 mg; 58%). $^1$H NMR (DMSO-d$_6$) δ: 7.84 (s, 1H), 8.19 (m, 1H), 8.41 (m, 2H), 12.91 (s, 1H). HPLC (method A), Rt: 2.06 min (purity: 97.5%).

Step IV: 5-(3-aminophenyl)-1,3,4-oxadiazol-2-ol
(Amine 4)

In a flask, is dissolved 5-(3-nitrophenyl)-1,3,4-oxadiazol-2-ol (369.9 mg; 1.79 mmol; 1 eq.) in MeOH (20 ml) under innert atmosphere. Palladium 10% on charcoal (190 mg; 0.18 mmol; 0.10 eq.) is added and the reaction mixture is stirred 5 minutes at rt. The mixture is then put under atmospheric pressure of hydrogen. The reaction is completed after 2 hours. The mixture is filtrated on celite and rinced with MeOH. The solvents are evaporated under vacuo, affording Amine 4 as a white powder (283.3 mg; 90%).
$^1$H NMR (DMSO-d$_6$) δ: 5.43 (s, 2H), 6.70 (m, 1H), 6.89 (m, 1H), 7.08 (s, 1H), 7.14 (m, 1H), 12.44 (s, 1H).

Amine 5: Preparation of
5-(4-aminophenyl)-1,3,4-oxadiazol-2-ol

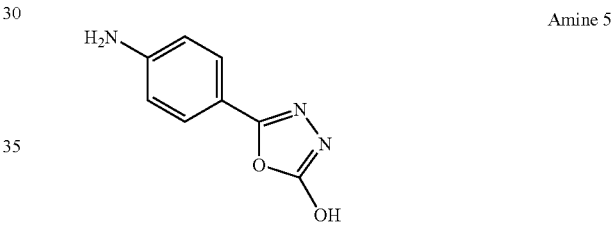

Amine 5

Step I: Methyl 4-nitrobenzoate

4-Nitrobenzoic acid (5 g; 29.92 mmol; 1 eq.) is dissolved in toluene (37.5 ml). Timethylsilyl diazomethane in toluene and MeOH (1/1)(45 ml; 2 M; 89.76 mmol; 3 eq.) is added dropwise. The solution is stirred at rt for 2 h. Solvents are removed affording methyl 4-nitrobenzoate as a yellow powder (5.42 g; 100%).
$^1$H NMR (DMSO-d$_6$) δ: 3.90 (s, 3H), 8.19 (d, J=9 Hz, 2H), 8.34 (d, J=9 Hz, 2H). HPLC, (method A), Rt: 2.66 min (purity: 98.7%).

Step II: 3-Nitrobenzohydrazide

Methyl 4-nitrobenzoate (5.42 g; 29.92 mmol; 1 eq.) is dissolved in EtOH (120 ml). Hydrazine hydrate (7.27 ml; 149.60 mmol; 5 eq.) is added and the mixture is stirred 1 hour at rt. It is stirred at 60° C. for 6 hours and rt overnight. The precipitate formed is filtrated and dried under vacuo, affording 4-nitrobenzohydrazide as white-off solid (4.31 g; 79%).
$^1$H NMR (DMSO-d$_6$) δ: 4.63 (s, 2H), 8.03 (d, J=9 Hz, 2H), 8.23 (d, J=9 Hz, 2H), 10.12 (s, 1H). HPLC (method A), Rt: 0.78 min (purity: 100.0%).

Step III: 5-(4-nitrophenyl)-1,3,4-oxadiazol-2-ol 1,1'-Carbonyldiimidazole (3.86 g; 23.81 mmol; 1 eq.) is added to a 0° C. solution of 4-nitrobenzohydrazide (4.31 g;

23.81 mmol; 1 eq.) and triethylamine (4.95 ml; 35.71 mmol; 1.50 eq.) in DMF (150 ml). The reaction mixture is stirred between 0° C. and rt for 3.5 hours. Solvents are removed under vacuo affording an orange oil which is solubilized in DCM and washed with HCl 0.1 M. The organic phase is concentrated. The resulting precipitate is recovered by filtration, affording 5-(4-nitrophenyl)-1,3,4-oxadiazol-2-ol as a white solid (4.50 g; 91%).

$^1$H NMR (DMSO-$d_6$) δ: 8.02 (d, J=9 Hz, 2H), 8.34 (d, J=9 Hz, 2H), 12.92 (s, 1H). M$^-$ (ESI): 206.3. HPLC (method A), Rt: 2.09 min (purity: 98.2%).

Step IV: 5-(4-aminophenyl)-1,3,4-oxadiazol-2-ol (Amine 5)

In a flask, is dissolved 5-(4-nitrophenyl)-1,3,4-oxadiazol-2-ol (4.50 g; 21.72 mmol; 1 eq) in MeOH (150 ml) under inert atmosphere. Palladium 10% on charcoal (2.31 g; 2.17 mmol; 0.10 eq.) is added and the reaction mixture is stirred 5 minutes at rt. The mixture is then put under atmospheric pressure of hydrogen. The reaction is completed after 2 hours. The mixture is filtrated on celite and rinced with MeOH. The solvents are evaporated under vacuo, affording 5-(4-aminophenyl)-1,3,4-oxadiazol-2-ol as a white powder (2.34 g; 61%).

$^1$H NMR (DMSO-$d_6$) δ: 5.84 (s, 2H), 6.62 (d, J=9 Hz, 1H), 7.62 (d, J=9 Hz, 1H), 12.15 (s, 1H).

Amine 6: Preparation of N,N-diisopropyl-beta-alaninamide

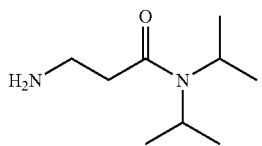

Amine 6

Step I: N~3~-(tert-butoxycarbonyl)-N,N-diisopropyl-beta-alaninamide

To a mixture of diisopropylamine (280 µl; 1.99 mmol; 1 eq) and boc-beta-alanine (414.7 mg; 2.19 mmol; 1.10 eq) in DCM (30 ml), are added triethylamine (829 µl; 5.98 mmol; 3 eq) and 2-chloro-1-methylpyridinium iodide (1 527 mg; 5.98 mmol; 3 eq). The mixture is stirred for 2 days at RT. The reaction is followed by TLC (cyclohexane/EtOAc 1:1). The reaction mixture is then washed twice with NH$_4$Cl sat. solution and twice with NaHCO$_3$ sat. solution. The organic layers are dried over Na$_2$SO$_4$, filtered and concentrated to give 760 mg of an orange oil, which is purified by flash chromatography (cyclohexane/EtOAc gradient, from 9/1 to 1/1 over 30 min). The title compound is isolated as a slightly yellow solid (511.2 mg; 94%).

$^1$H NMR (DMSO-$d_6$, 300 MHz) δ 1.16 (d, J=6 Hz, 6H), 1.35 (d, J=9 Hz, 6H), 1.40 (s, 9H), 2.44 (t, J=6 Hz, 2H), 3.37 (t, J=6 Hz, 2H), 3.47 (m, 1H), 3.89 (sept, J=6 Hz, 1H), 5.05 (br s, 1H). M$^+$ (ESI): 273.33.

Step II: N,N-diisopropyl-beta-alaninamide (Amine 6)

N~3~-(tert-butoxycarbonyl)-N,N-diisopropyl-beta-alaninamide, obtained in step I as describe above (100 mg; 0.37 mmol; 1 eq), is dissolved in DCM (3.20 ml). Trifluoroacetic acid (0.80 ml) is added at RT. After 20 min the reaction is complete (reaction followed by TLC: cyclohexane/ethyl acetate 1:1) and the solvents are evaporated. DCM (5 ml) is added and evaporated twice, affording Amine 6 as colorless oil (105 mg, quantitative yield).

$^1$H NMR (DMSO-$d_6$, 300 MHz) δ 1.21 (d, J=6 Hz, 6H), 1.34 (d, J=6 Hz, 6H), 2.75 (m, 2H), 3.32 (m, 2H), 3.53 (m, 1H), 3.87 (sept., 1H), 7.70 (br s, 3H).

Amine 7: Preparation of N-(2-hydroxy-1,1-dimethylethyl)-beta-alaninamide

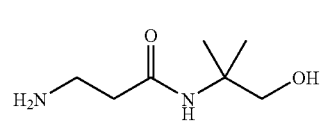

Amine 7

Step I: N~3~-(tert-butoxycarbonyl)-N-(2-hydroxy-1,1-dimethylethyl)-beta-alaninamide To a mixture of 2-amino-2-methyl-1-propanol (177.4 mg; 1.99 mmol; 1 eq) and boc-beta-alanine (338.9 mg; 1.79 mmol; 0.9 eq) in DCM (30 ml), are added triethylamine (0.83 ml; 5.97 mmol; 3 eq) and 2-chloro-1-methylpyridinium iodide (1525 mg; 5.97 mmol; 3 eq). The mixture is stirred for 2 days at RT. The reaction is followed by TLC (cyclohexane/EtOAc 1:1). The reaction mixture is then washed twice with NH$_4$Cl sat. solution and twice with NaHCO$_3$ sat. solution. The organic layer is dried over Na$_2$SO$_4$, filtered and concentrated to give 592 mg of an orange oil, which is purified by flash chromatography (cyclohexane/EtOAc gradient, from 9/1 to 1/1 over 30 min). The title compound is isolated as a slightly yellow solid (331.1 mg; 64%).

$^1$H NMR (DMSO-$d_6$, 300 MHz) δ 1.28 (s, 6H), 1.42 (s, 9H), 2.41 (m, 2H), 3.37 (m, 2H), 3.57 (s, 2H), 5.99 (br s, 1H).

Step II: N-(2-hydroxy-1,1-dimethylethyl)-beta-alaninamide (Amine 7)

N~3~-(tert-butoxycarbonyl)-N-(2-hydroxy-1,1-dimethylethyl)-beta-alaninamide, obtained in step I as describe above (100 mg; 0.38 mmol; 1 eq), is dissolved in DCM (3.2 ml). Trifluoroacetic acid (0.8 ml) is added at RT. After 20 min, the reaction is complete (TLC cyclohexane/ethyl acetate 1:1) and the solvents are removed. DCM is added (5 ml) and evaporated twice, affording Amine 7 as a colorless oil (105 mg, quantitative yield).

Amine 8: Preparation of N-(tert-butyl)-beta-alaninamide

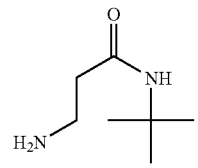

Amine 8

Step I: N~3~-(tert-butoxycarbonyl)-N-(tert-butyl)-beta-alaninamide

To a mixture of tert-butylamine (210 μl; 2 mmol; 1 eq) and boc-beta-alanine (416.3 mg; 2.20 mmol; 1.10 eq) in DCM (30 ml), are added triethylamine (832 μl; 6 mmol; 3 eq) and 2-chloro-1-methylpyridinium iodide (1 533 mg; 6 mmol; 3 eq). The mixture is stirred overnight at RT. The reaction is followed by TLC (cyclohexane/EtOAc 1:1). The reaction mixture is then washed twice with NH₄Cl sat. solution and twice with NaHCO₃ sat. solution. The organic layer is dried over Na₂SO₄, filtered and concentrated, to give 639 mg of an orange oil which is purified by flash chromatography (cyclohexane/EtOAc gradient, from 9/1 to 1/1 over 30 min). The title product is isolated as a slightly yellow solid (467.7 mg; 96%).

$^1$H NMR (DMSO-d$_6$, 300 MHz) δ 1.32 (s, 9H), 1.41 (s, 9H), 2.30 (t, J=6 Hz, 2H), 3.35 (t, J=6 Hz, 2H), 5.13 (br s, 1H), 5.44 (br s, 1H). M$^+$ (ESI): 245.3.

Step II: N-(tert-butyl)-beta-alaninamide (Amine 8)

N~3~-(tert-butoxycarbonyl)-N-(tert-butyl)-beta-alaninamide, obtained in step I as describe above (100 mg; 0.41 mmol; 1 eq), is dissolved in DCM (3.2 ml). Trifluoroacetic acid (0.80 ml) is added at RT. After 20 min the reaction is complete (TLC cyclohexane/ethyl acetate 1:1) and the solvents are evaporated. DCM is added and evaporated twice, affording Amine 8 as a colorless oil (105 mg, quantitative yield).

Amine 9: Preparation of 3-(2,2-dimethyl-1,3-thiazolidin-3-yl)-3-oxopropan-1-amine

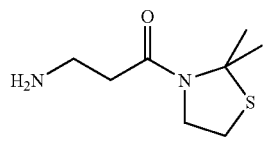

Amine 9

Step I: tert-butyl [3-(2,2-dimethyl-1,3-thiazolidin-3-yl)-3-oxopropyl]carbamate To a mixture of 2,2-dimethylthiazolidine (234.4 mg; 2 mmol; 1 eq) and boc-beta-alanine (416.3 mg; 2.20 mmol; 1.10 eq) in DCM (30 ml), are added triethylamine (832 μl; 6 mmol; 3 eq) and 2-chloro-1-methylpyridinium iodide (1533 mg; 6 mmol; 3 eq). The mixture is stirred 2 days at RT. The reaction is followed by TLC (cyclohexane/EtOAc 1:1). The reaction mixture is then washed twice with NH₄Cl sat. solution and twice with NaHCO₃ sat. solution. The organic layer is dried over Na₂SO₄, filtered and concentrated to give 497 mg of an orange oil, which is purified by flash chromatography (cyclohexane/EtOAc gradient, from 9/1 to 1/1 over 30 min). The title product is isolated as a white-off solid (45.5 mg; 8%).

$^1$H NMR (DMSO-d$_6$, 300 MHz) δ 1.42 (s, 9H), 1.81 (s, 6H), 2.45 (t, J=6 Hz, 2H), 2.97 (t, J=6 Hz, 2H), 3.38 (m, 2H), 3.82 (t, J=6 Hz, 2H), 5.21 (br s, 1H). M$^+$ (ESI): 289.2.

Step II: 3-(2,2-dimethyl-1,3-thiazolidin-3-yl)-3-oxopropan-1-amine (Amine 9)

Tert-butyl [3-(2,2-dimethyl-1,3-thiazolidin-3-yl)-3-oxopropyl]carbamate, obtained in step I as describe above (43.3 mg; 0.15 mmol; 1 eq), is dissolved in DCM (1.60 ml). Trifluoroacetic acid (0.40 ml) is added at RT. After 20 min, the reaction is complete (TLC cyclohexane/ethyl acetate), and the solvents are evaporated. DCM (5 ml) is added, and evaporated twice, affording Amine 9 as a colorless oil (45 mg, quantitative yield).

Amine 10: Preparation of 3-(4,4-dimethyl-1,3-oxazolidin-3-yl)-3-oxopropan-1-amine

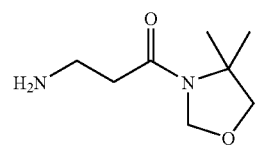

Amine 10

Step I: tert-butyl [3-(4,4-dimethyl-1,3-oxazolidin-3-yl)-3-oxopropyl]carbamate To a mixture of 4,4-dimethyloxazolidine (287 μl; 2 mmol; 1 eq) and boc-beta-alanine (416.3 mg; 2.2 mmol; 1.10 eq) in DCM (30 ml), are added triethylamine (832 μl; 6 mmol; 3 eq) and 2-chloro-1-methylpyridinium iodide (1533 mg; 6 mmol; 3 eq). The mixture is stirred for 2 days at RT. The reaction is followed by TLC cyclohexane/EtOAc 1:1). The reaction mixture is then washed twice with NH₄Cl sat. solution and twice with NaHCO₃ sat. solution. The organic layer is dried over Na₂SO₄, filtered and concentrated to give 760 mg of an orange oil, which is purified by flash chromatography (cyclohexane/EtOAc gradient, from 9/1 to 1/1 over 30 min). The title product is isolated as a white-off solid (420.5 mg; 77%).

$^1$H NMR (DMSO-d$_6$, 300 MHz) δ 1.41 (s, 9H), 1.46 (s, 6H), 2.29 (t, J=6 Hz, 2H), 3.38 (t, J=6 Hz, 2H), 3.72 (s, 2H), 4.90 (s, 2H), 5.17 (br s, 1H). M$^+$ (ESI): 273.23.

Step II: 3-(4,4-dimethyl-1,3-oxazolidin-3-yl)-3-oxopropan-1-amine (Amine 10)

Tert-butyl [3-(4,4-dimethyl-1,3-oxazolidin-3-yl)-3-oxopropyl]carbamate, obtained in step I as describe above (100 mg; 0.37 mmol; 1 eq), is dissolved in DCM (3.20 ml). Trifluoroacetic acid (0.80 ml) is added at rt. After 20 min, the reaction is complete, (TLC cyclohexane/ethyl acetate 1:1) and the solvents are evaporated. DCM (5 ml) is added and evaporated twice, affording Amine 10 as a colorless oil (105 mg, quantitative yield).

Amine 11: Preparation of N-(2,2-dimethylpropyl)glycinamide

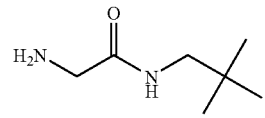

Amine 11

Step I: tert-butyl {2-[(2,2-dimethylpropyl)amino]-2-oxoethyl}carbamate

To a mixture of neopentylamine (174.3 mg; 2 mmol; 1 eq) and boc-glycine (385.4 mg; 2.20 mmol; 1.10 eq) in DCM (30 ml), are added triethylamine (832 µl; 6 mmol; 3 eq) and 2-chloro-1-methylpyridinium iodide (1533 mg; 6 mmol; 3 eq). The mixture is stirred overnight at RT. The reaction is followed by TLC (cyclohexane/EtOAc 1:1). The reaction mixture is then washed twice with NH$_4$Cl sat. solution and twice with NaHCO$_3$ sat. solution. The organic layer is dried over Na$_2$SO$_4$, filtered and concentrated to give 946 mg of an orange oil, which is purified by flash chromatography (cyclohexane/EtOAc gradient, from 9/1 to 1/1 over 30 min). The title product is isolated as a slightly yellow solid (96.7 mg; 20%).

$^1$H NMR (DMSO-d$_6$, 300 MHz) δ 0.89 (s, 9H), 1.44 (s, 9H), 3.06 (d, J=6 Hz, 2H), 3.76 (m, 2H), 5.11 (br s, 1H), 6.22 (br s, 1H). M$^-$ (ESI): 243.5; M$^+$ (ESI): 245.3.

Step II: N-(2,2-dimethylpropyl)glycinamide (Amine 11)

Tert-butyl {2-[(2,2-dimethylpropyl)amino]-2-oxoethyl}carbamate, obtained in step I as describe above (96.7 mg; 0.40 mmol; 1 eq), is dissolved in DCM (3.20 ml). Trifluoroacetic acid (0.80 ml) is added at RT. After 20 min the reaction is complete (TLC cyclohexane/ethyl acetate 1:1) and the solvents are evaporated. DCM is added and evaporated twice, affording Amine 11 as a colorless oil (102.2 mg, quantitative yield).

Amine 12: Preparation of 3-azocan-1-yl-3-oxopropan-1-amine

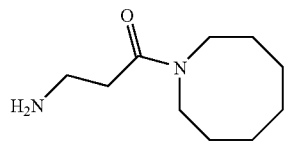

Amine 12

Step I: tert-butyl (3-azocan-1-yl-3-oxopropyl)carbamate

To a mixture of heptamethyleneimine (254 µl; 2 mmol; 1 eq) and boc-beta-alanine (416.3 mg; 2.20 mmol; 1.10 eq) in DCM (30 ml), are added triethylamine (832 µl; 6 mmol; 3 eq) and 2-chloro-1-methylpyridinium iodide (1533 mg; 6 mmol; 3 eq). The mixture is stirred overnight at RT. The reaction is followed by TLC (cyclohexane/EtOAc 1:1). The reaction mixture is then washed twice with NH$_4$Cl sat. solution and twice with NaHCO$_3$ sat. solution. The organic layer is dried over Na$_2$SO$_4$, filtered and concentrated to give 1.066 g of an orange oil, which is purified by flash chromatography (cyclohexane/EtOAc gradient, from 9/1 to 1/1 over 30 min). The title product is isolated as a slightly yellow solid (477 mg; 84%).

$^1$H NMR (DMSO-d$_6$, 300 MHz) δ 1.40 (s, 9H), 1.53 (m, 6H), 1.70 (m, 4H), 2.49 (t, J=6 Hz, 2H), 3.35 (t, J=6 Hz, 2H), 3.42 (quint, J=6 Hz, 4H), 5.32 (br s, 1H). M$^+$ (ESI): 285.4.

Step II: 3-azocan-1-yl-3-oxopropan-1-amine (Amine 12)

Tert-butyl (3-azocan-1-yl-3-oxopropyl)carbamate, obtained in step I as describe above (113.8 mg; 0.40 mmol; 1 eq), is dissolved in DCM (3.20 ml). Trifluoroacetic acid (0.80 ml) is added at RT. After 20 min, the reaction is complete (TLC cyclohexane/ethyl acetate) and the solvents are evaporated. DCM is added and evaporated twice, affording Amine 12 as a colorless oil (119 mg, quantitative yield).

Amine 13: Preparation of 2-(1-isopropyl-1H-imidazol-4-yl)ethanamine

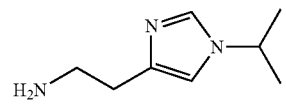

Amine 13

Step I: 7,8-dihydroimidazo[1,5-c]pyrimidin-5(6H)-one

A mixture of 2-(1H-imidazol-4-yl)ethanamine (26.8 g; 240.9 mmol; 1 eq) and CDI (39.1 g; 240.9 mmol; 1 eq) in DMF (401.7 ml) is stirred at 50° C. for two days. The mixture is concentrated to 100 ml and acetonitrile (200 ml) is added. The resulting precipitate is filtered, washed with acetonitrile (2×50 ml) and dried under vacuum, affording the title compound that is used in the next step without further purification (28.3 g; 85%).

$^1$H NMR (DMSO-d$_6$, 300 MHz) δ 2.87 (m, 2H), 3.34 (m, 2H), 6.78 (d, J=1 Hz, 1H), 8.04 (d, J=1 Hz, 1H), 8.19 (br s, 1H).

Step II: 2-isopropyl-5-oxo-5,6,7,8-tetrahydroimidazo[1,5-c]pyrimidin-2-ium iodide To a suspension of 7,8-dihydroimidazo[1,5-c]pyrimidin-5(6H)-one, obtained in step I as describe above (28.18 g; 205.5 mmol; 1 eq), in DMF (140.9 ml), is added 2-iodopropane (61.5 ml; 616.4 mmol; 3 eq). The reaction is stirred at RT, until a red suspension is obtained. The reaction mixture is concentrated and acetonitrile (200 ml) is added. The resulting precipitate is filtered, washed with acetonitrile (2×50 ml) and dried under vacuum, affording the title compound that is used in the next step without further purification (45.95 g, 73%).

$^1$H NMR (DMSO-d$_6$, 300 MHz) δ 1.49 (d, J=6.5 Hz, 6H), 3.02 (t, J=6.5 Hz, 2H), 3.48 (td, J=2.8 Hz, J=6.5 Hz, 2H), 4.72 (sept, J=6.5 Hz, 1H), 7.83 (d, J=1.5 Hz, 1H), 9.01 (br s, 1H), 9.76 (d, J=1.5 Hz, 1H).

Step III: 2-(1-isopropyl-1H-imidazol-4-yl)ethanamine (Amine 13)

A solution of 2-isopropyl-5-oxo-5,6,7,8-tetrahydroimidazo[1,5-c]pyrimidin-2-ium iodide, obtained in step II as describe above (41.12 g; 133.9 mmol; 1 eq.), in hydrochloric acid aqueous solution (411.2 ml; 6 M) is stirred at 10° C. for 3 days. Solvents are concentrated and acetonitrile (200 ml) is added. The resulting precipitate is filtered, washed with acetonitrile (2×50 ml) and dried under vacuum, affording Amine 13 that is used in the next step without further purification (18.6 g, 61%).

$^1$H NMR (DMSO-d$_6$, 300 MHz) δ 1.46 (d, J=6.5 Hz, 6H), 3.00 (t, J=6.5 Hz, 2H), 3.14 (m, 2H), 4.60 (sept, J=6.5 Hz, 1H), 7.76 (d, J=1.5 Hz, 1H), 8.23 (br s, 3H), 9.18 (d, J=1.5 Hz, 1H), 14.85 (br s, 1H). M$^+$ (ESI): 154.5.

Amine 14: Preparation of 2-(1-ethyl-1H-imidazol-4-yl)ethanamine

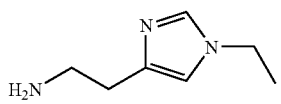

Amine 14

Step I: 7,8-dihydroimidazo[1,5-c]pyrimidin-5(6H)-one

A mixture of 2-(1H-imidazol-4-yl)ethanamine (26.8 g; 240.9 mmol; 1 eq) and CDI (39.1 g; 240.9 mmol; 1 eq) in DMF (402 ml) is stirred at 50° C. for two days. Solvents are concentrated to 100 ml and acetonitrile (200 ml) is added. The resulting precipitate is filtered, washed with acetonitrile (2×50 ml) and dried under vacuum, affording the title compound that is used in the next step without further purification (28.18 g; 85%).

$^1$H NMR (DMSO-d$_6$, 300 MHz) δ 2.87 (m, 2H), 3.34 (m, 2H), 6.78 (d, J=1 Hz, 1H), 8.04 (d, J=1 Hz, 1H), 8.19 (br s, 1H).

Step II: 2-ethyl-5-oxo-5,6,7,8-tetrahydroimidazo[1,5-c]pyrimidin-2-ium bromide A suspension of 7,8-dihydroimidazo[1,5-c]pyrimidin-5 (6H)-one, obtained in step I as describe above (500 mg; 3.65 mmol; 1 eq), and bromoethane (816 µl; 10.94 mmol; 3 eq) in DMF (7 ml) is divided in two equals fractions and heated under microwave irradiation at 180° C. for 20 min. The reaction mixtures are combined and acetonitrile (15 ml) is added. The resulting precipitate is filtered, washed with acetonitrile and dried under vacuum, affording the title compound that is used in the next step without further purification (118.3 mg; 13%).

$^1$H NMR (DMSO-d$_6$, 300 MHz) δ 1.43 (t, J=6 Hz, 3H), 3.01 (t, J=6 Hz, 2H), 3.47 (td, J=3 Hz, J=6 Hz, 2H), 4.24 (q, J=6 Hz, 2H), 7.70 (d, J=3 Hz, 1H), 9.02 (br s, 1H), 9.73 (d, J=3 Hz, 1H).

Step III: 2-(1-isopropyl-1H-imidazol-4-yl)ethanamine (Amine 14)

A solution of 2-ethyl-5-oxo-5,6,7,8-tetrahydroimidazo[1,5-c]pyrimidin-2-ium bromide, obtained in step II as describe above (118.6 mg; 0.48 mmol; 1 eq), in hydrochloric acid aqueous solution (5 ml; 5 M; 25 mmol; 52 eq) is stirred at 100° C. for 2 days. Sovents are then evaporated and acetonitrile (10 ml) is added. The resulting suspension is filtered, washed with acetonitrile and dried under vacuum, affording Amine 14 that is used in the next step without further purification (115.7 mg, quantitative yield).

$^1$H NMR (DMSO-d$_6$, 300 MHz) δ 1.40 (t, J=6 Hz, 3H), 2.98 (m, 2H), 3.11 (m, 2H), 4.15 (q, J=6 Hz, 2H), 7.65 (s, 1H), 8.13 (br s, 3H), 9.11 (s, 1H).

Amine 15: Preparation of 2-(5-tert-butyl-1,2,4-oxadiazol-3-yl)ethanamine

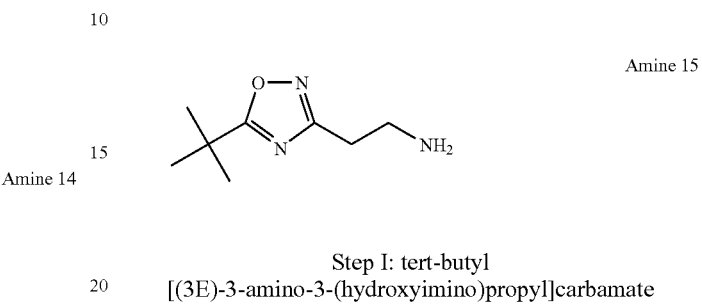

Amine 15

Step I: tert-butyl [(3E)-3-amino-3-(hydroxyimino)propyl]carbamate

Tert-butyl N-(2-cyanoethyl)carbamate (40 g; 235 mmol; 1 eq.) and hydroxylamine (41.6 ml; 705 mmol; 3 eq.) are dissolved in EtOH (800 ml). The resulting solution is heated under reflux for 2 hours. The reaction is followed by NMR. The reaction mixture is then cooled down to RT, and concentrated under vacuum, affording the title compound as a white solid (47.5 g, 99%).

$^1$H NMR (DMSO-d$_6$, 300 MHz) δ 1.36 (s, 9H), 2.08 (t, J=6 Hz, 2H), 3.08 (m, 2H).

Step II: tert-butyl ((3Z)-3-amino-3-{[(2,2-dimethylpropanoyl)oxy]imino}propyl)carbamate To a solution of tert-butyl [(3E)-3-amino-3-(hydroxyimino)propyl]carbamate, obtained in step I as describe above (47.50 g; 233.7 mmol; 1 eq.), in DCM (950 ml) is added at 0° C. N,N-diisopropylethylamine (80.6 ml; 467.42 mmol; 2 eq.). A solution of trimethylacetyl chloride (37.4 ml; 303.8 mmol; 1.30 eq.) in DCM (200 ml) is then dropwise added. The reaction mixture is stirred at 0° C. for 1 h, and is then allowed to warm to RT overnight. The reaction mixture is concentrated under vacuum to 600 ml and diluted with EtOAc (2.5 l). The resulting organic phase is washed with water (1 l) and brine (1 l), and dried over MgSO$_4$. After filtration and evaporation of the solvents, a beige solid is obtained. It is recrystallized in EtOAc (500 ml), affording the title compound as a white solid (27.82 g, 41%). A white precipitate is formed in aqueous phase. It is filtered off and dissolved in DCM (2 l), washed with water (600 ml), brine (600 ml) and dried over MgSO$_4$. After filtration and evaporation of the solvents, a second batch of the title compound is isolated as a white solid (23.3 g, 35%). The title compound is isolated with an overall yield of 76% (51.1 g).

$^1$H NMR (DMSO-d$_6$, 300 MHz) δ 1.19 (s, 9H), 1.38 (s, 9H), 2.19 (t, J=8 Hz, 2H), 3.15 (m, 2H), 6.17 (br s, 2H), 6.78 (m, 1H).

Step III: tert-butyl [2-(5-tert-butyl-1,2,4-oxadiazol-3-yl)ethyl]carbamate

To a stirred suspension of tert-butyl ((3Z)-3-amino-3-{[(2,2-dimethylpropanoyl)oxy]imino}propyl)carbamate, obtained in step II as describe above (51 g; 177 mmol; 1 eq.), in dry THF (1000 ml) under N$_2$, is added dropwise at RT a solution of tetrabutylammonium fluoride solution (177.5 ml; 1 M; 177.5 mmol; 1 eq.) in dry THF (400 ml). At the end of addition, the initial white suspension becomes a yellow solution. The reaction is followed by NMR. After 2 h the reaction is complete. The reaction mixture is poured into EtOAc (1 l) and is washed with water (3×700 ml) and brine (3×700 ml). The organic layer is dried over MgSO$_4$, filtered off and evaporated, affording the title compound as a beige solid (46.6 g, 98%).

$^1$H NMR (DMSO-d$_6$, 300 MHz) δ 1.36 (s, 18H), 2.77 (t, J=7 Hz, 2H), 3.25 (m, 2H), 6.91 (m, 1H).

Step IV: 2-(5-tert-butyl-1,2,4-oxadiazol-3-yl)ethanamine (Amine 15)

To a solution of tert-butyl [2-(5-tert-butyl-1,2,4-oxadiazol-3-yl)ethyl]carbamate, obtained in step III as describe above (46.60 g; 173.0 mmol; 1 eq.), in dry DCM (932 ml) cooled down to 0° C., is added dropwise trifluoroacetic acid (256 ml; 3460 mmol; 20 eq.) over 10 min. The reaction is followed by NMR. After 30 min at 0° C., the solution is concentrated under vacuum. DCM is added and evaporated 4 times and evaporated under high vacuum to give a brown oil. The oil is dissolved in DCM (600 ml) and washed with NaHCO$_3$ sat (150 ml) and dried over MgSO$_4$. After filtration and evaporation of the solvents, Amine 15 is isolate as brown oil (20.8 g, 71%). TFA/base=0.018.

$^1$H NMR (DMSO-d$_6$, 300 MHz) δ 1.37 (s, 9H), 2.87 (t, J=7 Hz, 2H), 3.03 (t, J=7 Hz, 2H), 5.17 (br s, 2H).

Amine 16: Preparation of
2-(5-isopropyl-1,2,4-oxadiazol-3-yl)ethanamine

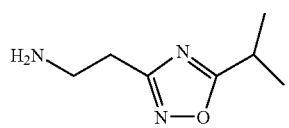

Amine 16

Step I: tert-butyl
[(3E)-3-amino-3-(hydroxyimino)propyl]carbamate

Tert-butyl N-(2-cyanoethyl)carbamate (40 g; 235 mmol; 1 eq.) and hydroxylamine (41.6 ml; 705 mmol; 3 eq.) are dissolved in EtOH (800 ml). The resulting solution is heated under reflux for 2 hours. The reaction progression is followed by $^1$H NMR. After 2 hours, the reaction mixture is cooled down to RT, concentrated under high vacuum to afford the title compound as a white solid (47.5 g, 99%).

$^1$H NMR (DMSO-d$_6$, 300 MHz) δ 1.36 (s, 9H), 2.08 (t, J=6 Hz, 2H), 3.08 (m, 2H).

Step II: tert-butyl [2-(5-isopropyl-1,2,4-oxadiazol-3-yl)ethyl]carbamate

To tert-butyl [(3E)-3-amino-3-(hydroxyimino)propyl]carbamate, obtained in step I as describe above (100 mg; 0.49 mmol; 1 eq), is added isobutyric anhydride (2.0 ml; 12.0 mmol; 24.4 eq). The resulting mixture is heated under microwave irradiation at 180° C. for 20 min. The white precipitate becomes a yellow solution. Diethyl ether is added and the organic layer is washed twice with NaHCO$_3$ sat. solution and twice with NH$_4$Cl sat. solution. The organic layer is dried over MgSO$_4$, filtered and evaporated, affording the title compound that is used in the next step without further purification (88.9 mg; 71%).

Step III:
2-(5-isopropyl-1,2,4-oxadiazol-3-yl)ethanamine
(Amine 16)

Tert-butyl [2-(5-isopropyl-1,2,4-oxadiazol-3-yl)ethyl]carbamate, obtained in step II as describe above (125.1 mg; 0.49 mmol; 1 eq), is dissolved in DCM (3.20 ml). Trifluoroacetic acid (0.80 ml) is added at rt. After 20 min the reaction is complete and the solvents are evaporated. DCM is added and evaporated twice, affording Amine 16 as a colorless oil (132 mg, quantitative yield).

EXAMPLE 1

Ethyl 2'-(acetylamino)-4'-methyl-4,5'-bi-1,3-thiazole-2-carboxylate (1)

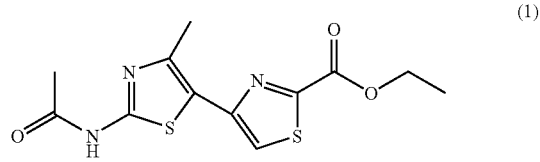

N-[5-(bromoacetyl)-4-methyl-1,3-thiazol-2-yl]acetamide (Intermediate 1)(138.6 mg; 0.50 mmol; 1 eq.) is dissolved in dioxane (5 ml). Ethyl thiooxamate (Aldrich)(66.6 mg; 0.50 mmol; 1 eq.) is added and the mixture is stirred at 65° C. overnight. The reaction mixture is cooled down to rt. The expected product precipitates. It is filtered and washed with dioxane. In order to remove any trace of HBr, it is further dissolved in DCM and an excess of PS-DIEA (Argonaut) is added. After 15 min, the resin is filtered and the solvents are evaporated, affording Compound (1) as white-off solid (72.1 mg; 46%). $^1$H NMR (DMSO-d$_6$, 300 MHz) δ 1.37 (m, 3H), 2.17 (s, 3H), 2.52 (m, 4H), 4.44 (m, 2H), 8.14 (s, 1H), 12.20 (s, 1H). M$^-$ (ESI): 310; M$^+$ (ESI): 312. HPLC (method A), Rt: 2.79 min (purity: 97.9%).

EXAMPLE 2

2'-(Acetylamino)-N-allyl-4'-methyl-4,5'-bi-1,3-thiazole-2-carboxamide (2)

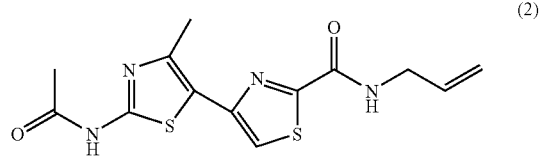

In a microwave tube, ethyl 2'-(acetylamino)-4'-methyl-4,5'-bi-1,3-thiazole-2-carboxylate, Compound (1), (1.0 g, 3.21 mmol, 1 eq.) is dissolved in allylamine (Fluka)(6 ml). The reaction mixture is heated at 80° C. for 20 min under microwave irradiation. The reaction is complete, but some desacetylation is observed. The solvents are evaporated and the crude product is recrystallized in MeOH. Compound (2) is isolated as pale yellow solid (492.9 mg; 47%). $^1$H NMR (DMSO-d$_6$, 300 MHz) δ 2.15 (s, 3H), 2.50 (s, 3H), 3.91 (m, 2H), 5.10 (d, J=12 Hz, 1H), 5.17 (d, J=18 Hz, 1H), 5.88 (m, 1H), 7.99 (s, 1H), 8.94 (t, J=5 Hz, 1H), 12.14 (br s, 1H). M⁻ (ESI): 321.17; M⁺ (ESI): 323.18. HPLC (method A), Rt: 2.84 min (purity: 99.6%).

EXAMPLE 3

N-[2-(cyanomethyl)-4'-methyl-4,5'-bi-1,3-thiazol-2'-yl]acetamide (3)

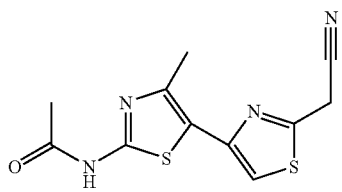

(3)

N-[5-(bromoacetyl)-4-methyl-1,3-thiazol-2-yl]acetamide (Intermediate 1)(1.0 g; 2.79 mmol; 1 eq.) is dissolved in EtOH (25 ml). Triethylamine (980 µl; 6.98 mmol; 2.50 eq.) and 2-cyanothioacetamide (Aldrich)(279.7 mg; 2.79 mmol; 1 eq.) are added. The mixture is stirred 2 h30 at rt. Solvents are evaporated and the crude product is purified by flash chromatography, with cyclohexane/EtOAc gradient as eluent. Compound (3) is isolated as a white-off powder (680.3 mg; 88%). HPLC (method A), Rt 2.30 min (purity: 92.79%). Compound (3) is further crystallized in EtOAc, affording a new batch as colorless needles (412.60 mg; 52.75%). ¹H NMR (DMSO-d₆, 300 MHz) δ 2.13 (s, 3H), 2.47 (s, 3H), 4.61 (s, 2H), 7.71 (s, 1H), 12.12 (br s, 1H). M⁻ (ESI): 277; M⁺ (ESI): 279. HPLC (method A), Rt: 2.28 min (purity: 99.5%).

EXAMPLE 4

2'-(Acetylamino)-4'-methyl-4,5'-bi-1,3-thiazole-2-carboxylic acid (4)

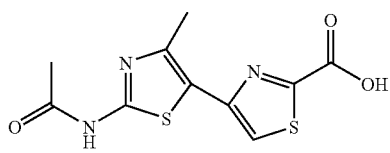

(4)

A solution of ethyl 2'-(acetylamino)-4'-methyl-4,5'-bi-1,3-thiazole-2-carboxylate, Compound (1), (200 mg; 0.64 mmol; 1 eq.) in THF (6 ml) is cooled down to 0° C. Sodium hydroxide (1.60 ml; 5 M; 8.03 mmol; 12.50 eq.) is added dropwise. After 1 h, no starting material can be detected. The mixture is neutralized at 0° C. with HCl 5M solution (1.607 ml; 5 M; 8.03 mmol; 12.50 eq.). The resulting precipitate is filtrated, washed with water and Et₂O, affording Compound (4) as white-off powder (137.5 mg; 76%). 1H NMR (DMSO-d₆, 300 MHz) δ 2.12 (s, 3H), 2.44 (s, 3H), 7.48 (s, 1H), 12.01 (s, 1H). M⁻ (ESI): 282; M⁺ (ESI): 284. HPLC (method A), Rt: 1.90 min (purity: 99.50%). Analysis calculated for $C_{10}H_9N_3O_3S_2$ 2.0H₂O: C, 37.61; H, 4.10; N, 13.16; Exp.: C, 37.73; H, 3.79; N, 13.14. Potassium salt of 2'-(acetylamino)-4'-methyl-4,5'-bi-1,3-thiazole-2-carboxylic acid, Compound (4), is prepared by suspending the parent molecule (90.6 mg; 0.32 mmol; 1 eq.) in THF (3 ml) and water (3 ml). Potassium hydroxide (640 µl; 0.50 M; 0.32 mmol; 1 eq.) is added. The solution is diluted with water, filtered through cotton and lyophylized. The potassium salt of Compound (4) is isolated as white-off solid (104.1 mg; quantitative). ¹H NMR (DMSO-d₆, 300 MHz) δ 2.12 (s, 3H), 2.44 (s, 3H), 7.48 (s, 1H), 12.01 (br s, 1H). M⁻ (ESI): 282; M⁺ (ESI): 284. HPLC (method A), Rt: 1.87 min (purity: 99.4%).

EXAMPLE 5

2'-(Acetylamino)-N42-methoxyethyl)-4'-methyl-4,5'-bi-1,3-thiazole-2-carboxamide (5)

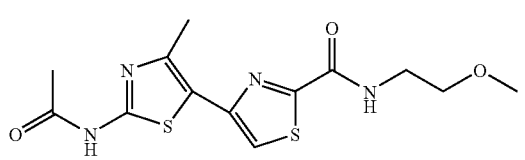

(5)

In a microwave tube, ethyl 2'-(acetylamino)-4'-methyl-4,5'-bi-1,3-thiazole-2-carboxylate, Compound (1), (43.8 mg; 0.14 mmol; 1 eq.) is suspended in 2-methoxyethylamine (Fluka) (0.5 ml). The reaction mixture is heated at 80° C. for 10 min under microwave irradiation. The reaction is complete. The solvents are evaporated and the crude product is recrystallized in MeOH. Compound (5) is isolated as light yellow solid (18.5 mg; 39%). ¹H NMR (DMSO-d₆, 300 MHz) δ 2.14 (s, 3H), 2.49 (s, 3H), 3.26 (s, 3H), 3.47 (m, 4H), 7.98 (s, 1H), 8.68 (sl, 1H), 12.10 (sl, 1H). M⁻ (ESI): 339.07; M⁺ (ESI): 341.09. HPLC (method A), Rt: 2.49 min (purity: 99.6%).

EXAMPLE 6

2'-(Acetylamino)-4'-methyl-N-(tetrahydrofuran-2-ylmethyl)-4,5'-bi-1,3-thiazole-2-carboxamide (6)

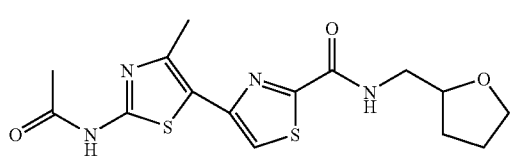

(6)

In a microwave tube, ethyl 2'-(acetylamino)-4'-methyl-4,5'-bi-1,3-thiazole-2-carboxylate, Compound (1), (200 mg; 0.64 mmol; 1 eq.) is dissolved in tetrahydrofurfurylamine (Fluka) (2.0 ml). The reaction mixture is heated at 80° C. for 20 min under microwave irradiation. The reaction is complete, with 7% of de-acetylation. The solvents are evaporated and the crude product is recrystallized in MeOH. Compound (6) is isolated as yellow solid (130.5 mg; 56%). ¹H NMR (DMSO-d₆, 300 MHz) δ 1.56 (m, 1H), 1.78 (m, 3H), 2.14 (s, 3H), 2.49 (s, 3H, CH3CO), 3.32 (m, 2H), 3.64 (m, 1H), 3.78 (m, 1H), 4.02 (m, 1H), 7.98 (s, 1H), 8.64 (s, 1H, NH), 12.14

(s, 1H, NH). M⁻ (ESI): 365; M⁺ (ESI): 367. HPLC (method A), Rt: 2.75 min (purity: 98.5%).

EXAMPLE 7

2'-(Acetylamino)-N-[2-(dimethylamino)ethyl]-4'-methyl-4,5'-bi-1,3-thiazole-2-carboxamide (7)

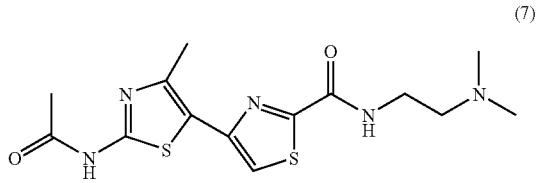

(7)

In a microwave tube, ethyl 2'-(acetylamino)-4'-methyl-4,5'-bi-1,3-thiazole-2-carboxylate, Compound (1), (150 mg; 0.48 mmol; 1 eq.) is dissolved in 2-dimethylaminoethylamine (Fluka)(2.0 ml). The reaction mixture is heated at 80° C. for 20 min under microwave irradiation. The reaction is complete, with 3% of de-acetylation. The solvents are evaporated and the crude product is recrystallized in MeOH. Compound (7) is isolated as white-off solid (112 mg; 66%). $^1$H NMR (DMSO-d$_6$, 300 MHz) δ 2.20 (m, 9H), 2.57 (s, 4H), 3.46 (m, 3H), 8.05 (s, 1H), 8.64 (s, 1H), 11.35 (s, 1H). M⁻ (ESI): 352; M⁺ (ESI): 354. HPLC (method A), Rt: 1.68 min (purity: 99.6%).

EXAMPLE 8

N-[4'-methyl-2-(morpholin-4-ylcarbonyl)-4,5-bi-1,3-thiazol-2'-yl]acetamide (8)

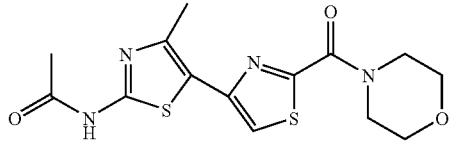

(8)

In a microwave tube, ethyl 2'-(acetylamino)-4'-methyl-4,5'-bi-1,3-thiazole-2-carboxylate, Compound (1), (1000 mg; 3.21 mmol; 1 eq.) is dissolved in morpholine (Fluka)(7.0 ml). The reaction mixture is heated at 80° C. for 30 min under microwave irradiation. The reaction is complete. The solvents are evaporated and the crude product is recrystallized in MeOH. Compound (8) is isolated as light yellow solid (1.320 g; 46%). $^1$H NMR (DMSO-d$_6$, 300 MHz) δ 2.13 (s, 3H), 2.52 (s, 3H), 3.68 (s, 6H), 4.32 (s, 2H), 8 (s, 1H), 12.06 (s, 1H). M⁻ (ESI): 351; M⁺ (ESI): 353. HPLC (method A), Rt: 2.48 min (purity: 98.7%).

EXAMPLE 9

N-{4'-methyl-2-[(4-methylpiperazin-1-yl)carbonyl]-4,5'-bi-1,3-thiazol-2'-yl}acetamide, trifluoroacetate salt (9)

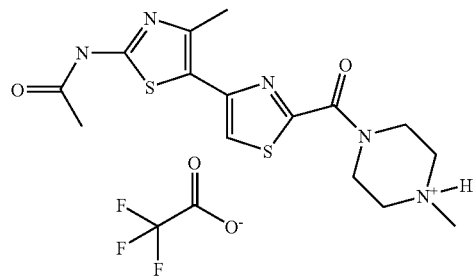

(9)

In a microwave tube, ethyl 2'-(acetylamino)-4'-methyl-4,5'-bi-1,3-thiazole-2-carboxylate, Compound (1), (150 mg; 0.48 mmol; 1 eq.) is dissolved in 1-methylpiperazine(Fluka) (2.0 ml). The reaction mixture is heated at 80° C. for 20+5 min under microwave irradiation. The reaction is complete. The solvents are evaporated and the crude product is purified by preparative HPLC. Trifluoroacetate salt of Compound (9) is isolated as light yellow solid (140 mg; 60%). $^1$H NMR (DMSO-d$_6$, 300 MHz) δ 2.14 (s, 3H), 2.45 (s, 3H), 2.83 (s, 3H), 3.20 (m, 3H), 3.54 (m, 3H), 4.52 (m, 2H), 8.07 (s, 1H), 12.26 (s, 1H). M⁻ (ESI): 364; M⁺ (ESI): 366. HPLC (method A), Rt: 1.70 min (purity: 99.7%).

EXAMPLE 10

2'-(Acetylamino)-N-[3-(dimethylamino)propyl]-4'-methyl-4,5'-bi-1,3-thiazole-2-carboxamide, trifluoroacetate salt (10)

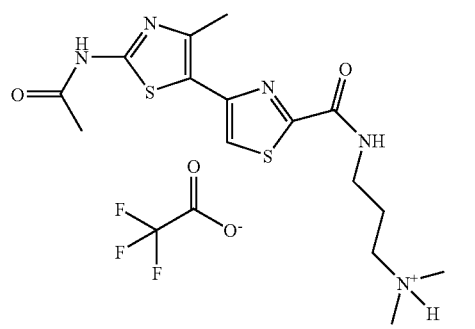

(10)

In a microwave tube, ethyl 2'-(acetylamino)-4'-methyl-4,5'-bi-1,3-thiazole-2-carboxylate, Compound (1), (150 mg; 0.48 mmol; 1 eq.) is dissolved in N,N-dimethyl-1,3-propanediamine (Fluka)(2.0 ml). The reaction mixture is heated at 80° C. for 20 min under microwave irradiation. The reaction is complete. The solvents are evaporated and the crude product is purified by preparative HPLC. Trifluoroacetate salt of Compound (10) is isolated as light yellow solid (108 mg; 47%). $^1$H NMR (DMSO-d$_6$, 300 MHz) δ 1.90 (m, 2H), 2.14 (s, 3H), 2.45 (s, 3H), 2.78 (s, 6H), 3.07 (m, 2H), 3.35 (m, 2H), 8 (s, 1H), 8.88 (s, 1H), 12.16 (s, 1H). M⁻ (ESI): 366; M⁺ (ESI): 368. HPLC (method A), Rt: 1.76 min (purity: 100%).

EXAMPLE 11

2'-(Acetylamino)-N-(2-hydroxyethyl)-4'-methyl-4,5'-bi-1,3-thiazole-2-carboxamide (11)

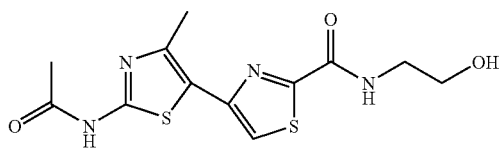

(11)

In a microwave tube, ethyl 2'-(acetylamino)-4'-methyl-4,5'-bi-1,3-thiazole-2-carboxylate, Compound (1), (150 mg; 0.48 mmol; 1 eq.) is dissolved in ethanolamine (Fluka)(2.0 ml). The reaction mixture is heated at 80° C. for 20 min under microwave irradiation. The reaction is complete. The solvents are evaporated and the crude product is purified by preparative HPLC. Compound (11) is isolated as white-off solid (15 mg; 7%). $^1$H NMR (DMSO-$d_6$, 300 MHz) δ 2.14 (s, 3H), 2.45 (s, 3H), 3.37 (m, 2H), 3.52 (m, 2H), 7.98 (s, 1H), 8.59 (m, 1H), 12.14 (s, 1H). M$^-$ (ESI): 325; M$^+$ (ESI): 327. HPLC (method A), Rt: 2.02 min (purity: 98.9%).

EXAMPLE 12

2'-(acetylamino)-N-(2-cyanoethyl)-4'-methyl-4,5'-bi-1,3-thiazole-2-carboxamide (12)

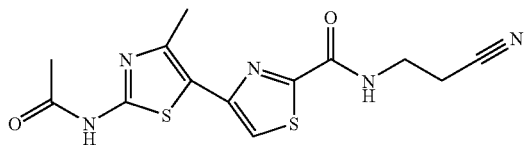

(12)

In a microwave tube, ethyl 2'-(acetylamino)-4'-methyl-4,5'-bi-1,3-thiazole-2-carboxylate, Compound (1), (150 mg; 0.48 mmol; 1 eq.) is dissolved in N-(2-cyanoethyl)amine (Lancaster)(2.0 ml). The reaction mixture is heated at 80° C. for 20 min under microwave irradiation. The reaction is complete. The solvents are evaporated and the crude product is recrystallized in MeOH. Compound (12) is isolated as pale yellow solid (127.1 mg; 78%).

$^1$H NMR (DMSO-$d_6$, 300 MHz) δ 2.13 (s, 3H), 2.48 (s, 3H), 2.81 (m, 2H), 3.55 (m, 2H), 8.01 (s, 1H), 9.02 (s, 1H). M$^-$ (ESI): 334; M$^+$ (ESI): 336. HPLC (method A), Rt: 2.43 min (purity: 98.5%).

EXAMPLE 13

2'-(acetylamino)-4'-methyl-N-1H-tetrazol-5-yl-4,5'-bi-1,3-thiazole-2-carboxamide, potassium salt (13)

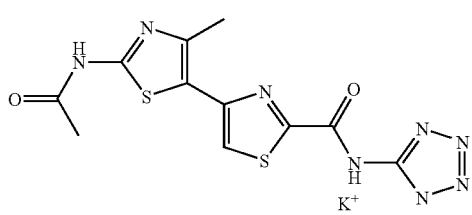

(13)

Step I: 2'-Acetylamino-4'-methyl-[4,5']bithiazolyl-2-carbonyl chloride

2'-(Acetylamino)-4'-methyl-4,5'-bi-1,3-thiazole-2-carboxylic acid, Compound (4), (100 mg; 0.35 mmol; 1 eq.) is suspended in DCM (6 ml). Oxalyl chloride (92 μl; 1.06 mmol; 3 eq.) is added followed by anhydrous dimethylformamide (5.5 μl; 0.07 mmol; 0.20 eq.). After 2 hours, a sample is quenched with MeOH, showing that the reaction is complete. The solvents are evaporated affording 2'-acetylamino-4'-methyl-[4,5']bithiazolyl-2-carbonyl chloride which is used in the next step without further purification. HPLC (method A), Rt: 1.90 min (purity: 92.0%).

Step II: 2'-(acetylamino)-4'-methyl-N-1H-tetrazol-5-yl-4,5'-bi-1,3-thiazole-2-carboxamide, potassium salt (13)

2'-Acetylamino-4'-methyl-[4,5']bithiazolyl-2-carbonyl chloride, obtained in Step I as described above (106.51 mg; 0.35 mmol; 1 eq.), is dissolved in THF (8 ml) and DCM (4 ml). 5-Aminotetrazole (Aldrich)(30.0 mg; 0.35 mmol; 1 eq.) and triethylamine (49 μl; 0.35 mmol; 1 eq.) are added and the mixture is stirred 2.5 h at rt. Solvents are evaporated and the crude product is suspended in MeOH, filtrated, affording Compound (13) as brown solid. Potassium salt of 2'-(acetylamino)-4'-methyl-N-1H-tetrazol-5-yl-4,5'-bi-1,3-thiazole-2-carboxamide, Compound (13), is prepared by dissolving the parent compound in THF (5 ml) and water (5 ml). Potassium hydroxide 0.5N solution (706 μl) is added. The mixture is stirred 10 min at rt, filtered through cotton and is lyophilized. Potassium salt of compound (13) is isolated as a yellow powder (81.9 mg; 60%). $^1$H NMR (DMSO-$d_6$, 300 MHz) δ 1.91 (s, 3H), 2.45 (s, 3H), 3.32 (s, 2H), 7.57 (s, 1H), 9.97 (s, 1H). M$^-$ (ESI): 349.01; M$^+$ (ESI): 351. HPLC (method A), Rt: 2.17 min (purity: 92.7%).

EXAMPLE 14

4-({[2'-(acetylamino)-4'-methyl-4,5'-bi-1,3-thiazol-2-yl]carbonyl}amino) benzoic acid, potassium salt (14)

(14)

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). 4-Aminobenzoic acid (Aldrich)(48.4 mg; 0.35 mmol; 1 eq.) and triethylamine (49 μl; 0.35 mmol; 1 eq.) are added and the mixture is stirred 2.5 h at rt. Solvents are evaporated and the crude product is suspended in MeOH, filtrated, affording Compound (14) as brown solid.

Potassium salt of 4-({[2'-(acetylamino)-4'-methyl-4,5'-bi-1,3-thiazol-2-yl]carbonyl}amino)benzoic acid, Compound (14), is prepared by dissolving the parent compound in THF (5 ml) and water (5 ml). Potassium hydroxide 0.5 N solution (706 μl, 1 eq) is added. The mixture is stirred 10 min at rt, filtered through cotton and is lyophilized. Potassium salt of compound (14) is isolated as a brown powder (65.9 mg; 42%). $^1$H NMR (DMSO-d$_6$, 300 MHz) δ 1.88 (s, 3H), 2.36 (s, 3H), 3.37 (s, 2H), 7.57 (s, 1H), 7.66 (d, J=8 Hz, 2H), 7.81 (d, J=8 Hz, 2H), 10.28 (s, 1H). M$^-$ (ESI): 401.07; M$^+$ (ESI): 403.02. HPLC (method A), Rt: 3.19 min (purity: 95.9%).

EXAMPLE 15

3-({[2'-(acetylamino)-4'-methyl-4,5'-bi-1,3-thiazol-2-yl]carbonyl}amino) benzoic acid, potassium salt (15)

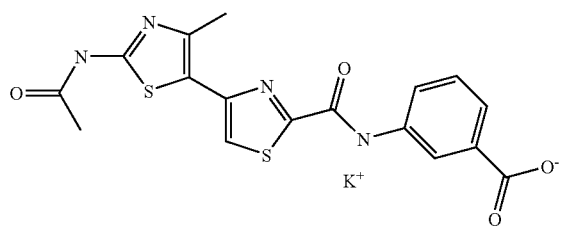

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (2 ml). 3-Aminobenzoic acid (Emkachem) (48.4 mg; 0.35 mmol; 1 eq.) and triethylamine (49 μl; 0.35 mmol; 1 eq.) are added and the mixture is stirred 2.5 h at rt. An orange precipitate is formed. It is filtrated and further purified by crystallization in MeOH, affording compound (15).

Potassium salt of 3-({[2'-(acetylamino)-4'-methyl-4,5'-bi-1,3-thiazol-2-yl]carbonyl}amino)benzoic acid, Compound (15), is prepared by dissolving the parent compound in THF (5 ml) and water (5 ml). Potassium hydroxide 0.5N solution (706 μl, 1 eq) is added. The mixture is stirred 10 min at rt, filtered through cotton and is lyophilized. Potassium salt of compound (15) is isolated as an orange powder (53.8 mg; 35%). $^1$H NMR (DMSO-d$_6$, 300 MHz) δ 1.90 (s, 3H), 2.38 (s, 3H), 3.34 (s, 2H), 7.21 (t, J=8 Hz, 1H), 7.58 (m, 2H), 7.69 (m, 1H), 8.14 (s, 1H), 10.22 (s, 1H). M$^-$ (ESI): 401.10; M$^+$ (ESI): 402.99. HPLC (method A), Rt: 3.18 min (purity: 94.0%).

EXAMPLE 16

2'-(Acetylamino)-4'-methyl-N-[3-(1H-tetrazol-5-yl)phenyl]-4,5'-bi-1,3-thiazole-2-carboxamide, potassium salt (16)

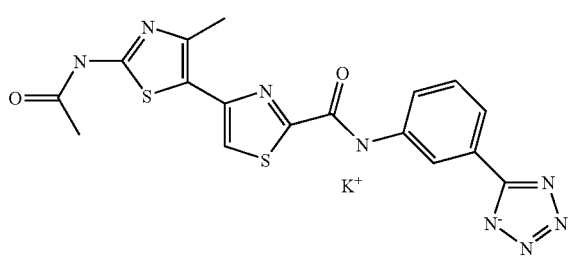

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). 5-(3-Aminophenyl)tetrazole (Avocado) (56.9 mg; 0.35 mmol; 1 eq.) and triethylamine (49 μl; 0.35 mmol; 1 eq.) are added and the mixture is stirred 2.5 h at rt. A brown precipitate is formed. Solvents are evaporated and the crude product is crystallized in MeOH, affording Compound (16) as a brown solid.

Potassium salt of 2'-(acetylamino)-4'-methyl-N-[3-(1H-tetrazol-5-yl)phenyl]-4,5'-bi-1,3-thiazole-2-carboxamide, Compound (16), is prepared by dissolving the parent compound in THF (5 ml) and water (5 ml). Potassium hydroxide 0.5N solution (706 μl, 1 eq) is added. The mixture is stirred 10 min at rt, filtered through cotton and is lyophilized. Potassium salt of compound (16) is isolated as a dark orange powder (66.4 mg; 40.5%). $^1$H NMR (DMSO-d$_6$, 300 MHz) δ 2.02 (s, 3H), 2.5 (s, 3H), 3.32 (s, 2H), 7.35 (t, J=8 Hz, 1H), 7.73 (m, 2H), 7.83 (s, 1H), 8.41 (t, J=11 Hz, 1H), 10.5 (s, 1H). M$^-$ (ESI): 425.09; M$^+$ (ESI): 427.13. HPLC (method A), Rt: 3.12 min (purity: 89.7%).

EXAMPLE 17

2'-(Acetylamino)-N-benzyl-4'-methyl-4,5'-bi-1,3-thiazole-2-carboxamide (17)

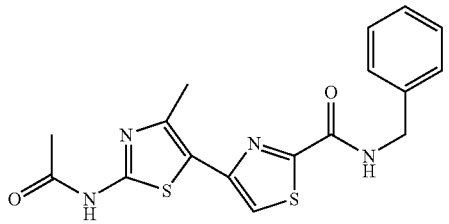

In a microwave tube, ethyl 2'-(acetylamino)-4'-methyl-4,5'-bi-1,3-thiazole-2-carboxylate, Compound (1), (150 mg; 0.48 mmol; 1 eq.) is dissolved in benzylamine (Fluka)(2.0 ml). The reaction mixture is heated at 80° C. for 20 min under microwave irradiation. The reaction is complete. The solvents are evaporated and the crude product is purified by preparative HPLC. Compound (17) is isolated as white-off solid (45 mg, 25%). $^1$H NMR (DMSO-d$_6$, 300 MHz) δ 2.09 (s, 3H), 2.16 (s, 3H), 4.50 (d, J=9 Hz, 2H), 7.30-7.45 (m, 5H), 8.02 (s, 1H), 9.37 (t, J=9 Hz, 1H). M$^-$ (ESI): 371.11; M$^+$ (ESI): 373.13. (method A), Rt: 3.52 min (purity: 96.2%).

EXAMPLE 18

2'-(Acetylamino)-4'-methyl-N-propyl-4,5'-bi-1,3-thiazole-2-carboxamide (18)

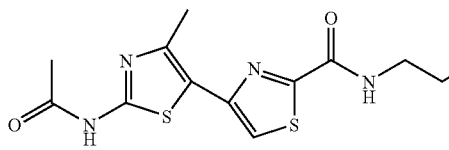

In a microwave tube, ethyl 2'-(acetylamino)-4'-methyl-4,5'-bi-1,3-thiazole-2-carboxylate, Compound (1), (350 mg; 1.124 mmol; 1 eq.) is dissolved in N-propylamine (Fluka)(5.0 ml). The reaction mixture is heated at 80° C. for 20 min under microwave irradiation. The reaction is complete, with 15% of de-acetylation. The solvents are evaporated and the crude product is purified by crystallization in MeOH. Compound (18) is isolated as yellow solid (123 mg; 38%). ¹H NMR (DMSO-d₆, 300 MHz) δ 0.87 (t, J=6 Hz, 3H), 1.55 (m, 2H), 2.14 (s, 3H), 3.24 (m, 2H), 3.31 (s, 3H), 7.96 (s, 1H), 8.75 (t, J=6 Hz, 1H), 11.5 (br s, 1H). M⁻ (ESI): 323.14; M⁺ (ESI): 325.18. HPLC (method A), Rt: 3 min (purity: 97.6%).

EXAMPLE 19

2'-(acetylamino)-4'-methyl-N-[4-(1H-tetrazol-5-yl)phenyl]-4,5'-bi-1,3-thiazole-2-carboxamide, potassium salt (19)

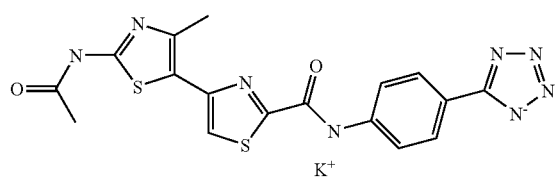

(19)

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). 4-(2H-Tetrazol-3-yl)aniline hydrochloride (Asimex)(69.7 mg; 0.35 mmol; 1 eq.) and triethylamine (49 μl; 0.35 mmol; 1 eq.) are added and the mixture is stirred 2.5 h at rt. Solvents are evaporated and the crude product is suspended in MeOH/Et₂O, filtrated, affording Compound (19) as a brown solid (63.4 mg, 42%). HPLC (method A), Rt 3.07 min (purity: 86.1%).

Compound (19) is further purified by preparative HPLC (11.8 mg; 17%).

Potassium salt of 2'-(acetylamino)-4'-methyl-N-[4-(1H-tetrazol-5-yl)phenyl]-4,5'-bi-1,3-thiazole-2-carboxamide, Compound (19), is prepared by dissolving the parent compound (11.8 mg; 0.028 mmol) in THF (2 ml) and water (2 ml). Potassium hydroxide 0.5N solution (56.5 μl; 0.50 M; 0.03 mmol; 1 eq.) is added. The mixture is stirred 10 min at rt, filtered through cotton and is lyophilized. Potassium salt of compound (19) is isolated as a yellow solid (11.8 mg, 92%). ¹H NMR (DMSO-d₆, 300 MHz) δ 2.16 (s, 3H), 2.53 (s, 3H), 7.82 (d, J=9 Hz, 2H), 7.95 (d, J=9 Hz, 2H), 8.07 (s, 1H), 10.57 (s, 1H). M⁻ (ESI): 425; M⁺ (ESI): 427. HPLC (method A), Rt: 3.08 min (purity: 95.5%).

EXAMPLE 20

3-({[2'-(acetylamino) 4'-methyl-4,5'-bi-1,3-thiazol-2-yl]carbonyl}amino)-2-hydroxybenzoic acid, potassium salt (20)

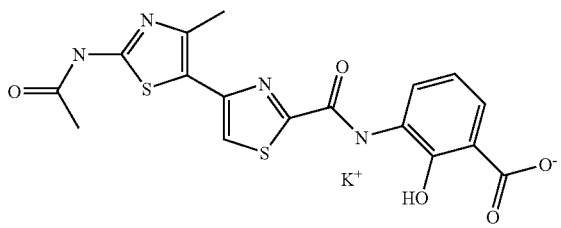

(20)

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). 3-Aminosalicylic acid (TCI-US)(54.05 mg; 0.35 mmol; 1 eq.) and triethylamine (97 μl; 0.70 mmol; 2 eq.) are added and the mixture is stirred overnight at rt. Solvents are evaporated and the crude product is in MeOH, filtrated, affording Compound (20) as a yellow solid (61 mg; 42%).

Potassium salt of 2'-(acetylamino)-4'-methyl-N-[4-(1H-tetrazol-5-yl)phenyl]-4,5'-bi-1,3-thiazole-2-carboxamide, Compound (20), is prepared by dissolving the parent compound (58.3 mg; 0.14 mmol; 1 eq.) in THF (2 ml) and water (2 ml). Potassium hydroxide 0.5 N solution (279 μl; 0.50 M; 0.14 mmol; 1 eq.) is added. The mixture is stirred 10 min at rt, filtered through cotton and is lyophilized. Potassium salt of compound (20) is isolated as a yellow solid (58 mg, 91%). ¹H NMR (DMSO-d₆, 300 MHz) δ 2.16 (s, 3H), 2.55 (s, 3H), 6.47 (t, J=8 Hz, 1H), 7.39 (dd, J=8 Hz, J=2 Hz, 1H), 8.07 (s, 1H), 8.18 (dd, J=8, 2 Hz, 1H), 9.97 (s, 1H), 12.19 (s, 1H). M⁻ (ESI): 417.1; M⁺ (ESI): 419.1. HPLC (method A), Rt: 1.50 min (purity: 92.3%).

EXAMPLE 21

1-{[2'-(acetylamino)-4'-methyl-4,5'-bi-1,3-thiazol-2-yl]carbonyl}piperidine-3-carboxylic acid (21)

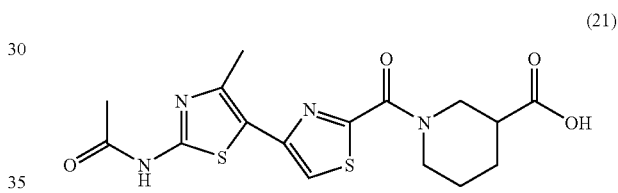

(21)

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). Nipecotic acid (Emkachem)(42.8 mg; 0.33 mmol; 1 eq.) and triethylamine (97 μl; 0.70 mmol; 2 eq.) are added and the mixture is stirred overnight at rt. Solvents are evaporated and the crude product is crystallized in MeOH, filtrated, affording Compound (21) as a brown solid (31 mg; 23%). M⁻ (ESI): 393; M⁺ (ESI): 395. HPLC (method A), Rt: 2.60 min (purity: 95.4%).

EXAMPLE 22

5-({[2'-(acetylamino)-4'-methyl-4,5'-bi-1,3-thiazol-2-yl]carbonyl}amino)-2-hydroxybenzoic acid, potassium saltm (22)

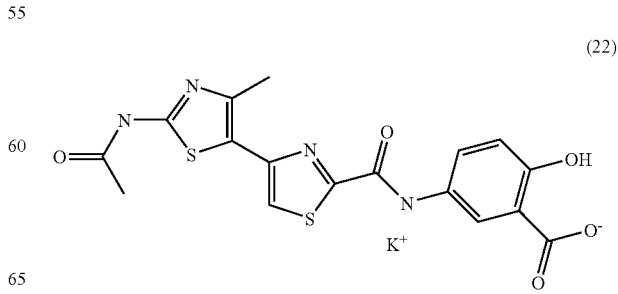

(22)

Step I: 2 mL(acetylamino)-N-(2,2-dimethyl-4-oxo-4H-1,3-benzodioxin-6-yl)-4'-methyl-4,5'-bi-1,3-thiazole-2-carboxamide 2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). 6-Amino-2,2-dimethyl-benzo[1,3]dioxin-4-one, Amine 1 obtained as described above, (67.6 mg; 0.35 mmol; 1 eq.) and triethylamine (49 µl; 0.35 mmol; 1 eq.) are added and the mixture is stirred 2.5 h at rt. Solvents are evaporated and the crude product is recrystallized in MeOH, filtrated, affording 2'-(acetylamino)-N-(2,2-dimethyl-4-oxo-4H-1,3-benzodioxin-6-yl)-4'-methyl-4,5'-bi-1,3-thiazole-2-carboxamide as an orange solid (68.9 mg; 43%). $^1$H NMR (DMSO-$d_6$, 300 MHz) δ 1.70 (s, 6H), 2.15 (s, 3H), 2.52 (s, 3H), 7.16 (d, J=8 Hz, 1H), 8.09 (s, 1H), 8.10 (dd, J=8, 3 Hz, 1H), 8.41 (d, J=3 Hz, 1H), 10.81 (s, 1H), 12.16 (s, 1H). M$^-$ (ESI): 457.04; M$^+$ (ESI): 459.12. HPLC (method A), Rt: 3.78 min (purity: 97.7%).

Step II: 5-({[2'-(acetylamino)-4'-methyl-4,5'-bi-1,3-thiazol-2-yl]carbonyl}amino)-2-hydroxybenzoic acid (22)

Sodium hydroxide 5N solution (109 µl; 5 M; 0.55 mmol; 12.50 eq.) is added to a solution of 2'-(acetylamino)-N-(2,2-dimethyl-4-oxo-4H-1,3-benzodioxin-6-yl)-4'-methyl-4,5'-bi-1,3-thiazole-2-carboxamide, obtained in Step I as described above (20 mg; 0.04 mmol; 1 eq.) in THF (1 ml) at rt. After 50 min, the deprotection is complete. Hydrogen chloride (109 µl; 5 M; 0.55 mmol; 12.50 eq.) is added, followed by water (2 ml). The resulting precipitate is isolated by filtration, washed with water and dried under vacuo. Compound (22) is isolated as yellow solid (14 mg; 77%).

Potassium salt of 5-({[2'-(acetylamino)-4'-methyl-4,5'-bi-1,3-thiazol-2-yl]carbonyl}amino)-2-hydroxybenzoic acid, Compound (22), is prepared by dissolving the parent compound (14 mg; 0.03 mmol) in THF (5 ml) and water (5 ml). Potassium hydroxide 0.5 N solution (61 µl; 0.50 M; 0.03 mmol; 1 eq.) is added. The mixture is stirred 10 min at rt, filtered through cotton and is lyophilized. Potassium salt of compound (22) is isolated as a yellow powder (15.6 mg; 78%). $^1$H NMR (DMSO-$d_6$, 300 MHz) δ 2.15 (s, 3H), 2.53 (s, 3H), 6.60 (d, J=9 Hz, 1H), 7.52 (dd, J=3, 9 Hz, 1H), 7.98 (d, J=3 Hz, 1H), 8.01 (s, 1H), 10.26 (s, 1H), 12.14 (s, 1H). M$^-$ (ESI): 417.07; M$^+$ (ESI): 418.99. HPLC (method A), Rt: 3.15 min (purity: 86.4%).

EXAMPLE 23

N-[4'-methyl-2-(2H-tetrazol-5-ylmethyl)-4,5'-bi-1,3-thiazol-2'-yl]acetamide, potassium salt (23)

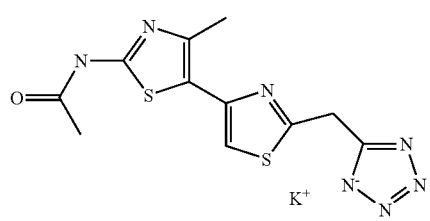

(23)

N-[2-(cyanomethyl)-4'-methyl-4,5'-bi-1,3-thiazol-2'-yl] acetamide, Compound (3) obtained as described previously (100 mg; 0.36 mmol), is dissolved in Toluene (5 ml). Trimethylsilyl azide (0.33 ml; 2.51 mmol; 7 eq.) and dibutyltin oxide (53.7 mg; 0.22 mmol; 0.60 eq.) are added and the mixture is heated under reflux for 3 hours. The solvents are removed and the crude product is suspended in MeOH. Compound (23) is isolated after filtration as a brown solid (54.6 mg, 47%).

Potassium salt of N-[4'-methyl-2-(2H-tetrazol-5-ylmethyl)-4,5'-bi-1,3-thiazol-2'-yl]acetamide, Compound (23), is prepared by dissolving the parent compound (54.6 mg, 0.170 mmol) in THF (5 ml) and water (5 ml). Potassium hydroxide 1N solution (169 µl; 0.169 mmol, 1 eq.) is added. The mixture is stirred 10 min at rt, filtered through cotton and is lyophilized. Potassium salt of compound (23) is isolated as a yellow powder (65.5 mg; quantitative). $^1$H NMR (DMSO-$d_6$, 300 MHz) δ 2.11 (s, 3H), 2.44 (s, 3H), 4.37 (s, 2H), 7.46 (s, 1H), 12.10 (br s, 1H). M$^-$ (ESI): 320; M$^+$ (ESI): 322. HPLC (method A), Rt: 1.96 min (purity: 99.3%).

EXAMPLE 24

1-{[2'-(acetylamino)-4-methyl-4,5'-bi-1,3-thiazol-2-yl]carbonyl}piperidine-4-carboxylic acid, potassium salt (24)

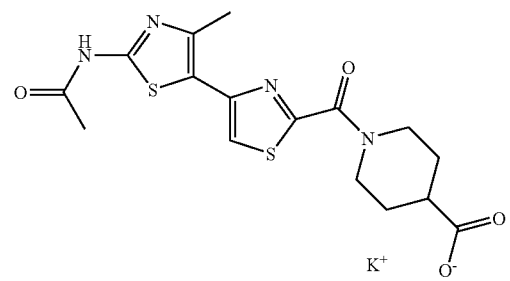

(24)

2'-Acetylamino-4'-methyl-[4,5']bithiazolyl-2-carbonyl chloride, prepared as in Step I of Example 13, described above, (106.5 mg; 0.35 mmol; 1 eq.), is dissolved in THF (8 ml) and DCM (4 ml). Isonipecotic acid (Fluka)(45.2 mg; 0.35 mmol; 1 eq.) and triethylamine (49 µl; 0.35 mmol; 1 eq.) are added and the mixture is stirred 2.5 h at rt. Solvents are evaporated and the crude product is purified by preparative HPLC. In order to remove any traces of trifluoroacetic acid, the resulting product is dissolved in THF and an excess of PS-DIEA (Argonaut) is added. The resulting mixture is shaken for 3 hours at rt, filtrated and evaporated, affording compound (24) as parent product (70 mg; 51%).

Potassium salt of 1-{[2'-(acetylamino)-4'-methyl-4,5'-bi-1,3-thiazol-2-yl]carbonyl}piperidine-4-carboxylic acid, Compound (24), is prepared by dissolving the parent compound (70 mg, 0.177 mmol) in THF (5 ml) and water (5 ml). Potassium hydroxide 1N solution (177 µl, 1 eq) is added. The mixture is stirred 10 min at rt, filtered through cotton and is lyophilized. Potassium salt of Compound (24) is isolated as a yellow solid (61 mg; 80%). M$^-$ (ESI): 393.10; M$^+$ (ESI): 395.12. HPLC (method A), Rt: 2.55 min (purity: 98.2%).

EXAMPLE 25

2'-(acetylamino)-N-[3-(5-amino-1,3,4-thiadiazol-2-yl)phenyl]-4'-methyl-4,5'-bi-1,3-thiazole-2-carboxamide (25)

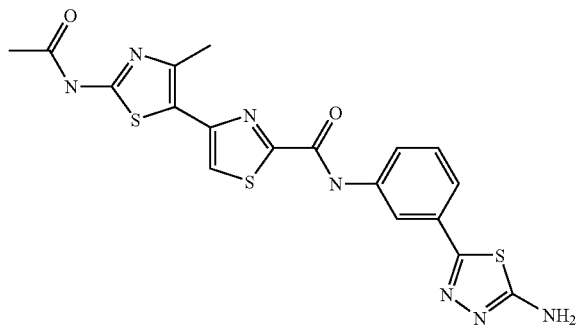

(25)

2'-Acetylamino-4'-methyl-[4,5']bithiazolyl-2-carbonyl chloride, prepared as in Step I of Example 13, described above, (117.7 mg; 0.39 mmol; 1 eq.), is dissolved in THF (8 ml) and DCM (2 ml). 5-(3-Aminophenyl)-1,3,4-thiadiazol-2-amine, Amine 2 obtained as described above, (75 mg; 0.39 mmol; 1 eq.) and triethylamine (108 µl; 0.78 mmol; 2 eq.) are added and the mixture is stirred overnight at rt. Solvents are evaporated. The resulting crude mixture is suspended in MeOH, filtrated and washed with MeOH and water (106.9 mg; 60%). It is further purified by preparative HPLC, affording Compound (25) as light yellow solid (22.2 mg; 10%). $^1$H NMR (DMSO-$d_6$, 300 MHz) δ 2.15 (s, 3H), 2.52 (s, 3H), 7.52 (m, 4H), 7.91 (m, 1H), 8.10 (s, 1H), 8.29 (m, 1H), 10.77 (br s, 1H), 12.17 (br s, 1H). M$^-$ (ESI): 456; M$^+$ (ESI): 458. HPLC (method A), Rt: 2.92 min (purity: 94.2%).

EXAMPLE 26

N-{2-[(3-hydroxypiperidin-1-yl)carbonyl]-4'-methyl-4,5'-bi-1,3-thiazol-2'-yl}acetamide (26)

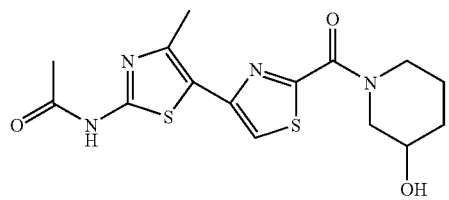

(26)

2'-Acetylamino-4'-methyl-[4,5']bithiazolyl-2-carbonyl chloride, prepared as in Step I of Example 13, described above, (200 mg, 0.66 mmol, 1 eq.), is dissolved in THF (8 ml) and DCM (4 ml). 3-Hydroxypiperidine (Fluka)(67.0 mg; 0.66 mmol; 1 eq.) and triethylamine (0.19 ml; 1.33 mmol; 2 eq.) are added and the mixture is stirred overnight at rt. Solvents are evaporated and the crude product is crystallized in MeOH, affording Compound (26) as a brown solid (103 mg; 42%). M$^-$ (ESI): 365.20; M$^+$ (ESI): 367.16. HPLC (method A), Rt: 2.35 min (purity: 99.4%).

EXAMPLE 27

N-(2-{[4-(hydroxymethyl)piperidin-1-yl]carbonyl}-4'-methyl-4,5'-bi-1,3-thiazol-2'-yl)acetamide (27)

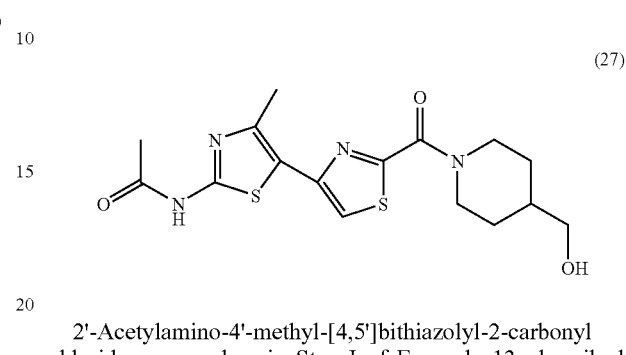

(27)

2'-Acetylamino-4'-methyl-[4,5']bithiazolyl-2-carbonyl chloride, prepared as in Step I of Example 13, described above, (200 mg, 0.66 mmol, 1 eq.), is dissolved in THF (8 ml) and DCM (4 ml). 4-(Hydroxymethyl)piperidine (Maybridge) (76.3 mg; 0.66 mmol; 1 eq.) and triethylamine (0.19 ml; 1.33 mmol; 2 eq.) are added and the mixture is stirred overnight at rt. Solvents are evaporated and the crude product is crystallized in MeOH, affording Compound (27) as a brown solid (106.3 mg; 42%). $^1$H NMR (DMSO-$d_6$, 300 MHz) δ 1.05-1.30 (m, 2H), 1.65-1.87 (m, 3H), 2.14 (s, 3H), 2.50 (s, 3H), 2.86 (m, 1H), 3.20 (m, 1H), 3.28 (m, 2H), 4.48 (m, 1H), 4.52 (t, J=4.5 Hz, 1H), 5.16 (m, 1H), 7.97 (s, 1H), 12.16 (s, 1H). M$^-$ (ESI): 379.20; M$^+$ (ESI): 381.19. HPLC (method A), Rt: 2.47 min (purity: 99%).

EXAMPLE 28

N-(2-{[4-(2-hydroxyethyl)piperidin-1-yl]carbonyl}-4'-methyl-4,5'-bi-1,3-thiazol-2'-yl)acetamide (28)

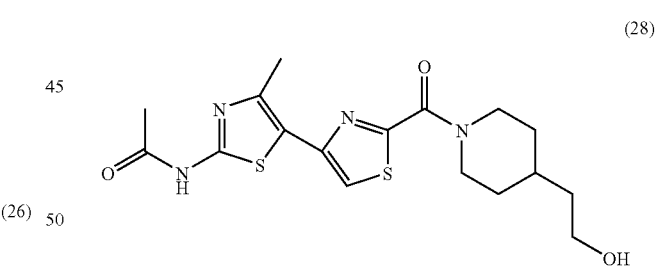

(28)

2'-Acetylamino-4'-methyl-[4,5']bithiazolyl-2-carbonyl chloride, prepared as in Step I of Example 13, described above, (200 mg, 0.66 mmol, 1 eq.), is dissolved in THF (8 ml) and DCM (4 ml). 4-Piperidineethanol (Aldrich)(85.6 mg; 0.66 mmol; 1 eq.) and triethylamine (0.19 ml; 1.33 mmol; 2 eq.) are added and the mixture is stirred overnight at rt. Solvents are evaporated and the crude product is crystallized in MeOH, affording Compound (28) as a brown solid (117.2 mg; 43%). $^1$H NMR (DMSO-$d_6$, 300 MHz) δ 1.05-1.30 (m, 2H), 1.38 (m, 2H), 1.75 (m, 2H), 2.13 (s, 3H), 2.48 (s, 3H), 2.85 (m, 1H), 3.22 (m, 1H), 3.45 (m, 2H), 4.38 (t, J=6 Hz, 1H), 4.42 (m, 1H), 5.15 (m, 1H), 7.97 (s, 1H), 12.16 (s, 1H). M$^-$ (ESI): 393.21; M$^+$ (ESI): 395.20. HPLC (method A), Rt: 2.69 min (purity: 95.7%).

EXAMPLE 29

N-{2-[(4-hydroxypiperidin-1-yl)carbonyl]-4'-methyl-4,5'-bi-1,3-thiazol-2'-yl}acetamide (29)

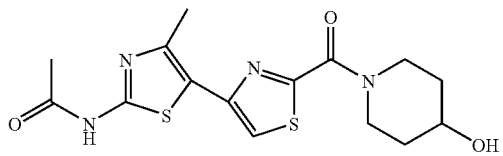

2'-Acetylamino-4'-methyl-[4,5']bithiazolyl-2-carbonyl chloride, prepared as in Step I of Example 13, described above, (166.6 mg, 0.55 mmol, 1 eq.), is dissolved in THF (8 ml) and DCM (4 ml). 4-Hydroxypiperidine (Fluka)(55.8 mg; 0.55 mmol; 1 eq.) and triethylamine (0.15 ml; 1.10 mmol; 2 eq.) are added and the mixture is stirred overnight at rt. Solvents are evaporated and the crude product is crystallized in MeOH, affording Compound (29) as a brown solid (80.3 mg; 40%). $^1$H NMR (DMSO-d$_6$, 300 MHz) δ 1.44 (m, 2H), 1.82 (m, 2H), 2.14 (s, 3H), 2.50 (s, 3H), 3.35 (m, 2H), 3.80 (m, 2H), 4 (m, 1H), 4.60 (m, 1H), 7.98 (s, 1H), 12.16 (br s, 1H). M$^-$ (ESI): 365; M$^+$ (ESI): 367. HPLC (method A), Rt: 2.31 min (purity: 91.1%).

EXAMPLE 30

2'-(acetylamino)-N-1H-1,2,3-benzotriazol-5-yl-4'-methyl-4,5'-bi-1,3-thiazole-2-carboxamide, potassium salt (30)

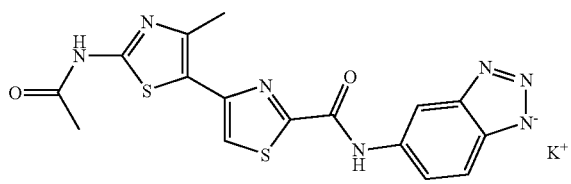

2'-Acetylamino-4'-methyl-[4,5']bithiazolyl-2-carbonyl chloride, prepared as in Step I of Example 13, described above, (200 mg, 0.66 mmol, 1 eq.), is dissolved in THF (8 ml) and DCM (4 ml). 5-Aminobenzotriazole (Aldrich)(88.9 mg; 0.66 mmol; 1 eq.) and triethylamine (0.19 ml; 1.33 mmol; 2 eq.) are added and the mixture is stirred overnight at rt. Solvents are evaporated and the crude product is purified by preparative HPLC. In order to remove any traces of trifluoroacetic acid, the resulting product is dissolved in DCM and an excess of PS-DIEA (Argonaut) is added. The resulting mixture is shaken for 3 hours at rt, filtrated and evaporated, affording compound (30) as parent product (57 mg; 22%). Potassium salt of 2'-(acetylamino)-N-1H-1,2,3-benzotriazol-5-yl-4'-methyl-4,5'-bi-1,3-thiazole-2-carboxamide, Compound (30), is prepared by dissolving the parent compound (57 mg, 0.143 mmol) in THF (2 ml) and water (2 ml). Potassium hydroxide 0.5N solution (285 μl, 1 eq) is added. The mixture is stirred 10 min at rt, filtered through cotton and is lyophilized. Potassium salt of compound (30) is isolated as a yellow solid (42 mg; 67%). $^1$H NMR (DMSO-d$_6$, 300 MHz) δ 2.04 (s, 3H), 2.50 (s, 3H), 7.20 (d, J=9 Hz, 1H), 7.54 (d, J=9 Hz, 1H), 7.83 (s, 1H), 8.06 (s, 1H), 10.17 (s, 1H). M$^-$ (ESI): 398.10; M$^+$ (ESI): 400.09. HPLC (method A), Rt: 2.85 min (purity: 90.2%).

EXAMPLE 31

4-({[2'-(acetylamino)-4'-methyl-4,5-bi-1,3-thiazol-2-yl]carbonyl}amino)-2-hydroxybenzoic acid, potassium salt (31)

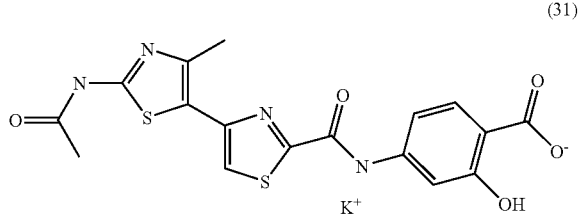

Step I: 2'-(acetylamino)-N-(2,2-dimethyl-4-oxo-4H-1,3-benzodioxin-7-yl)-4'-methyl-4,5'-bi-1,3-thiazole-2-carboxamide 2'-Acetylamino-4'-methyl-[4,5']bithiazolyl-2-carbonyl chloride, prepared as in Step I of Example 13, described above, (200 mg, 0.66 mmol, 1 eq.), is dissolved in THF (8 ml) and DCM (4 ml). 7-Amino-2,2-dimethyl-4H-1,3-benzodioxine-4-one, Amine 3 prepared as described above, (128.0 mg; 0.66 mmol; 1 eq.) and triethylamine (0.19 ml; 1.33 mmol; 2 eq.) are added and the mixture is stirred overnight at rt. Solvents are evaporated and the crude product is purified by crystallization in MeOH. The resulting product is washed with MeOH and NaHCO$_3$ (sat), affording 2'-(acetylamino)-N-(2,2-dimethyl-4-oxo-4H-1,3-benzodioxin-7-yl)-4'-methyl-4,5'-bi-1,3-thiazole-2 carboxamide as a beige solid (200 mg; 65%). $^1$H NMR (DMSO-d$_6$, 300 MHz) δ 1.67 (s, 6H), 2.13 (s, 3H), 2.49 (s, 3H), 7.28 (m, 1H), 7.56 (s, 1H), 7.64 (br d, J=9 Hz, 1H), 7.75 (s, 1H), 11.65 (br s, 1H). M$^-$ (ESI): 457.08; M$^+$ (ESI): 459.13. HPLC (method A), Rt: 3.86 min (purity: 97.7%).

Step II: 4-({[2'-(acetylamino)-4'-methyl-4,5'-bi-1,3-thiazol-2-yl]carbonyl}amino)-2-hydroxybenzoic acid (31)

2'-(acetylamino)-N-(2,2-dimethyl-4-oxo-4H-1,3-benzodioxin-7-yl)-4'-methyl-4,5'-bi-1,3-thiazole-2-carboxamide (150 mg; 0.33 mmol; 1 eq.) is dissolved in THF (6 ml). Sodium hydroxide (0.82 ml; 5 M; 4.09 mmol; 12.50 eq.) is added and the mixture is stirred at rt for 10 days. Hydrogen chloride (0.82 ml; 5 M; 4.09 mmol; 12.50 eq.) is added and the solvents are evaporated. The resulting crude product is purified by preparative HPLC. To remove the TFA, the compound is dissolved in THF and an excess of POL-Trisamine (Argonault) is added. The solution is filtrated and evaporated, affording Compound (31)(54 mg; 39%). Potassium salt of 4-({[2'-(acetylamino)-4'-methyl-4,5'-bi-1,3-thiazol-2-yl]carbonyl}amino)-2-hydroxybenzoic acid, Compound (31), is prepared by dissolving the parent compound (54 mg, 0.129 mmol) in THF (2 ml) and water (2 ml). Potassium hydroxide 0.5N solution (258 μl, 1 eq) is added. The mixture is stirred 10 min at rt, filtered through cotton and is lyophilized. Potassium salt of compound (31) is isolated as a yellow solid (21.6 mg; 36%).
$^1$H NMR (DMSO-d$_6$, 300 MHz) δ 1.93 (s, 3H), 2.48 (s, 3H), 6.70-7.75 (br m, 4H), 10.15 (br s, 1H). M$^-$ (ESI): 417.05; M$^+$ (ESI): 419.10. HPLC (method A), Rt: 3.29 min (purity: 97.7%).

EXAMPLE 32

4-({[2'-(acetylamino)-4'-methyl-4,5'-bi-1,3-thiazol-2-yl]carbonyl}amino)-2-fluorobenzoic acid, potassium salt (32)

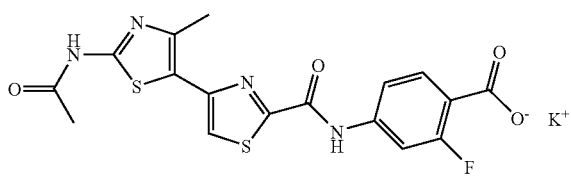

(32)

2'-Acetylamino-4'-methyl-[4,5']bithiazolyl-2-carbonyl chloride, prepared as in Step I of Example 13, described above, (166.6 mg, 0.55 mmol; 1 eq.), is dissolved in THF (8 ml) and DCM (4 ml). 4-Amino-2-fluorobenzoic acid (Apollo)(85.7 mg; 0.55 mmol; 1 eq.) and triethylamine (0.15 ml; 1.10 mmol; 2 eq.) are added and the mixture is stirred overnight at rt. Solvents are evaporated and the crude product is purified by preparative HPLC. It is further washed with MeOH, affording Compound (32) as yellow solid (8.9 mg; 3.3%). Potassium salt of 4-({[2'-(acetylamino)-4'-methyl-4,5'-bi-1,3-thiazol-2-yl]carbonyl}amino)-2-fluorobenzoic acid, Compound (32), is prepared by dissolving the parent compound (8.9 mg; 0.021 mmol) in THF (2 ml) and water (2 ml). Potassium hydroxide 0.5 N solution (42 µl, 1 eq.) is added. The mixture is stirred 10 min at rt, filtered through cotton and is lyophilized. Potassium salt of compound (32) is isolated as a yellow solid (9.7 mg; quantitative). $^1$H NMR (DMSO-d$_6$, 300 MHz) δ 2.05 (s, 3H), 2.49 (s, 3H), 7.40-7.60 (m, 3H), 7.89 (s, 1H), 10.65 (br s, 1H). M$^-$ (ESI): 418.99; M$^+$ (ESI): 421.10. HPLC (method A), Rt: 3.18 min (purity: 93%).

EXAMPLE 33

2'-(acetylamino)-N-[3-(5-hydroxy-1,3,4-oxadiazol-2-yl)phenyl]-4'-methyl-4,5'-bi-1,3-thiazole-2-carboxamide, potassium salt (33)

(33)

2'-Acetylamino-4'-methyl-[4,5']bithiazolyl-2-carbonyl chloride, prepared as in Step I of Example 13, described above, (170.5 mg; 0.56 mmol; 1 eq.), is dissolved in THF (8 ml) and DCM (4 ml). 5-(3-Aminophenyl)-1,3,4-oxadiazol-2-ol, Amine 4 obtained as described above, (100.0 mg; 0.56 mmol; 1 eq.) and triethylamine (79 µl; 0.56 mmol; 1 eq.) are added and the mixture is stirred overnight at rt. Solvents are evaporated and the crude product is purified by preparative HPLC. In order to remove any traces of trifluoroacetic acid, the resulting product is dissolved in DCM and an excess of PS-DIEA (Argonaut) is added. The resulting mixture is shaken for 3 hours at rt, filtrated and evaporated, affording compound (33) as parent product (34.8 mg, 14%). HPLC (method A), Rt: 3.30 min (purity: 92.0%). Potassium salt of 2'-(acetylamino)-N-[3-(5-hydroxy-1,3,4-oxadiazol-2-yl)phenyl]-4'-methyl-4,5'-bi-1,3-thiazole-2-carboxamide, Compound (33), is prepared by dissolving the parent compound (24 mg; 0.05 mmol; 1 eq.) in THF (3 ml) and water (3 ml). Potassium hydroxide 0.5N solution (106 µl; 0.50 M; 0.05 mmol; 0.98 eq.) is added. The mixture is stirred 10 min at rt, filtered through cotton and is lyophilized. Potassium salt of compound (33) is isolated as a pale yellow solid (19.3 mg, 74.0%). $^1$H NMR (DMSO-d$_6$, 300 MHz) δ 2.15 (s, 3H), 2.53 (s, 3H), 7.37 (m, 2H), 7.72 (m, 1H), 8.07 (s, 1H), 8.14 (s, 1H), 10.65 (s, 1H), 10.99 (s, 1H). M$^-$ (ESI): 440.93; M$^+$ (ESI): 442.73. HPLC (method A), Rt: 3.30 min (purity: 96.6%).

EXAMPLE 34

2'-(acetylamino)-N-[4-(5-hydroxy-1,3,4-oxadiazol-2-yl)phenyl]-4'-methyl-4,5'-bi-1,3-thiazole-2-carboxamide, potassium salt (34)

(34)

2'-Acetylamino-4'-methyl-[4,5']bithiazolyl-2-carbonyl chloride, prepared as in Step I of Example 13, described above, (170.5 mg; 0.56 mmol; 1 eq.), is dissolved in THF (8 ml) and DCM (4 ml). 5-(4-aminophenyl)-1,3,4-oxadiazol-2-ol, Amine 5 obtained as described above, (100.1 mg; 0.56 mmol; 1 eq.) and triethylamine (79 µl; 0.56 mmol; 1 eq.) are added and the mixture is stirred overnight at rt. Solvents are evaporated and the crude product is purified by preparative HPLC. In order to remove any traces of trifluoroacetic acid, the resulting product is dissolved in DCM and an excess of PS-DIEA (Argonaut) is added. The resulting mixture is shaken for 3 hours at rt, filtrated and evaporated, affording compound (34) as parent product (72.5 mg, 29%). HPLC (method A), Rt: 3.30 min (purity: 93.7%). Potassium salt of 2'-(acetylamino)-N-[3-(5-hydroxy-1,3,4-oxadiazol-2-yl)phenyl]-4'-methyl-4,5'-bi-1,3-thiazole-2-carboxamide, Compound (34), is prepared by dissolving the parent compound (72.5 mg; 0.16 mmol; 1 eq.) in THF (3 ml) and water (3 ml). Potassium hydroxide 0.5N solution (3211; 0.50 M; 0.16 mmol; 0.98 eq.) is added. The mixture is stirred 10 min at rt, filtered through cotton and is lyophilized. Potassium salt of compound (34) is isolated as a yellow solid (24.3 mg, 30.9%). $^1$H NMR (DMSO-d$_6$, 300 MHz) δ 1.75 (s, 3H), 2.26 (s, 3H), 3.05 (s, 2H), 6.89 (s, 1H), 7.24 (m, 2H), 7.38 (m, 2H). M$^-$ (ESI): 441.01; M$^+$ (ESI): 443.09. HPLC (method A), Rt: 3.30 min (purity: 99.2%).

EXAMPLE 35

N-[2-(hydroxymethyl)-4'-methyl-4,5'-bi-1,3-thiazol-2'-yl]acetamide (35)

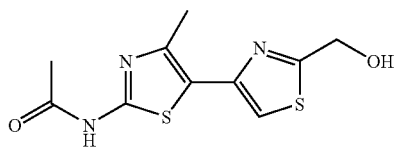

(35)

2'-Acetylamino-4'-methyl-[4,5']bithiazolyl-2-carbonyl chloride, prepared as in Step I of Example 13, described above, (200.5 mg; 0.66 mmol; 1 eq.), is dissolved in DME (7 ml) and is cooled down to −78° C. Lithium tri-tert-butoxyaluminohydride (Aldrich)(2.65 ml; 0.50 M; 1.33 mmol; 2 eq.) is added dropwise. After one hour the reduction is complete. The reaction mixture is poured on ice. The two layers are separated and the organic phase is dried over MgSO$_4$ and concentrated. The resulting product is purified by preparative HPLC, affording Compound (35) as white-off solid (10.5 mg; 6%). $^1$H NMR (DMSO-d$_6$, 300 MHz) δ 2.12 (s, 3H), 2.45 (s, 3H), 4.75 (s, 2H), 7.61 (s, 1H), 12.08 (s, 1H). M$^-$ (ESI): 268.11; M$^+$ (ESI): 270.16. HPLC (method A), Rt: 1.74 min (purity: 100%).

EXAMPLE 36

N-(2-methoxyethyl)-N'-[4'-methyl-2-(morpholin-4-ylcarbonyl)-4,5'-bi-1,3-thiazol-2'-yl]urea (36)

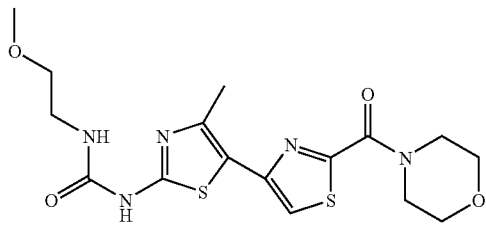

(36)

Step I: Ethyl 2'-amino-4'-methyl-4,5'-bi-1,3-thiazole-2-carboxylate

In a microwave tube, 1-(2-amino-4-methyl-1,3-thiazol-5-yl)-2-bromo ethanone, hydrobromide salt (Intermediate 2)(400 mg; 1.27 mmol; 1 eq.) is suspended in EtOH (7 ml). Ethyl thiooxamate (168.6 mg; 1.27 mmol; 1 eq.) is added and the mixture is heated at 120° C. for 15 min under microwave irradiation. The reaction is complete and a precipitate is formed. It is filtered and washed with EtOH, affording ethyl 2'-amino-4'-methyl-4,5'-bi-1,3-thiazole-2-carboxylate as its hydrobromide salt (201 mg; 45.3%). It is suspended in DCM/EtOH 2:1 mixture (9 ml) and Amberlyst A-21 (200 mg; 4.54 mmol; 3.58 eq.) is added. The mixture is shaken for 2 h30, filtrated and the solvents are evaporated, affording ethyl 2'-amino-4'-methyl-4,5'-bi-1,3-thiazole-2-carboxylate as yellow powder (146.2 mg; 43%). $^1$H NMR (DMSO-d$_6$, 300 MHz) δ 1.33 (t, J=6 Hz, 3H), 2.32 (s, 3H), 4.38 (q, J=6 Hz, 2H), 7.17 (br s, 2H), 7.82 (s, 1H). M$^-$ (ESI): 268.17; M$^+$ (ESI): 270.16. HPLC (method A), Rt: 1.54 min (purity: 99.6%).

Step II: 4'-methyl-2-(morpholin-4-ylcarbonyl)-4,5'-bi-1,3-thiazol-2'-amine, trifluoroacetate salt In a microwave tube, ethyl 2'-amino-4'-methyl-4,5'-bi-1,3-thiazole-2-carboxylate, prepared in Step I described above (188 mg; 0.70 mmol; 1 eq.) is dissolved in morpholine (6 ml). The mixture is heated at 130° C. for 25 min under microwave irradiation. Solvents are evaporated and the crude mixture is purified by preparative HPLC, affording the trifluoroacetate salt of 4'-methyl-2-(morpholin-4-ylcarbonyl)-4,5'-bi-1,3-thiazol-2'-amine as beige powder (171.7 mg; 58%). $^1$H NMR (DMSO-d$_6$, 300 MHz) δ 2.36 (s, 3H), 3.67 (m, 4H), 4.28 (m, 4H), 7.94 (s, 1H), 8.27 (br s, 2H). M$^-$ (ESI): 309.04; M$^+$ (ESI): 311.09. HPLC, Rt: 1.54 min (purity: 99.6%).

Step III: N-[4'-methyl-2-(morpholin-4-ylcarbonyl)-4,5'-bi-1,3-thiazol-2'-yl]-1H-imidazole-1-carboxamide Trifluoroacetate salt of 4'-methyl-2-(morpholin-4-ylcarbonyl)-4,5'-bi-1,3-thiazol-2'-amine, prepared in Step II, described above (142.4 mg; 0.34 mmol; 1 eq.) is suspended in dry DCM (5 ml). CDI (108.8 mg; 0.68 mmol; 2 eq.) and triethylamine (511; 0.37 mmol; 1.10 eq.) are added. Some DMF (0.30 ml) is added to improve the solubility of the starting material. The mixture is stirred overnight at 40° C. A precipitate is formed. It is filtrated, washed with diethyl ether, affording N-[4'-methyl-2-(morpholin-4-ylcarbonyl)-4,5'-bi-1,3-thiazol-2'-yl]-1H-imidazole-1-carboxamide (107.1 mg; 79%) which is used as such in the next step without further purification.

Step IV: N-(2-methoxyethyl)-N'-[4'-methyl-2-(morpholin-4-ylcarbonyl)-4,5'-bi-1,3-thiazol-2'-yl]urea (36)

To N-[4'-methyl-2-(morpholin-4-ylcarbonyl)-4,5'-bi-1,3-thiazol-2'-yl]-1H-imidazole-1-carboxamide, prepared in Step III, described above (50 mg; 0.17 mmol; 1 eq.), is added DMF (2 ml) and 2-methoxyethylamine (Fluka)(16 µl; 0.19 mmol; 1.10 eq.). The mixture is stirred 10 min at rt. Solvents are evaporated and the crude product is crystallized in MeOH, affording Compound (36) as a white-off solid (42.1 mg; 60%). $^1$H NMR (DMSO-d$_6$, 300 MHz) δ 2.41 (s, 3H), 3.30 (m, 5H), 3.39 (m, 2H), 3.68 (m, 6H), 4.33 (m, 2H), 6.67 (m, 1H), 7.91 (s, 1H), 10.41 (br s, 1H). M$^-$ (ESI): 410.09; M$^+$ (ESI): 412.12. HPLC (method A), Rt: 2.41 min (purity: 99.7%).

EXAMPLE 37

Ethyl N-({[4'-methyl-2-(morpholin-4-ylcarbonyl)-4,5-bi-1,3-thiazol-2'-yl]amino}carbonyl)-beta-alaninate (37)

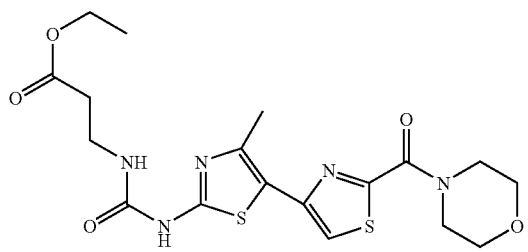

(37)

Trifluoroacetate salt of 4'-Methyl-2-(morpholin-4-ylcarbonyl)-4,5'-bi-1,3-thiazol-2'-amine, prepared as in Step II of Example 36, described above, (150 mg; 0.35 mmol; 1 eq.) is suspended in DCM (5 ml). N,N-Diisopropylethylamine (133 µl; 0.78 mmol; 2.20 eq.) is added. A solution of ethyl 2-isocyanatopropionate (Aldrich)(50.6 mg; 0.35 mmol; 1 eq.) in DCM (3 ml) is added and the resulting mixture is heated at 50° C. overnight. EtOAc is added (10 ml) and the mixture is washed with water. Organic phase is dried over MgSO4 and concentrated. The crude mixture is resubmitted to the same reaction conditions. After one night at 50° C., the conversion is complete and a similar work-up is performed. The crude product is recrystallized in MeOH, affording Compound (37) as white-off powder (92.2 mg; 58%). $^1$H NMR (DMSO-d$_6$, 300 MHz) δ 1.18 (t, J=6 Hz, 3H), 2.41 (s, 3H), 2.50 (m, 2H), 3.36 (m, 2H), 3.68 (m, 6H), 4.07 (q, J=6 Hz, 2H), 4.33 (m, 2H), 6.70 (br s, 1H), 7.90 (s, 1H), 10.52 (br s, 1H). M$^-$ (ESI): 452.14; M$^+$ (ESI): 454.11. HPLC (method A), Rt: 2.89 min (purity: 98.9%).

EXAMPLE 38

N-[2-(1,4-dioxa-8-azaspiro[4.5]dec-8-ylcarbonyl)-4'-methyl-4,5'-bi-1,3-thiazol-2'-yl]acetamide (38)

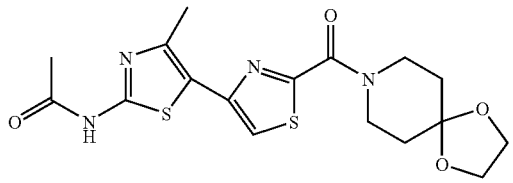

(38)

2'-Acetylamino-4'-methyl-[4,5']bithiazolyl-2-carbonyl chloride, prepared as in Step I of Example 13, described above, (160 mg; 0.53 mmol; 1 eq.), is dissolved in THF (8 ml) and DCM (4 ml). 1,4-Dioxa-8-azaspiro[4.5]decane (Aldrich) (0.06 ml; 0.53 mmol; 1 eq.) and triethylamine (0.15 ml; 1.06 mmol; 2 eq.) are added and the mixture is stirred overnight at rt. Solvents are evaporated and the crude product is purified by precipitation in MeOH, affording Compound (38) as a beige solid (64.9 mg, 30%). $^1$H NMR (DMSO-d$_6$, 300 MHz) δ 1.73 (m, 4H), 2.13 (s, 3H), 2.48 (s, 3H), 3.72 (m, 2H), 3.93 (m, 4H), 4.28 (m, 2H), 7.99 (s, 1H), 12.16 (s, 1H). M$^-$ (ESI): 407.10; M$^+$ (ESI): 409.21. HPLC (method A), Rt: 2.86 min (purity: 94%).

EXAMPLE 39

2'-(acetylamino)-N-(2,3-dihydroxypropyl)-4'-methyl-4,5'-bi-1,3-thiazole-2-carboxamide (39)

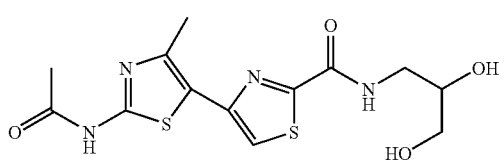

(39)

2'-Acetylamino-4'-methyl-[4,5']bithiazolyl-2-carbonyl chloride, prepared as in Step I of Example 13, described above, (160 mg; 0.53 mmol; 1 eq.), is dissolved in THF (8 ml) and DCM (4 ml). 2,2-Dimethyl-1,3-dioxolane-4-methanamine (Aldrich) (0.07 ml; 0.53 mmol; 1 eq.) and triethylamine (0.15 ml; 1.06 mmol; 2 eq.) are added and the mixture is stirred overnight at rt. Solvents are evaporated and the crude product is purified by preparative HPLC. As some TFA is used for the mobile phase of the preparative HPLC, the diol protecting group is removed during the concentration of the chromatography fractions, affording directly Compound (39) as a white-off solid (26.6 mg; 14%). $^1$H NMR (DMSO-d$_6$, 300 MHz) δ 2.15 (s, 3H), 2.49 (s, 3H), 3.17-3.52 (m, 4H), 3.67 (m, 1H), 4.65 (br s, 1H), 4.93 (br s, 1H), 7.99 (s, 1H), 8.46 (t, J=4.5 Hz, 1H), 12.15 (s, 1H). M$^-$ (ESI): 355.04; M$^+$ (ESI): 356.99. HPLC (method A), Rt: 1.87 min (purity: 100%).

EXAMPLE 40

N-[4'-methyl-2-(morpholin-4-ylcarbonyl)-4,5'-bi-1,3-thiazol-2'-yl]urea (40)

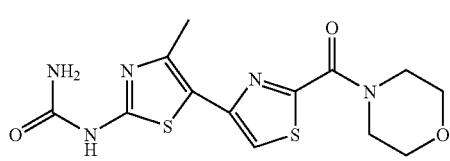

(40)

To N-[4'-methyl-2-(morpholin-4-ylcarbonyl)-4,5'-bi-1,3-thiazol-2'-yl]-1H-imidazole-1-carboxamide, prepared as in Step III of Example 36, described above (535 mg; 1.33 mmol) is added DMF (20 ml) and ammonia 0.5 M solution in dioxane (3.20 ml; 0.50 M; 1.60 mmol; 1.10 eq.). The mixture is stirred at rt overnight. Some ammonia 0.5 M solution in dioxane (1.46 ml; 0.50 M; 0.73 mmol; 0.50 eq.) is added and the mixture is stirred at rt for 5 additional hours. As the reaction is complete, solvents are evaporated. The resulting crude yellow product is purified by preparative HPLC, affording Compound (40) as white-off powder (177 mg; 26%). $^1$H NMR (DMSO-d$_6$, 300 MHz) δ 2.41 (s, 3H), 3.68 (m, 6H), 4.32 (m, 2H), 6.42 (br s, 2H), 7.91 (s, 1H), 10.45 (br s, 1H). M$^-$ (ESI): 352.12; M$^+$ (ESI): 354.11. HPLC (method A), Rt: 2.03 min (purity: 99.7%).

EXAMPLE 41

N-{4'-methyl-2-[(3-oxopiperazin-1-yl)carbonyl]-4,5'-bi-1,3-thiazol-2'-yl}acetamide (41)

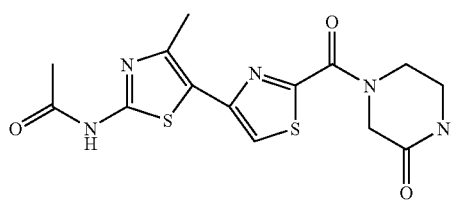

(41)

2'-Acetylamino-4'-methyl-[4,5']bithiazolyl-2-carbonyl chloride, prepared as in Step I of Example 13, described above, (160 mg; 0.53 mmol; 1 eq.), is dissolved in THF (8 ml) and DCM (4 ml). Piperazin-2-one (Aldrich) (63.7 mg; 0.64 mmol; 1.20 eq.) and triethylamine (0.22 ml; 1.59 mmol; 3 eq.)

are added and the mixture is stirred overnight at rt. Solvents are evaporated and the crude product is purified by preparative HPLC, affording Compound (41) as a yellow powder (47.7 mg; 25%). $^1$H NMR (DMSO-d$_6$, 300 MHz) δ 2.14 (s, 3H), 2.48 (s, 3H), 3.25-3.40 (m, 2H), 3.82 (m, 1H), 4.15 (m, 1H), 4.45 (m, 1H), 4.86 (m, 1H), 8.03 (s, 1H), 8.19 (br s, 1H), 12.17 (s, 1H). M$^-$ (ESI): 364.05; M$^+$ (ESI): 365.97. HPLC (method A), Rt: 2.14 min (purity: 99.5%).

EXAMPLE 42

N-{4'-methyl-2-[(4-oxopiperidin-1-yl)carbonyl]-4,5'-bi-1,3-thiazol-2'-yl}acetamide (42)

(42)

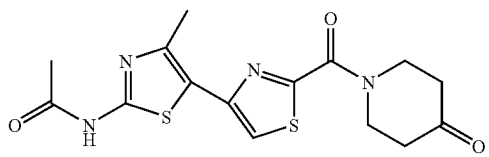

2'-Acetylamino-4'-methyl-[4,5']bithiazolyl-2-carbonyl chloride, prepared as in Step I of Example 13, described above (160 mg; 0.53 mmol; 1 eq.), is dissolved in THF (8 ml) and DCM (4 ml). 4-Piperidone hydrochloride monohydrate (Aldrich) (97.7 mg; 0.64 mmol; 1.20 eq.) and triethylamine (0.22 ml; 1.59 mmol; 3 eq.) are added and the mixture is stirred overnight at rt. Solvents are evaporated and the crude product is purified by preparative HPLC, affording Compound (42) as a pale yellow powder (39.2 mg; 20%). $^1$H NMR (DMSO-d$_6$, 300 MHz) δ 2.14 (s, 3H), 2.49 (s, 3H), 2.53 (m, 4H), 3.94 (m, 2H), 4.53 (m, 2H), 8.03 (s, 1H), 12.17 (s, 1H). M$^-$ (ESI): 363.09; M$^+$ (ESI): 365.04. HPLC (method A), Rt: 2.44 min (purity: 95.3%).

EXAMPLE 43

N-{2-[(3-hydroxypyrrolidin-1-yl)carbonyl]-4'-methyl-4,5'-bi-1,3-thiazol-2'-yl}acetamide (43)

(43)

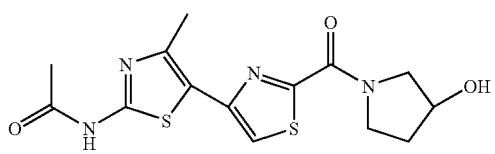

2'-Acetylamino-4'-methyl-[4,5']bithiazolyl-2-carbonyl chloride, prepared as in Step I of Example 13, described above (160 mg, 0.53 mmol, 1 eq.), is dissolved in THF (8 ml) and DCM (4 ml). 3-Pyrrolidinol (Fluka) (55.4 mg; 0.64 mmol; 1.20 eq.) and triethylamine (0.22 ml; 1.59 mmol; 3 eq.) are added and the mixture is stirred overnight at rt. Solvents are evaporated and the crude product is purified by preparative HPLC, affording Compound (43) as a white-off powder (40.1 mg; 21.5%). $^1$H NMR (DMSO-d$_6$, 300 MHz) δ 1.75-2.12 (m, 3H), 2.12 (s, 3H), 2.48 (s, 3H), 3.45-3.70 (m, 2H), 3.90-4.25 (m, 2H), 4.31-4.40 (m, 1H), 5.15 (s, 1H), 12.13 (s, 1H). M$^-$ (ESI): 353.07; M$^+$ (ESI): 351.09. HPLC(method A), Rt: 2.21 min (purity: 99.3%).

EXAMPLE 44

2'-(acetylamino)-4'-methyl-N-prop-2-vn-1-yl-4,5'-bi-1,3-thiazole-2-carboxamide (44)

(44)

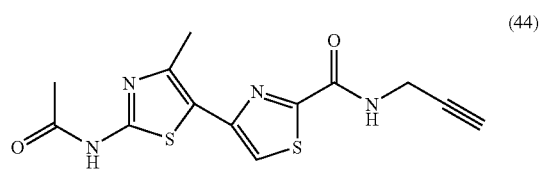

2'-Acetylamino-4'-methyl-[4,5']bithiazolyl-2-carbonyl chloride, prepared as in Step I of Example 13, described above (160 mg, 0.53 mmol, 1 eq.), is dissolved in THF (8 ml) and DCM (4 ml). Propargylamine (Fluka) (35.0 mg; 0.64 mmol; 1.20 eq.) and triethylamine (0.22 ml; 1.59 mmol; 3 eq.) are added and the mixture is stirred overnight at rt. Solvents are evaporated and the crude product is purified by preparative HPLC, affording Compound (44) as a pale yellow powder (83.3 mg; 49%). $^1$H NMR (DMSO-d$_6$, 300 MHz) δ 2.14 (s, 3H), 2.49 (s, 3H), 3.14 (s, 1H, C—CH), 4.04 (m, 2H), 8.01 (s, 1H), 9.20 (t, J=4.5 Hz, 1H), 12.15 (s, 1H). M$^-$ (ESI): 319.05; M$^+$ (ESI): 321.05. HPLC (method A), Rt: 2.71 min (purity: 100%).

EXAMPLE 45

N-{2-[(4-acetylpiperazin-1-yl)carbonyl]-4'-methyl-4,5'-bi-1,3-thiazol-2'-yl}acetamide (45)

(45)

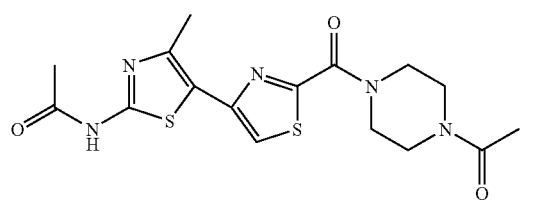

2'-Acetylamino-4'-methyl-[4,5']bithiazolyl-2-carbonyl chloride, prepared as in Step I of Example 13, described above (160 mg, 0.53 mmol, 1 eq.), is dissolved in THF (8 ml) and DCM (4 ml). 1-Acetylpiperazine (Aldrich) (81.5 mg; 0.64 mmol; 1.20 eq.) and triethylamine (0.22 ml; 1.59 mmol; 3 eq.) are added and the mixture is stirred overnight at rt. Solvents are evaporated and the crude product is purified by preparative HPLC, affording Compound (45) as a pale yellow powder (127.9 mg; 61%). $^1$H NMR (DMSO-d$_6$, 300 MHz) δ 2.04 (s, 3H), 2.13 (s, 3H), 2.49 (s, 3H), 3.57 (m, 4H), 3.65 (m, 1H), 3.70 (m, 1H), 4.25 (m, 1H), 4.35 (m, 1H), 8.01 (s, 1H), 12.16 (s, 1H). M$^-$ (ESI): 392.14; M$^+$ (ESI): 394.15. HPLC (method A), Rt: 2.41 min (purity: 100%).

EXAMPLE 46

N,N-dimethyl-N~2~-({[4'-methyl-2-(morpholin-4-ylcarbonyl)-4,5'-bi-1,3-thiazol-2'-yl]amino}carbonyl)glycinamide (46)

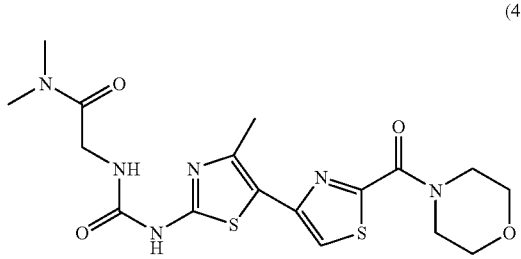
(46)

To N-[4'-methyl-2-(morpholin-4-ylcarbonyl)-4,5'-bi-1,3-thiazol-2'-yl]-1H-imidazole-1-carboxamide, prepared as in Step 3 of Example 36, described above (75 mg; 0.19 mmol; 1 eq.) is added DMF (3 ml), glycine dimethylamide acetate (Chem-Impex) (30.1 mg; 0.19 mmol; 1 eq.) and triethylamine (57 µl; 0.41 mmol; 2.20 eq.). The mixture is stirred 3 hours at rt. Solvents are evaporated and the crude product is crystallized in MeOH, affording Compound (46) as a light yellow solid (49 mg; 60%). $^1$H NMR (DMSO-d$_6$, 300 MHz) δ 2.44 (s, 3H), 2.86 (s, 3H), 2.94 (s, 3H), 3.68 (m, 6H), 4.01 (m, 2H), 4.33 (m, 2H), 6.83 (m, 1H), 7.91 (s, 1H), 10.70 (br s, 1H). M$^-$ (ESI): 437.15; M$^+$ (ESI): 439.09. HPLC (method A), Rt: 2.30 min (purity: 99%).

EXAMPLE 47

N-({[4-methyl-2-(morpholin-4-ylcarbonyl)-4,5'-bi-1,3-thiazol-2'-yl]amino}carbonyl)-beta-alanine (47)

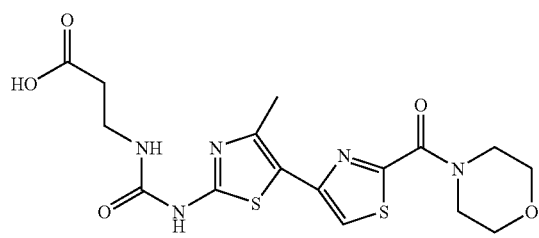
(47)

To N-[4'-methyl-2-(morpholin-4-ylcarbonyl)-4,5'-bi-1,3-thiazol-2'-yl]-1H-imidazole-1-carboxamide, prepared as in Step 3 of Example 36, described above (75 mg; 0.19 mmol; 1 eq.), is added DMF (3 ml), Beta-alanine (Aldrich) (18.2 mg; 0.20 mmol; 1.10 eq.) and triethylamine (57 µl; 0.41 mmol; 2.20 eq.). The mixture is stirred 3 days at rt. Solvents are evaporated and the crude product is crystallized in MeOH, affording Compound (47) as a light yellow solid (17 mg; 22%). $^1$H NMR (DMSO-d$_6$, 300 MHz) δ 2.41 (s, 3H), 2.49 (m, 4H), 3.31 (m, 6H), 4.33 (m, 2H), 6.71 (br s, 1H), 7.90 (s, 1H), 10.47 (br s, 1H), 12.34 (br s, 1H). M$^-$ (ESI): 424.03; M$^+$ (ESI): 426.08. HPLC (method A), Rt: 2.20 min (purity: 98%).

EXAMPLE 48

N-{2-[(4-fluoropiperidin-1-yl)carbonyl]-4'-methyl-4,5'-bi-1,3-thiazol-2'-yl}acetamide (48)

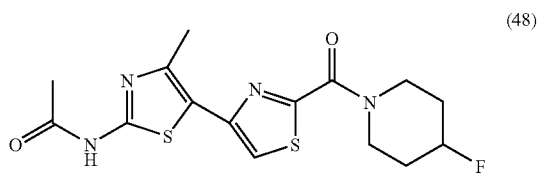
(48)

2'-Acetylamino-4'-methyl-[4,5']bithiazolyl-2-carbonyl chloride, prepared as in Step I of Example 13, described above (200 mg, 0.66 mmol, 1 eq.), is dissolved in THF (8 ml) and DCM (4 ml). 4-Fluoropyperidine (Flrochem) (95.7 mg; 0.92 mmol; 1.40 eq.) and triethylamine (0.37 ml; 2.65 mmol; 4 eq.) are added and the mixture is stirred overnight at rt. Solvents are evaporated and the crude product is purified by preparative HPLC, affording Compound (48) as a white-off powder (36 mg; 13%). $^1$H NMR (DMSO-d$_6$, 300 MHz) δ 1.71-2.12 (m, 4H), 2.16 (s, 3H), 2.50 (s, 3H), 3.75 (m, 2H), 4.33 (m, 2H), 4.97 (ttd, J=3, 6, 51 Hz, 1H, —CFH), 8.02 (s, 1H), 12.19 (s, 1H). M$^-$ (ESI): 367.13; M$^+$ (ESI): 369.12. HPLC (method A), Rt: 3.04 min (purity: 95.8%).

EXAMPLE 49

N-(2-{[(1S,5S,7S)-7-(hydroxymethyl)-6,8-dioxa-3-azabicyclo[3.2.1]oct-3-yl]carbonyl}-4'-methyl-4,5'-bi-1,3-thiazol-2'-yl)acetamide (49)

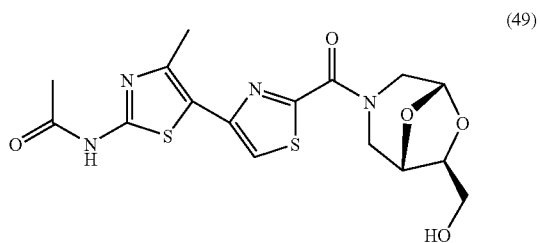
(49)

2'-Acetylamino-4'-methyl-[4,5']bithiazolyl-2-carbonyl chloride, prepared as in Step I of Example 13, described above (200 mg, 0.66 mmol, 1 eq.), is dissolved in THF (8 ml) and DCM (4 ml). (1S,5S,7S)-6,8-dioxa-3-azabicyclo[3.2.1]oct-7-ylmethanol, synthesized according the literature (Guarna et al *J. Org. Chem.* 1999, 64, 7347) (96.2 mg; 0.66 mmol; 1 eq.), and triethylamine (0.37 ml; 2.65 mmol; 4 eq.) are added and the mixture is stirred 1 hour at rt. Solvents are evaporated and the crude product is purified by preparative HPLC, affording Compound (49) as a white-off powder (73 mg; 26%). M$^-$ (ESI): 409.16; M$^+$ (ESI): 411.07. HPLC (method A), Rt: 2.16 min (purity: 95.46%).

EXAMPLE 50 ethyl N-({[2-(cyanomethyl)-4'-methyl-4,5'-bi-1,3-thiazol-2'-yl]amino}carbonyl)-beta-alaninate (50)

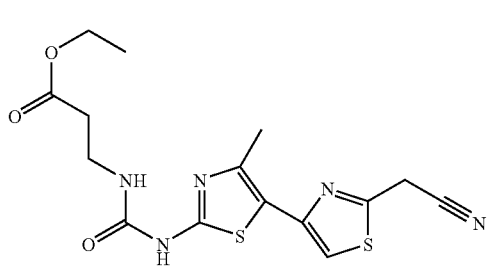

(50)

Step I: (2'-amino-4'-methyl-4,5'-bi-1,3-thiazol-2-yl) acetonitrile 1-(2-Amino-4-methyl-1,3-thiazol-5-yl)-2-bromo ethanone, hydrobromide salt (Intermediate 2) (116.97 mg; 0.50 mmol; 1 eq.) and 2-cyanothioacetamide (Aldrich) (50.1 mg; 0.50 mmol; 1 eq.) are dissolved in EtOH (5 ml). The mixture is stirred at rt overnight. Solvents are evaporated, affording a yellow-orange solid which is purified by flash chromatography (CHCl$_3$/EtOH gradient, from 50:1 to 10:1). (2'-amino-4'-methyl-4,5'-bi-1,3-thiazol-2-yl)acetonitrile is isolated as an orange solid. (71.6 mg; 61%). $^1$H NMR (DMSO-d$_6$, 300 MHz) δ 2.41 (s, 3H), 4.62 (s, 2H), 7.87 (s, 1H), 9.23 (br s, 2H). M$^-$ (ESI): 235.04; M$^+$ (ESI): 237.06. HPLC (method A), Rt: 1.16 min (purity: 98.3%).

Step II: Ethyl N-({[2-(cyanomethyl)-4'-methyl-4,5'-bi-1,3-thiazol-2'-yl]amino}carbonyl)-beta-alaninate (50)

(2'-Amino-4'-methyl-4,5'-bi-1,3-thiazol-2-yl)acetonitrile, prepared in Step I, described above (236.3 mg; 1 mmol; 1 eq.), is suspended in DCM (5 ml). N,N-Diisopropylethylamine (377 µl; 2.20 mmol; 2.20 eq.) is added, followed by a solution of ethyl 3-isocyanatopropionate (143.1 mg; 1 mmol; 1 eq.) in DCM (3 ml). The reaction mixture is heated at 50° C. overnight. As the reaction is not complete, a second batch of ethyl 3-isocyanatopropionate (Aldrich) (143.1 mg; 1 mmol; 1 eq.) is added. After 36 hours the reaction is complete. The solvents are evaporated. EtOAc is added and the mixture is washed with brine, dried over MgSO$_4$ and evaporated. The resulting crude product is purified by preparative HPLC, affording Compound (50) as white-off solid (76.6 mg; 20%). $^1$H NMR (DMSO-d$_6$, 300 MHz) δ 1.21 (t, J=7.5 Hz, 3H), 2.44 (s, 3H), 2.58 (m, 2H), 3.39 (q, J=6 Hz, 2H), 4.10 (q, J=7.5 Hz, 2H), 4.62 (s, 2H), 6.72 (t, J=6 Hz, 1H), 7.64 (s, 1H), 10.49 (br s, 1H). M$^-$ (ESI): 378.17; M$^+$ (ESI): 380.10. HPLC (method A), Rt: 2.60 min (purity: 100%).

EXAMPLE 51

N-(2-{[(1R,5R,7R)-7-(hydroxymethyl)-6,8-dioxa-3-azabicyclo[3.2.1]oct-3-yl]carbonyl}-4'-methyl-4,5'-bi-1,3-thiazol-2'-yl)acetamide (51)

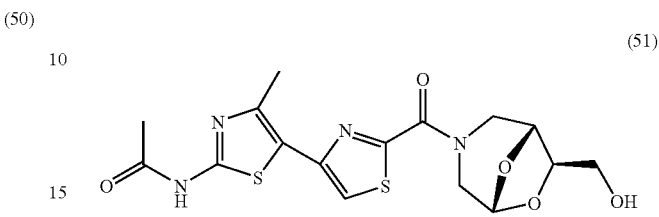

(51)

2'-Acetylamino-4'-methyl-[4,5']bithiazolyl-2-carbonyl chloride, prepared as in Step I of Example 13, described above (200 mg, 0.66 mmol, 1 eq.), is dissolved in THF (8 ml) and DCM (4 ml). (1R,5R,7R)-6,8-Dioxa-3-azabicyclo[3.2.1]oct-7-ylmethanol, synthesized according the literature (Guarna et al., 1999, *J. Org. Chem.*, 64, 7347) (96.2 mg; 0.66 mmol; 1 eq.), and triethylamine (0.37 ml; 2.65 mmol; 4 eq.) are added and the mixture is stirred 1 hour at rt. Solvents are evaporated and the crude product is purified by preparative HPLC, affording Compound (51) as a white-off powder (110 mg; 40%). M$^-$ (ESI): 408.99; M$^+$ (ESI): 410.89. HPLC (method A), Rt: 2.15 min (purity: 99.8%).

EXAMPLE 52 tert-butyl N-({[2-(cyanomethyl)-4'-methyl-4,5'-bi-1,3-thiazol-2'-yl]amino}carbonyl)-beta-alaninate (52)

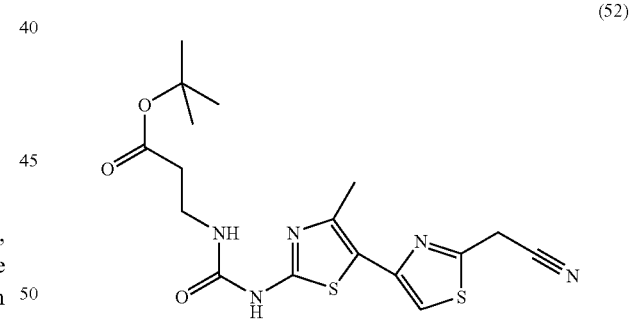

(52)

Step I: N-[2-(cyanomethyl)-4'-methyl-4,5'-bi-1,3-thiazol-2'-yl]-1H-imidazole-1-carboxamide Triethylamine (0.65 ml; 4.69 mmol; 1.49 eq.) is added to a suspension of (2'-amino-4'-methyl-4,5'-bi-1,3-thiazol-2-yl) acetonitrile (1 000 mg; 3.15 mmol; 1 eq.) and CDI (1 372.3 mg; 8.46 mmol; 2.68 eq.) in dry DCM (65 ml). DMF (4 ml) is added and the mixture is heated at 45° C. for one night. The reaction is cooled down to rt. The resulting precipitate is filtered and washed with Et$_2$O, affording N-[2-(cyanomethyl)-4'-methyl-4,5'-bi-1,3-thiazol-2'-yl]-1H-imidazole-1-carboxamide, which is used in the next step without further purification (822.8 mg; 79%).

Step II: tert-butyl N-({[2-(cyanomethyl)-4'-methyl-4,5'-bi-1,3-thiazol-2'-yl]amino}carbonyl)-beta-alaninate (52)

To N-[2-(cyanomethyl)-4'-methyl-4,5'-bi-1,3-thiazol-2'-yl]-1H-imidazole-1-carboxamide, obtained in Step I, as described above (160 mg; 0.48 mmol; 1 eq.), is added DMF (8 ml),
-alanine t-butyl ester hydrochloride (Bachem) (87.9 mg; 0.48 mmol; 1 eq.) and triethylamine (148 µl; 1.07 mmol; 2.20 eq.). After 15 min at rt, the solvents are evaporated and the resulting crude product is purified by preparative HPLC. NaHCO$_3$ saturated solution (250 ml) is added to the purified fractions and the desired product is extracted with DCM (3×100 ml). Organic phases are dried over MgSO$_4$ and the solvents are evaporated. Compound (52) is obtained as beige solid (92.8 mg; 47%). $^1$H NMR (DMSO-d$_6$, 300 MHz) δ 1.40 (s, 9H), 2.41 (m, 5H), 3.33 (m, 2H), 4.59 (s, 2H), 6.63 (t, J=6 Hz, 1H), 7.61 (s, 1H), 10.48 (br s, 1H). M$^-$ (ESI): 406.23; M$^+$ (ESI): 407.94. HPLC (method A), Rt: 3.17 min (purity: 99.8%).

EXAMPLE 53

[4'-methyl-2'-(pyrazin-2-ylamino)-4,5'-bi-1,3-thiazol-2-yl]acetonitrile (53)

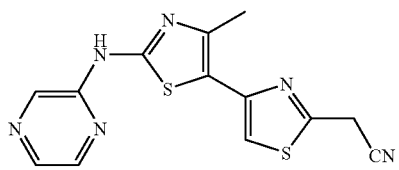

(53)

To a solution of 2-bromo-1-[4-methyl-2-(pyrazin-2-ylamino)-1,3-thiazol-5-yl]ethanone, (Intermediate 3) (75 mg; 0.19 mmol; 1 eq.) in EtOH (2 ml), is added triethylamine (66 µl; 0.48 mmol; 2.50 eq.) and 2-cyanothioacetamide (19.0 mg; 0.19 mmol; 1 eq.). The mixture is stirred overnight at rt. The reaction mixture is filtered and rinsed -with ethanol affording Compound (53) as brown solid (35.4 mg; 59%). $^1$H NMR (DMSO-d$_6$) δ2.49 (s, 3H), 4.62 (s, 2H), 7.67 (s, 1H), 8.13 (m, 1H), 8.36 (m, 1H), 8.44 (m, 1H), 11.79 (br s, 1H). M$^{31}$ (ESI): 312.88; M$^+$(ESI): 314.95. HPLC (method A), Rt: 2.47 min (purity: 93.5%).

EXAMPLE 54 ethyl 4'-methyl-2'-(pyrazin-2-ylamino) 4,5'-bi-1,3-thiazole-2-carboxylate (54)

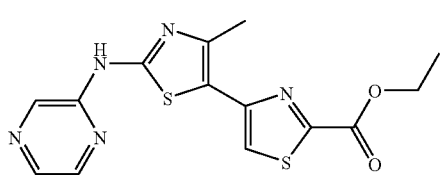

(54)

To a solution of 2-bromo-1-[4-methyl-2-(pyrazin-2-ylamino)-1,3-thiazol-5-yl]ethanone, (Intermediate 3) (75 mg; 0.19 mmol; 1 eq.) in EtOH (2 ml) is added ethyl thiooxamate (25.3 mg; 0.19 mmol; 1 eq.). The mixture is heated at 100° C. for 10 min. The solvents are evaporated, and the crude product is suspended in EtOH, filtered and dried under vacuo. It is dissolved in THF (1ml) and DCM (1 ml) mixture, and PS-DIEA (Argonaut) (27.3 mg; 0.10 mmol; 0.75 eq.) is added. After 15 min shaking at rt, the mixture is filtered and the solvents are evaporated, affording Compound (54) as a brown solid (45.6 mg; 69%). $^1$H NMR (DMSO-d$_6$) δ 1.17 (t, J=6 Hz, 3H), 2.51 (s, 3H), 4.42 (q, J =6 Hz, 2H), 8.07 (s, 1H), 8.15 (d, J =2.6 Hz, 1H), 8.38 (dd, J =1.1, 2.6 Hz, 1H), 8.45 (d, J =1.1 Hz, 1H), 11.88 (br s, 1H). M$^-$(ESI): 346.13; M$^+$(ESI): 348.10. HPLC (method A), Rt: 3.03 min (purity: 94.0%).

EXAMPLE 55

[4'-methyl-2'-(1H-pyrazol-3-ylamino)-4,5'-bi-1,3-thiazol-2-yl]acetonitrile (55)

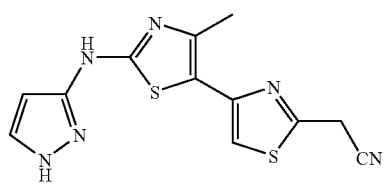

(55)

To a solution of 1-{2-[(1-acetyl-1H-pyrazol-3-yl)amino]-4-methyl-1,3-thiazol-5-yl}-2-bromoethanone, (Intermediate 4) (150 mg; 0.35 mmol; 1 eq.) in EtOH (5 ml) is added 2-cyanothioacetamide (35.4 mg; 0.35 mmol; 1 eq.). The resulting mixture is heated 10 min at 60° C., 10 min at 70° C. and 10 min at 80° C. under microwave action. As the reaction is complete, Et$_2$O is added. The resulting precipitate is filtered and washed with Et$_2$O, affording Compound (55) as beige solid (84.1 mg; 62%). $^1$H NMR (DMSO-d$_6$) δ 2.46 (s, 3H), 4.61 (s, 2H), 6.01 (d, J=2 Hz, 1H), 7.65 (s, 1H), 7.72 (d, J=2 Hz, 1H), 11.26 (br s, 1H). M$^-$ (ESI): 301.13; M$^+$ (ESI): 303.14. HPLC (method A), Rt: 1.84 min (purity: 92.7%).

EXAMPLE 56

N-[4'-methyl-2-(2-morpholin-4-yl-2-oxoethyl)-4,5'-bi-1,3-thiazol-2'-yl]acetamide (56)

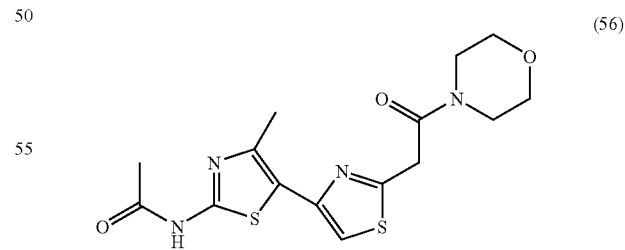

(56)

N-[5-(bromoacetyl)-4-methyl-1,3-thiazol-2-yl]acetamide, hydrobromide salt (Intermediate 1) (300 mg; 0.84 mmol; 1 eq) and 3-morpholin-4-yl-3-thioxo-propionamide (157.7 mg; 0.84 mmol; 1 eq) are dissolved in EtOH (10 ml). Triethylamine (0.29 ml; 2.09 mmol; 2.5 eq) is added. The mixture is stirred overnight at RT. Solvents are evaporated and the crude product is dissolved in EtOAc and washed with water, brine and dried over MgSO$_4$. After filtration and evaporation of the solvents, the resulting yellow solid is dissolved in a DCM, Et$_2$O and EtOH mixture. Concentration of this solution results in the precipitation of Compound (56) as yellow solid (126.2 mg; 41%)

$^1$H NMR (DMSO-d$_6$, 300 MHz) δ 2.35 (s, 3H), 2.69 (s, 3H), 3.7-3.81 (m, 8H), 4.47 (s, 2H), 7.83 (s, 1H), 12.29 (br s, 1H). M$^-$ (ESI): 365.3; M$^+$ (ESI): 367.3. HPLC (method A), Rt: 2.21 min (purity: 93.8%).

EXAMPLE 57

N',2-(4'-methyl-4,5'-bi-1,3-thiazole-2,2'-diyl)diacetamide (57)

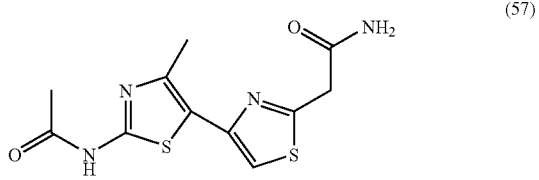

(57)

N-[5-(bromoacetyl)-4-methyl-1,3-thiazol-2-yl]acetamide, hydrobromide salt (Intermediate 1) (300 mg; 0.84 mmol; 1 eq) and 2-thiocarbamoyl-acetamide (99 mg; 0.84 mmol; 1 eq) are dissolved in EtOH (10 ml). Triethylamine (0.29 ml; 2.09 mmol; 2.5 eq) is added. The mixture is stirred overnight at RT. Solvents are evaporated and the crude product is dissolved in EtOAc and washed with water, brine and dried over MgSO$_4$. After filtration and evaporation of the solvents, the resulting crude product is purified by flash chromatography (DCM/MeOH 20/1), affording Compound (57) as an orange solid (6.1 mg; 3%).

$^1$H NMR (DMSO-d$_6$, 300 MHz) δ 2.22 (s, 3H), 2.55 (s, 3H), 3.99 (s, 2H), 7.27 (br s, 1H), 7.67 (s, 1H), 7.80 (br s, 1H), 12.15 (br s, 1H). M$^-$ (ESI): 295.2; M$^+$ (ESI): 297.2. HPLC (method A), Rt: 1.67 min (purity: 95.9%).

EXAMPLE 58 tert-Butyl 4-{[2-(cyanomethyl)-4'-methyl-4,5'-bi-1,3-thiazol-2'-yl]amino}-4-oxobutanoate (58)

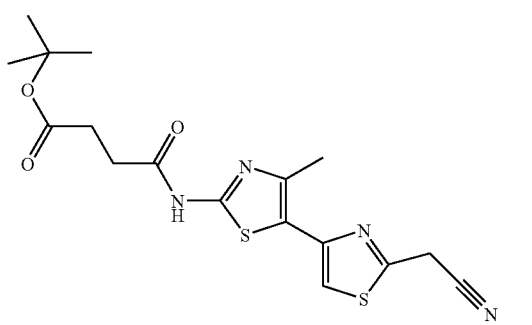

(58)

2-Amino-4-methyl-[4,5]bisthiazolyl-2-yl)-acetonitrile (Intermediate 5) (100 mg; 0.42 mmol; 1 eq.) is dissolved in anhydrous THF (10 ml). The solution is put under nitrogen. TBTU (203.8 mg; 0.63 mmol; 1.5 eq), succinic acid mono-tert-butyl ester (184.3 mg; 1.06 mmol; 2.5 eq) and DIEA (144 μl; 0.85 mmol; 2 eq) are added successively and the reaction mixture is stirred 2 days at RT. Solvents are evaporated and the crude mixture is dissolved in DCM. The organic layer is washed with NH$_4$Cl sat. (twice) and then brine. It is dried over MgSO$_4$ and the solvents are removed under vacuum. The crude product is purified by preparative HPLC, affording Compound (58) as a white solid (85.6 mg; 51%).

$^1$H NMR (DMSO-d$_6$, 300 MHz) δ 1.36 (s, 9H), 2.26 (s, 3H), 2.55 (t, 2H), 2.63 (t, 2H), 4.60 (s, 2H), 7.71 (s, 1H), 12.16 (s, 1H). M$^-$ (ESI): 391.29; M$^+$ (ESI): 393.33. HPLC (method A), Rt: 3.55 min (purity: 100%).

EXAMPLE 59

Methyl 5-{[2-(cyanomethyl)-4'-methyl-4,5'-bi-1,3-thiazol-2'-yl]amino}-5-oxopentanoate (59)

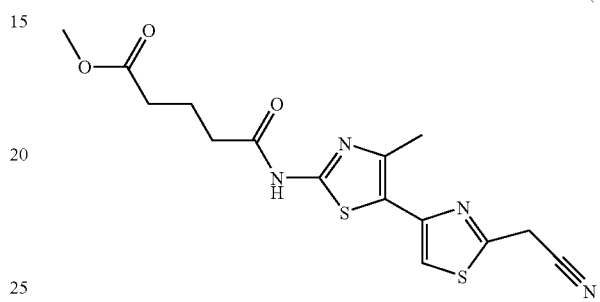

(59)

2-Amino-4-methyl-[4,5]bisthiazolyl-2-yl)-acetonitrile (Intermediate 5) (100 mg; 0.42 mmol; 1 eq.) is dissolved in anhydrous THF (10 ml). The resulting solution is put under nitrogen. TBTU (203.8 mg; 0.63 mmol; 1.5 eq), pentanedioic acid monomethyl ester (154.6 mg; 1.06 mmol; 2.5 eq) and DIEA (144.0 μL; 0.85 mmol; 2 eq) are added successively and the reaction mixture is stirred for 2 days at RT. Solvents are evaporated and the crude product is dissolved in DCM. The organic layer is washed with NH$_4$Cl sat. (twice) and brine. It is dried over MgSO$_4$ and the solvents are removed under vacuum. The crude product is then purified by preparative HPLC, affording Compound (59) as a white solid (78.8 mg; 51%).

$^1$H NMR (DMSO-d$_6$, 300 MHz) δ 1.81 (q, 2H), 2.35 (t, 2H), 2.48 (s, 3H), 2.48 (t, 2H), 4.61 (s, 2H), 7.71 (s, 1H), 12.12 (s, 1H). M$^-$ (ESI): 363.3; M$^+$ (ESI): 365.2. HPLC (method A), Rt: 2.89 min (purity: 99.07%).

EXAMPLE 60

Methyl 6-{[2-(cyanomethyl)-4'-methyl-4,5'-bi-1,3-thiazol-2'-yl]amino}-6-oxohexanoate (60)

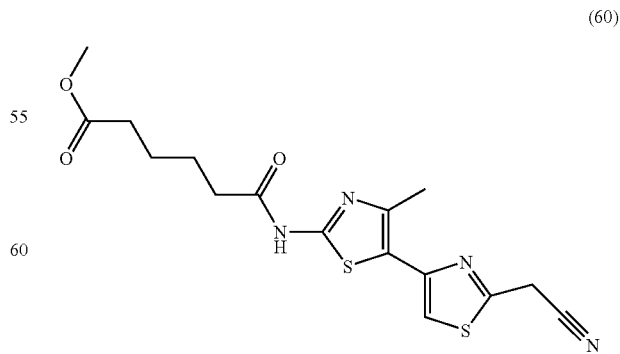

(60)

2-Amino-4-methyl-[4,5]bisthiazolyl-2-yl)-acetonitrile (Intermediate 5) (100 mg; 0.42 mmol; 1 eq.) is dissolved in anhydrous THF (10 ml). The resulting solution is put under nitrogen. TBTU (203.8 mg; 0.63 mmol; 1.5 eq), hexanedioic acid monomethyl ester (169.4 mg; 1.06 mmol; 2.5 eq) and DIEA (144 μl; 0.85 mmol; 2 eq) are added successively and the reaction mixture is stirred for 2 days at RT. Solvents are evaporated and the crude product is dissolved in DCM. The organic layer is washed with NH$_4$Cl sat. (twice) and brine. It is dried over MgSO$_4$ and the solvents are removed under vacuum. The crude product is then purified by preparative HPLC, affording Compound (60) as a beige solid (76.5 mg; 48%).

$^1$H NMR (DMSO-d$_6$, 300 MHz) δ 1.32 (m, 4H), 2.08 (t, 2H), 2.20 (t, 2H), 2.26 (s, 3H), 3.35 (s, 3H), 4.38 (s, 2H), 7.48 (s, 1H), 11.88 (s, 1H) M$^-$ (ESI): 377.3; M$^+$ (ESI): 379.3. HPLC (method A), Rt: 3.12 min (purity: 99.47%).

EXAMPLE 61

2'-(Acetylamino)-N,N,4'-trimethyl-4,5'-bi-1,3-thiazole-2-carboxamide (61)

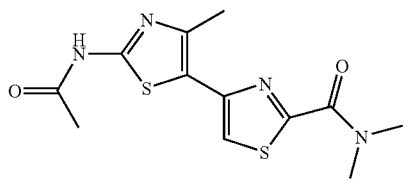

(61)

2'-Acetylamino-4'-methyl-[4,5']bithiazolyl-2-carbonyl chloride, prepared as in Step I of Example 13, described above, (110 mg; 0.36 mmol; 1 eq.) is dissolved in anhydrous THF (10 ml). Under nitrogen, dimethylamine (0.27 ml; 0.55 mmol; 1.5 eq) and triethylamine (0.08 ml; 0.55 mmol; 1.5 eq) are added. The reaction mixture is stirred at RT for 1 hour. The solvents are evaporated and the crude product is directly purified by preparative HPLC, affording Compound (61) as a white-off solid (65.0 mg; 57%).

$^1$H NMR (DMSO-d$_6$, 300 MHz) δ 2.13 (s, 3H), 2.49 (s, 3H), 3.06 (s, 3H), 3.54 (s, 3H), 7.97 (s, 1H), 12.14 (s, 1H). M$^-$ (ESI): 309.2; M$^+$ (ESI): 311.2. HPLC (method A), Rt: 2.49 min (purity: 99.52%).

EXAMPLE 62

2'-(Acetylamino)-4'-methyl-4,5'-bi-1,3-thiazole-2-carboxamide (62)

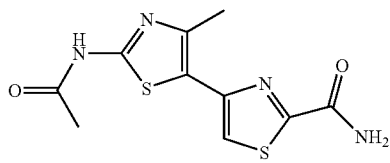

(62)

2'-Acetylamino-4'-methyl-[4,5']bithiazolyl-2-carbonyl chloride, prepared as in Step I of Example 13, described above, (110 mg; 0.36 mmol; 1 eq.), is dissolved in anhydrous THF (10 ml). Under nitrogen, triethylamine (0.08 ml; 0.55 mmol; 1.5 eq) is added. Ammonia (gas) is bubbled during 10 minutes. The flask is closed and the reaction mixture is stirred for 20 additional minutes at RT. The solvents are removed and the crude product is directly purified by preparative HPLC, affording Compound (62) as a white-off solid (25.6 mg; 22%).

$^1$H NMR (DMSO-d$_6$, 300 MHz) δ 2.13 (s, 3H), 2.49 (s, 3H), 7.95 (d, 2H), 8.06 (s, 1H), 12.12 (s, 1H). M$^-$ (ESI): 281.1; M$^+$ (ESI): 283.1. HPLC (method A), Rt: 2.10 min (purity: 88.54%).

EXAMPLE 63

4-{[2-(cyanomethyl)-4'-methyl-4,5'-bi-1,3-thiazol-2'-yl]amino}-4-oxobutanoic acid (63)

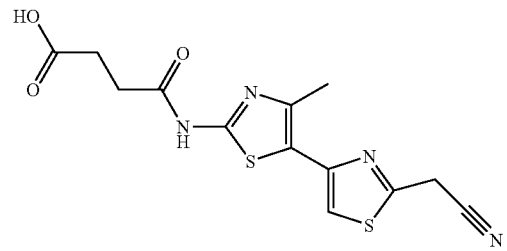

(63)

Tert-butyl 4-{[2-(cyanomethyl)-4'-methyl-4,5'-bi-1,3-thiazol-2'-yl]amino}-4-oxobutanoate, Compound (58), (63 mg; 0.16 mmol; 1 eq.), is dissolved in DCM (3 ml). Trifluoroacetic acid (0.16 ml; 2.09 mmol; 13 eq) is added dropwise and the reaction mixture is stirred at RT. The solvents are evaporated and the crude product is purified by preparative HPLC, affording Compound (63) as a white-off solid (54 mg; 29%).

$^1$H NMR (DMSO-d$_6$, 300 MHz) δ 2.55 (s, 2H), 2.66 (m, 2H), 4.60 (s, 2H), 7.70 (s, 1H), 12.15 (s, 2H). M$^-$ (ESI): 335.17; M$^+$ (ESI): 337.2. HPLC (method A), Rt: 2.11 min (purity: 99.89%).

EXAMPLE 64

5-{[2-cyanomethyl)-4'-methyl-4,5'-bi-1,3-thiazol-2'-yl]amino}-5-oxopentanoic acid (64)

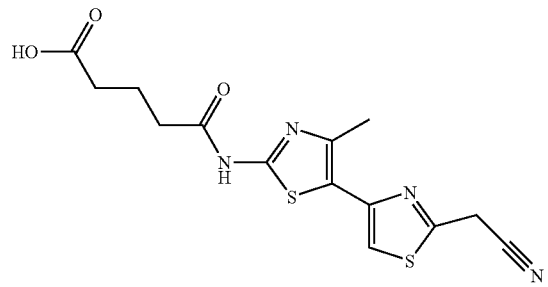

(64)

Methyl 5-{[2-(cyanomethyl)-4'-methyl-4,5'-bi-1,3-thiazol-2'-yl]amino}-5-oxopentanoate, Compound (59), (78 mg; 0.21 mmol; 1 eq.), is dissolved in THF (12 ml) and water (3 ml). Lithium hydroxide monohydrate (18 mg; 0.43 mmol, 2 eq) is added and the reaction mixture is stirred at RT for 20 minutes. It is then acidified with HCl 1N. After evaporation of the solvents, the resulting crude product is purified by preparative HPLC, affording Compound (64) as a white-off solid (5.5 mg; 8%).

$^1$H NMR (DMSO-d$_6$, 300 MHz) δ 1.78 (t, 2H), 2.26 (t, 2H), 2.46 (t, 2H), 4.61 (s, 2H), 7.70 (s, 1H), 12.10 (s, 2H). M$^-$ (ESI): 349.20; M$^+$ (ESI): 351.18. HPLC (method A), Rt: 2.28 min (purity: 100%).

EXAMPLE 65 tert-butyl N-({[2-(cyanomethyl)-4'-methyl-4,5'-bi-1,3-thiazol-2'-yl]amino}carbonyl)glycinate

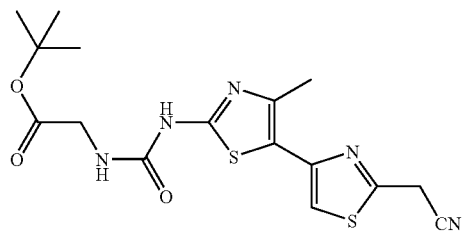

(65)

N-[2-(cyanomethyl)-4'-methyl-4,5'-bi-1,3-thiazol-2'-yl]-1H-imidazole-1-carboxamide (Intermediate 6) (160 mg; 0.48 mmol; 1 eq) is dissolved in DMF (8 ml). A solution of glycine tert-butyl ester (63.5 mg; 0.48 mmol; 1 eq) in DMF (1 ml) and triethylamine (74 µl; 0.53 mmol; 1.10 eq) are added. After less than 1 min the mixture becomes homogeneous. After 45 min, the reaction is complete. DMF is removed under reduced pressure to afford 235.8 mg of a dark brown solid, which is purified by preparative HPLC. The purified fractions are neutralized with NaHCO$_3$ sat. solution and the desired product is extracted with DCM. The combined organic layers are dried over MgSO$_4$, filtered and concentrated, affording Compound (65) as a brown solid (27.30 mg; 14%).

$^1$H NMR (DMSO-d$_6$, 300 MHz) δ 1.48 (s, 9H), 2.55 (s, 3H), 4.03 (d, J=6 Hz, 2H), 4.12 (s, 2H), 7.19 (s, 1H). HPLC (method A), Rt 3.05 min (purity: 100%). M$^-$ (ESI): 392.2.

EXAMPLE 66 tert-butyl 4-[({[2-(cyanomethyl)-4'-methyl-4,5'-bi-1,3-thiazol-2'-yl]amino}carbonyl)amino]butanoate

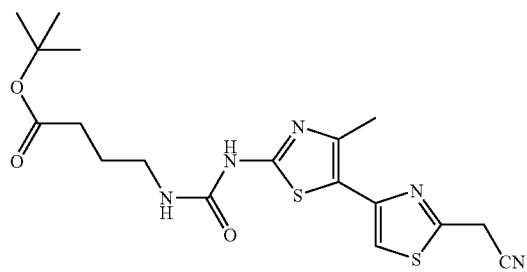

(66)

N-[2-(cyanomethyl)-4'-methyl-4,5'-bi-1,3-thiazol-2'-yl]-1H-imidazole-1-carboxamide (Intermediate 6) (160 mg; 0.48 mmol; 1 eq) is dissolved in DMF (8 ml). Tert-butyl 4-aminobutanoate hydrochloride (94.8 mg; 0.48 mmol; 1 eq) and triethylamine (148 µl; 1.07 mmol; 2.20 eq) are added. After less than 1 min, the mixture becomes homogeneous. After 30 min the reaction is complete. DMF is removed under reduced pressure. The resulting crude oil is dissolved in DCM and washed twice with NH$_4$Cl sat. solution and twice with NaHCO$_3$ sat. solution. The organic layer is dried over Na$_2$SO$_4$, filtered and concentrated. The resulting crude product is purified by preparative HPLC. The purified fractions are neutralized with NaHCO$_3$ sat. solution and the desired compound is extracted with DCM.

The combined organic layers are dried over MgSO$_4$, filtered and concentrated, affording Compound (66) as a slightly kaki powder (84.1 mg; 41%).

$^1$H NMR (DMSO-d$_6$, 300 MHz) δ 1.39 (s, 9H), 1.66 (m, 2H), 2.21 (t, J=7.5 Hz, 2H), 2.41 (s, 3H), 3.13 (m, 2H), 4.59 (s, 2H), 6.59 (m, 1H), 7.61 (s, 1H), 10.36 (br s, 1H). HPLC (method A), Rt 3.41 min (purity: 100%). M$^-$ (ESI): 420.3.

EXAMPLE 67

N~2~-({[2-(cyanomethyl)-4'-methyl-4,5'-bi-1,3-thiazol-2'-yl]amino}carbonyl)-N,N-dimethylglycinamide

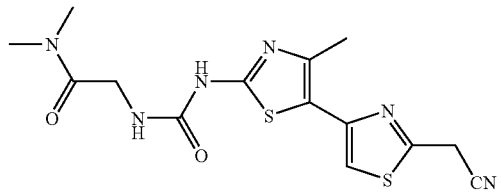

(67)

N-[2-(cyanomethyl)-4'-methyl-4,5'-bi-1,3-thiazol-2'-yl]-1H-imidazole-1-carboxamide (Intermediate 6) (160 mg; 0.48 mmol; 1 eq) is dissolved in DMF (7 ml). A solution of N,N-dimethylglycinamide acetate (78.5 mg; 0.48 mmol; 1 eq) in DMF (0.50 ml) and triethylamine (148 µl; 1.07 mmol; 2.20 eq) are added. After less than 1 min the mixture becomes homogeneous, and after 1 h the reaction is complete. DMF is removed under reduced pressure to afford a dark brown oil, which is purified by preparative HPLC. The purified fractions are neutralized with NaHCO$_3$ sat. solution and the desired compound is extracted with DCM. The combined organic layers are dried over MgSO$_4$, filtered and concentrated, affording Compound (67) as a beige solid (67.6 mg; 37%).

$^1$H NMR (DMSO-d$_6$, 300 MHz) δ 2.42 (s, 3H), 2.86 (s, 3H), 2.94 (s, 3H), 4.01 (d, J=6 Hz, 2H), 4.59 (s, 2H), 6.84 (m, 1H), 7.61 (s, 1H), 10.66 (br s, 1H). HPLC (method A), Rt 2.16 min (purity: 97.32%). M$^-$ (ESI): 363.23; M$^+$ (ESI): 365.21.

EXAMPLE 68 tert-butyl N-({[4'-methyl-2-(morpholin-4-ylcarbonyl)-4,5'-bi-1,3-thiazol-2'-yl]amino}carbonyl)-beta-alaninate (68)

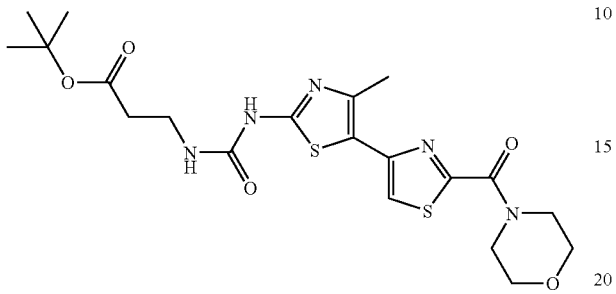

N-[4'-methyl-2-(morpholin-4-ylcarbonyl)-4,5'-bi-1,3-thiazol-2'-yl]-1H-imidazole-1-carboxamide (Intermediate 7) (160 mg; 0.40 mmol; 1 eq) is dissolved in DMF (8 ml). Tert-butyl beta-alaninate hydrochloride (71.9 mg; 0.40 mmol; 1 eq) and triethylamine (121 µl; 0.87 mmol; 2.20 eq) are added. After less than 1 min the mixture becomes homogeneous, and after 45 min the reaction is complete. DMF is removed under reduced pressure, affording a yellow oil. It is recrystallized in MeOH, affording Compound (68) as a yellow solid (159.1 mg; 83%).

$^1$H NMR (DMSO-$d_6$, 300 MHz) δ 1.40 (s, 9H), 2.41 (m, 5H), 3.33 (m, 2H), 3.68 (m, 6H), 4.33 (m, 2H), 6.64 (m, 1H), 7.90 (s, 1H), 10.52 (br s, 1H). HPLC (method A), Rt 3.45 min (purity: 99.84%). M$^-$ (ESI): 480.37; M$^+$ (ESI): 482.42.

EXAMPLE 69

N-[4'-methyl-2-(morpholin-4-ylcarbonyl)-4,5'-bi-1,3-thiazol-2'-yl]-N-(2-morpholin-4-yl-2-oxoethyl)urea (69)

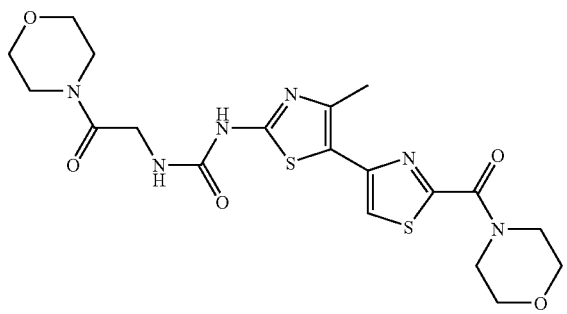

N-[4'-methyl-2-(morpholin-4-ylcarbonyl)-4,5'-bi-1,3-thiazol-2'-yl]-1H-imidazole-1-carboxamide (Intermediate 7) (160 mg; 0.40 mmol; 1 eq) is dissolved DMF (7 ml). A solution of 2-amino-1-morpholin-4-yl-ethanone (57.0 mg; 0.40 mmol; 1 eq) in DMF (0.50 ml) and triethylamine (60 µl; 0.44 mmol; 1.10 eq) are added. After 1 h15, the reaction is complete. DMF is removed under reduced pressure, affording a white solid, which is purified by preparative HPLC. The purified fractions are neutralized with NaHCO$_3$ sat. solution and the desired compound is extracted with DCM. The combined organic layers are dried over MgSO$_4$, filtered and concentrated, affording Compound (69) as a white-off solid (103.7 mg; 55%).

$^1$H NMR (DMSO-$d_6$, 300 MHz) δ 2.36 (s, 3H), 3.43 (m, 4H), 3.57 (m, 4H), 3.68 (m, 6H), 4 (d, J=3 Hz, 2H), 4.36 (m, 2H), 6.95 (br s, 1H), 7.68 (s, 1H). HPLC (method A), Rt 2.36 min(purity: 97.41%). M$^-$ (ESI): 479.31; M$^+$ (ESI): 481.29.

EXAMPLE 70

N-[2-(cyanomethyl)-4'-methyl-4,5'-bi-1,3-thiazol-2'-yl]-N-(2-morpholin-4-yl-2-oxoethyl)urea (70)

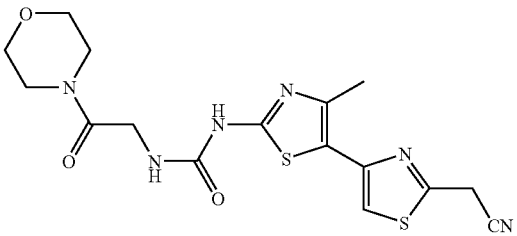

N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) is dissolved in DMF (5 ml). 2-Amino-1-morpholin-4-yl-ethanone (43.6 mg; 0.30 mmol; 1 eq) and triethylamine (46 µl; 0.33 mmol; 1.10 eq) are added. After 20 min the reaction is complete. DMF is removed under reduced pressure, affording a brown oil. It is recrystallized in MeOH, affording Compound (70) as a beige powder (54.5 mg; 44%).

$^1$H NMR (DMSO-$d_6$, 300 MHz) δ 2.42 (s, 3H), 3.41 (m, 2H), 3.46 (m, 2H), 3.57 (m, 4H), 4.05 (d, J=3 Hz, 2H), 4.59 (s, 2H), 6.85 (m, 1H), 7.61 (s, 1H), 10.67 (br s, 1H). HPLC (method A), Rt 2.07 min (purity: 93.78%). M$^-$ (ESI): 405.22; M$^+$ (ESI): 407.16.

EXAMPLE 71 methyl N-({[2-(cyanomethyl)-4'-methyl-4,5'-bi-1,3-thiazol-2'-yl]amino}carbonyl)-beta-alaninate (71)

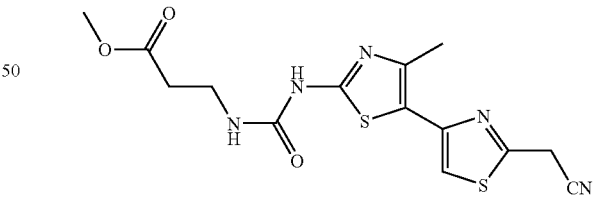

N-[2-(cyanomethyl)-4'-methyl-4,5'-bi-1,3-thiazol-2'-yl]-1H-imidazole-1-carboxamide (Intermediate 6) (330 mg; 1 mmol; 1 eq) is dissolved in DMF (15 ml). Beta-alanine methyl ester hydrochloride (139.4 mg; 1 mmol; 1 eq) and triethylamine (305 µl; 2.20 mmol; 2.20 eq) are added. After less than 15 min the mixture becomes homogeneous, and after 20 min the reaction is complete. DMF is removed under reduced pressure, affording a brown oil. It is dissolved in DCM and washed twice with NH$_4$Cl sat. solution. The combined organic layers are dried over Na$_2$SO$_4$, filtered and concentrated to give Compound (71) as a brown solid (296.2 mg; 81%).

¹H NMR (DMSO-d₆, 300 MHz) δ 2.41 (s, 3H), 2.53 (m, 2H), 3.36 (m, 2H), 3.61 (s, 3H), 4.59 (s, 2H), 6.70 (m, 1H), 7.61 (s, 1H), 10.44 (br s, 1H). HPLC (method A), Rt 2.41 min (purity: 94.04%). M⁻ (ESI): 364.21; M⁺ (ESI): 366.19.

EXAMPLE 72

N~3~-({[2-(cyanomethyl)-4'-methyl-4,5'-bi-1,3-thiazol-2'-yl]amino}carbonyl)-N,N-diisopropyl-beta-alaninamide (72)

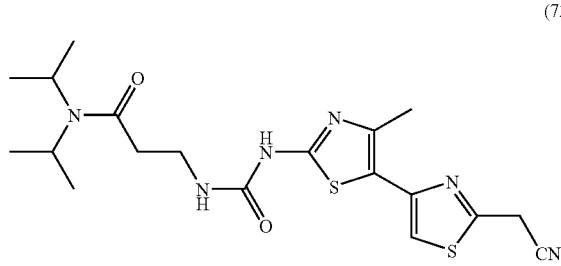

N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) is dissolved in DMF (5 ml). N,N-diisopropyl-beta-alaninamide (Amine 6) (86.7 mg; 0.30 mmol; 1 eq) and triethylamine (92 µl; 0.67 mmol; 2.20 eq) are added. After 20 min the reaction is complete. DMF is removed under reduced pressure, affording a colorless oil, which is purified by preparative HPLC. The purified fractions are neutralized with NaHCO₃ sat. solution and the desired product is extracted with DCM. The combined organic layers are dried over MgSO₄, filtered and concentrated, affording Compound (72) as a white solid (79.8 mg; 61%)

¹H NMR (DMSO-d₆, 300 MHz) δ 1.18 (d, J=6 Hz, 6H), 1.36 (d, J=6 Hz, 6H), 2.50 (s, 3H), 2.58 (t, J=6 Hz, 2H), 3.49 (m, 1H), 3.63 (m, 2H), 3.93 (m, 1H), 4.12 (s, 2H), 7.14 (s, 1H), 7.35 (br s, 1H). HPLC (method A), Rt 3.16 min (purity: 99.68%). M⁻ (ESI): 433.30; M⁺ (ESI): 435.35.

EXAMPLE 73

N~3~-({[2-(cyanomethyl)-4'-methyl-4,5'-bi-1,3-thiazol-2'-yl]amino}carbonyl)-N-(2-hydroxy-1,1-dimethylethyl)-beta-alaninamide (73)

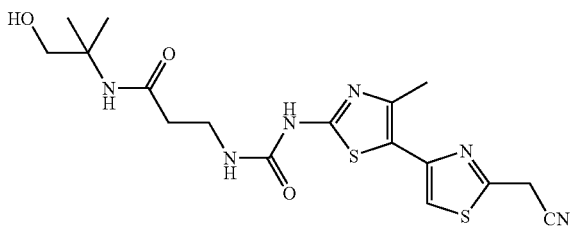

N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) is dissolved in DMF (5 ml). N-(2-hydroxy-1,1-dimethylethyl)-beta-alaninamide (Amine 7) (91.3 mg; 0.33 mmol; 1.10 eq) and triethylamine (92 µl; 0.67 mmol; 2.20 eq) are added. After 20 min, the reaction is complete and DMF is removed under reduced pressure to afford an orange oil, which is purified by preparative HPLC. The purified fractions are neutralized with NaHCO₃ sat. solution and the desired product is extracted with DCM. The combined organic layers are dried over MgSO₄, filtered and concentrated, affording Compound (73) as a white solid (74.8 mg; 58%).

¹H NMR (DMSO-d₆, 300 MHz) δ 1.17 (s, 6H), 2.28 (t, J=6 Hz, 2H), 2.41 (s, 3H), 3.28 (m, 2H), 3.38 (d, J=6 Hz, 2H), 4.59 (s, 2H), 4.81 (m, 1H), 6.64 (m, 1H), 7.36 (br s, 1H), 7.60 (s, 1H), 10.42 (br s, 1H). HPLC (method A), Rt 2.20 min (purity: 100%).

EXAMPLE 74

N-(tert-butyl)-N~3~-({[2-(cyanomethyl)-4'-methyl-4,5'-bi-1,3-thiazol-2'-yl]amino}carbonyl)-beta-alaninamide (74)

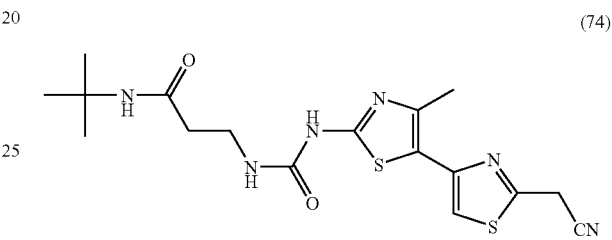

N-(tert-butyl)-beta-alaninamide (Amine 8) (93.8 mg; 0.36 mmol; 1.20 eq) is dissolved in DMF (5 ml). Triethylamine (126 µl; 0.91 mmol; 3 eq) and N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) are added. After less than 1 min the mixture becomes homogeneous, and after 45 min the reaction is complete. The solvents are evaporated and the resulting crude product is purified by preparative HPLC. The purified fractions are neutralized with NaHCO₃ sat. solution and the desired product is extracted with DCM. The combined organic layers are dried over MgSO₄, filtered and concentrated, affording Compound (74) as a white solid (53 mg; 43%).

¹H NMR (DMSO-d₆, 300 MHz) δ 1.31 (s, 9H), 1.71 (br s, 1H), 2.46 (t, J=6 Hz, 2H), 2.50 (s, 3H), 3.61 (m, 2H), 4.12 (s, 2H), 5.74 (br s, 1H), 7.16 (s, 1H), 7.56 (br s, 1H). HPLC (method A), Rt 2.62 min (purity: 99.77%). M⁻ (ESI): 405.31; M⁺ (ESI): 407.34.

EXAMPLE 75

N-[2-(cyanomethyl)-4'-methyl-4,5'-bi-1,3-thiazol-2'-yl]-N-[3-(2,2-dimethyl-1,3-thiazolidin-3-yl)-3-oxopropyl]urea (75)

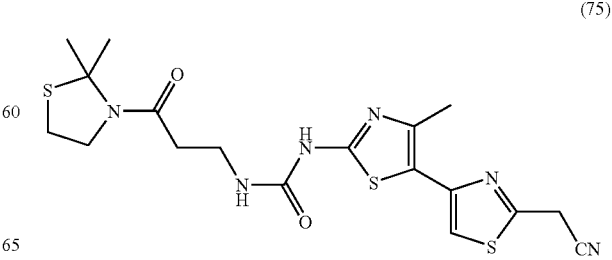

3-(2,2-Dimethyl-1,3-thiazolidin-3-yl)-3-oxopropan-1-amine (Amine 9) (43.9 mg; 0.15 mmol; 1.20 eq) is dissolved in DMF (3 ml). Triethylamine (50 µl; 0.36 mmol; 3 eq) and N-[2-(cyanomethyl)-4'-methyl-4,5'-bi-1,3-thiazol-2'-yl]-1H-imidazole-1-carboxamide (Intermediate 6) (40 mg; 0.12 mmol; 1 eq) are added. After 20 min the reaction is complete and solvents are evaporated. The resulting colorless oil is purified by preparative HPLC. The purified fractions are neutralized with NaHCO₃ sat. solution and the desired product is extracted with DCM. The combined organic layers are dried over MgSO₄, filtered and concentrated, affording Compound (75) as a beige solid (31.9 mg; 58%).

$^1$H NMR (DMSO-d$_6$, 300 MHz) δ 1.81 (s, 6H), 2.51 (s, 3H), 2.57 (m, 2H), 2.97 (t, J=6 Hz, 2H), 3.62 (m, 2H), 3.84 (t, J=6 Hz, 2H), 4.12 (s, 2H), 7.16 (s, 1H), 7.47 (br s, 1H). HPLC (method A), Rt 2.96 min (purity: 91.70%). M⁻ (ESI): 449.27; M⁺ (ESI): 451.35.

EXAMPLE 76

N-[2-(cyanomethyl)-4'-methyl-4,5'-bi-1,3-thiazol-2'-yl]-N-[3-(4,4-dimethyl-1,3-oxazolidin-3-yl)-3-oxopropyl]urea

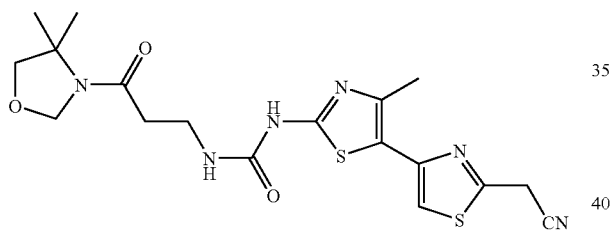

(76)

3-(4,4-Dimethyl-1,3-oxazolidin-3-yl)-3-oxopropan-1-amine (Amine 10) (104 mg; 0.36 mmol; 1.20 eq) is dissolved in DMF (5 ml). Triethylamine (126 µl; 0.91 mmol; 3 eq) and N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) are added. After 20 min the reaction is complete. DMF is removed under reduced pressure to afford a colorless oil, which is purified by preparative HPLC. The purified fractions are neutralized with NaHCO₃ sat. solution and the desired product is extracted with DCM. The combined organic layers are dried over MgSO₄, filtered and concentrated, affording Compound (76) as a beige solid (71.3 mg; 54%).

$^1$H NMR (DMSO-d$_6$, 300 MHz) δ 1.43 (s, 6H, minor rotamer), 1.47 (s, 6H, major rotamer), 2.43 (t, J=6 Hz, 2H, major rotamer), 2.51 (s, 3H), 2.70 (t, J=6 Hz, 2H, minor rotamer), 3.64 (m, 2H), 3.72 (s, 2H, major rotamer), 3.79 (s, 2H, minor rotamer), 4.12 (s, 2H), 4.94 (s, 2H, major rotamer), 5.13 (s, 2H, minor rotamer), 7.16 (s, 1H), 7.51 (br s, 1H). HPLC (method A), Rt 2.51 min (purity: 99.82%). M⁻ (ESI): 433.29; M⁺ (ESI): 435.33.

EXAMPLE 77

N~2~-({[2-(cyanomethyl)-4'-methyl-4,5'-bi-1,3-thiazol-2'-yl]amino}carbonyl)-N-(2,2-dimethylpropyl)glycinamide

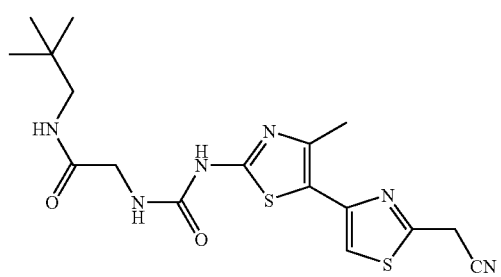

(77)

N-(2,2-dimethylpropyl)glycinamide (Amine 11) (93.8 mg; 0.36 mmol; 1.20 eq) is dissolved in DMF (5 ml). Triethylamine (126 µl; 0.91 mmol; 3 eq) and N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) are added. After less than 15 min the mixture becomes homogeneous, and after 20 min the reaction is complete. Solvents are evaporated and the resulting crude product is purified by preparative HPLC. The purified fractions are neutralized with NaHCO₃ sat. solution and the desired product is extracted with DCM. The combined organic layers are dried over MgSO₄, filtered and concentrated, affording Compound (77) as a slightly purple powder (83.8 mg; 68%).

$^1$H NMR (DMSO-d$_6$, 300 MHz) δ 0.83 (s, 9H), 2.42 (s, 3H), 2.92 (d, J=6 Hz, 2H), 3.82 (d, J=6 Hz, 2H), 4.59 (s, 2H), 6.81 (t, J=6 Hz, 1H), 7.61 (s, 1H), 7.89 (t, J=6 Hz, 1H), 10.58 (br s, 1H). HPLC (method A), Rt 2.81 min (purity: 100%). M⁻ (ESI): 405.30; M⁺ (ESI): 407.32.

EXAMPLE 78

N-(3-azocan-1-yl-3-oxopropyl)-N-[2-(cyanomethyl)-4'-methyl-4,5'-bi-1,3-thiazol-2'-yl]urea

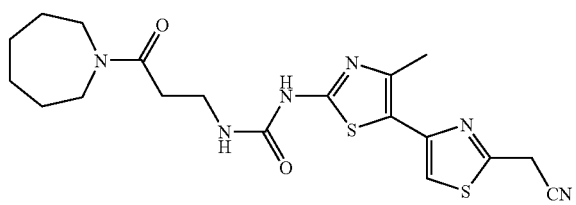

(78)

3-Azocan-1-yl-3-oxopropan-1-amine (Amine 12) (108.3 mg; 0.36 mmol; 1.20 eq) is dissolved in DMF (5 ml). Triethylamine (126 µl; 0.91 mmol; 3 eq) and N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) are added. After less than 15 min the mixture becomes homogeneous, and after 20 min the reaction is complete. Solvents are evaporated and the resulting crude product is purified by preparative HPLC. The purified fractions are neutralized with NaHCO₃ sat. solution and the desired product is extracted with DCM. The combined organic layers are dried over MgSO₄, filtered and concentrated, affording Compound (78) as a slight green solid (106.3 mg; 79%).

$^1$H NMR (DMSO-d$_6$, 300 MHz) δ 1.45 (m, 6H), 1.62 (m, 4H), 2.40 (s, 3H), 2.52 (m, 2H), 3.36 (m, 6H), 4.59 (s, 2H), 6.72 (m, 1H), 7.60 (s, 1H), 10.44 (br s, 1H). HPLC (method A), Rt 3.13 min (purity: 100%) M⁻ (ESI): 445.35; M⁺ (ESI): 447.40.

EXAMPLE 79

N-[2-(cyanomethyl)-4'-methyl-4,5'-bi-1,3-thiazol-2'-yl]-N'-[2-(1-isopropyl-1H-imidazol-4-yl)ethyl]urea

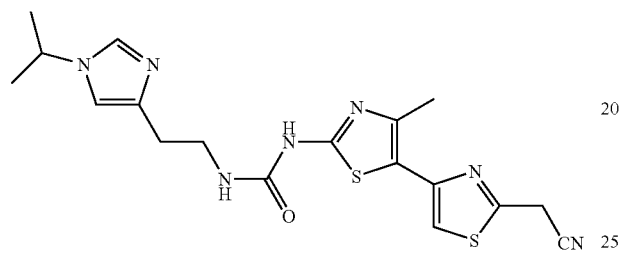

(79)

2-(1-Isopropyl-1H-imidazol-4-yl)ethanamine (Amine 13) (57 mg; 0.25 mmol; 1.20 eq) is dissolved in DMF (5 ml). Triethylamine (116 µl; 0.84 mmol; 4 eq) and N-[2-(cyanomethyl)-4'-methyl-4,5'-bi-1,3-thiazol-2'-yl]-1H-imidazole-1-carboxamide (Intermediate 6) (69.4 mg; 0.21 mmol; 1 eq) are added. After less than 15 min the mixture becomes homogeneous, and after 45 min the reaction is complete. DMF is removed under reduced pressure, affording a brown oil, which is purified by flash chromatography (DCM/MeOH, gradient from 10/0 to 9/1 over 25 min). Compound (79) is isolated as a beige solid (12.3 mg; 14%).

$^1$H NMR (DMSO-d$_6$, 300 MHz) δ 1.36 (d, J=6 Hz, 6H), 2.41 (s, 3H), 2.61 (t, J=6 Hz, 2H), 3.37 (m, 2H), 4.32 (sept, J=6 Hz, 1H), 4.59 (s, 2H), 6.62 (m, 1H), 7.01 (m, 1H), 7.58 (m, 1H), 7.60 (s, 1H), 10.46 (br s, 1H). HPLC (method A), Rt 2.02 min (purity: 99.26%). M⁻ (ESI): 414.36; M⁺ (ESI): 416.40.

EXAMPLE 80

N-[2-(cyanomethyl)-4'-methyl-4,5'-bi-1,3-thiazol-2'-yl]-N'-[2-(1-ethyl-1H-imidazol-4-yl)ethyl]urea (80)

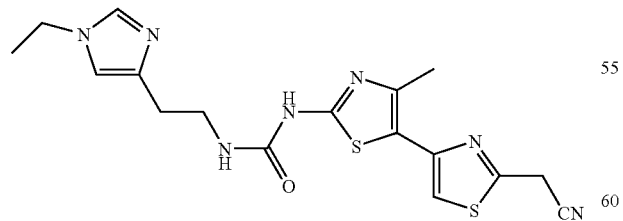

2-(1-Ethyl-1H-imidazol-4-yl)ethanamine (Amine 14) (77 mg; 0.36 mmol; 1.20 eq) is dissolved in DMF (5 ml). Triethylamine (168 µl; 1.21 mmol; 4 eq) and N-[2-(cyanomethyl)-4'-methyl-4,5'-bi-1,3-thiazol-2'-yl]-1H-imidazole-1-carboxamide (Intermediate 6) (100 mg; 0.30 mmol; 1 eq) are added. After less than 15 min the mixture becomes homogeneous, and after 45 min the reaction is complete. DMF is removed under reduced pressure, affording a brown oil, which is purified by flash chromatography (DCM/MeOH, gradient from 10/0 to 9/1 over 25 min). Compound (80) is isolated as beige solid (23.5 mg; 19%).

$^1$H NMR (DMSO-d$_6$, 300 MHz) δ 1.31 (t, J=6 Hz, 3H), 2.41 (s, 3H), 2.61 (t, J=6 Hz, 2H), 3.37 (m, 2H), 3.92 (q, J=6 Hz, 2H), 4.59 (s, 2H), 6.62 (m, 1H), 6.95 (m, 1H), 7.54 (d, J=3 Hz, 1H), 7.60 (s, 1H), 10.44 (br s, 1H). HPLC (method A), Rt 1.87 min (purity: 98.07%).

EXAMPLE 81

N-[2-(5-tert-butyl-1,2,4-oxadiazol-3-yl)ethyl]-N'-[2-(cyanomethyl)-4'-methyl-4,5-bi-1,3-thiazol-2'-yl] urea (81)

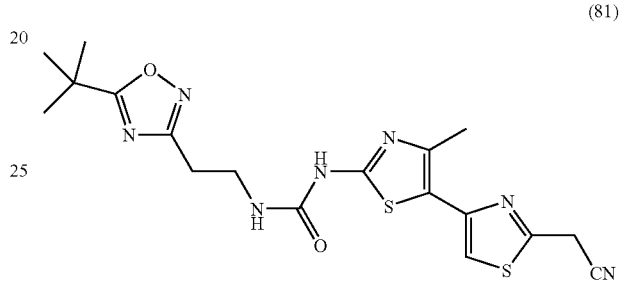

2-(5-Tert-butyl-1,2,4-oxadiazol-3-yl)ethanamine (Amine 15) (136 mg; 0.48 mmol; 2 eq) is dissolved in DMF (4 ml). Triethylamine (133 µl; 0.96 mmol; 4 eq) and N-[2-(cyanomethyl)-4'-methyl-4,5'-bi-1,3-thiazol-2'-yl]-1H-imidazole-1-carboxamide (Intermediate 6) (79.3 mg; 0.24 mmol; 1 eq) are added. After less than 1 min the mixture becomes homogeneous, and after 30 min the reaction is complete. Solvents are evaporated and the resulting crude product is purified by preparative HPLC. The purified fractions are neutralized with NaHCO₃ sat. solution and the desired product is extracted with DCM. The combined organic layers are dried over MgSO₄, filtered and concentrated, affording Compound (81) as a beige powder (32.5 mg; 31%).

$^1$H NMR (DMSO-d$_6$, 300 MHz) δ 1.36 (s, 9H), 2.41 (s, 3H), 2.88 (T, J=6 Hz, 2H), 3.49 (m, 2H), 4.59 (s, 2H), 6.71 (m, 1H), 7.61 (s, 1H), 10.53 (br s, 1H). HPLC (method A), Rt 3.15 min (purity: 99.4%). M⁻ (ESI): 430.35; M⁺ (ESI): 432.40.

EXAMPLE 82

N-[2-(cyanomethyl)-4'-methyl-4,5'-bi-1,3-thiazol-2'-yl]-N'-[2-(5-isopropyl-1,2,4-oxadiazol-3-yl)ethyl] urea (82)

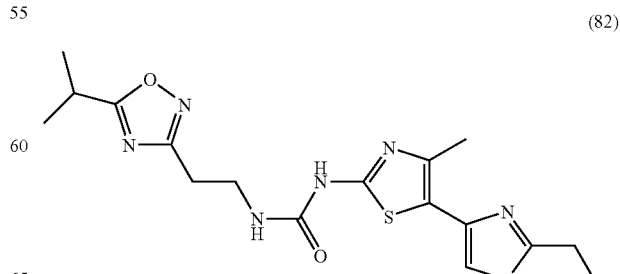

2-(5-Isopropyl-1,2,4-oxadiazol-3-yl)ethanamine (Amine 16) (129.2 mg; 0.48 mmol; 2 eq) is dissolved in DMF (4 ml). Triethylamine (133 µl; 0.96 mmol; 4 eq) and N-[2-(cyanomethyl)-4'-methyl-4,5'-bi-1,3-thiazol-2'-yl]-1H-imidazole-1-carboxamide (Intermediate 6) (79.3 mg; 0.24 mmol; 1 eq) are added. After less than 1 min the mixture becomes homogeneous, and after 30 min the reaction is complete. Solvents are evaporated and the resulting crude product is purified by preparative HPLC. The purified fractions are neutralized with NaHCO$_3$ sat. solution and the desired product is extracted with DCM. The combined organic layers are dried over MgSO$_4$, filtered and concentrated to Compound (82) as a white powder (29.6 mg; 30%).

$^1$H NMR (DMSO-d$_6$, 300 MHz) δ 1.30 (d, J=6 Hz, 6H), 2.41 (s, 3H), 2.88 (t, J=6 Hz, 2H), 3.24 (m, 1H), 3.49 (m, 2H), 4.59 (s, 2H), 6.71 (br s, 1H), 7.61 (s, 1H), 10.52 (br s, 1H). HPLC (method A), Rt 2.94 min (purity: 91.6%). M$^-$ (ESI): 416.33; M$^+$ (ESI): 418.36.

EXAMPLE 83

N-(4'-methyl-2-{[5-(1-methylpiperidin-4-yl)-1,2,4-oxadiazol-3-yl]methyl}-4,5'-bi-1,3-thiazol-2'-yl)acetamide (83)

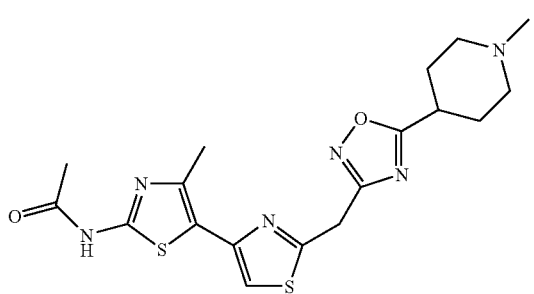

(83)

Step I: N-{2-[(2E)-2-amino-2-(hydroxyimino)ethyl]-4'-methyl-4,5'-bi-1,3-thiazol-2'-yl}acetamide N-[2-(cyanomethyl)-4'-methyl-4,5'-bi-1,3-thiazol-2'-yl]acetamide, Compound (3) (50 mg; 0.18 mmol; 1 eq.), is dissolved in dioxane (10 ml). Hydroxylamine hydrochloride (15 mg; 0.22 mmol; 1.20 eq.) and N,N-diethylethanamine (0.03 ml; 0.22 mmol; 1.20 eq.) are added and reaction mixture is heated at 80° C. overnight. Reaction mixture is cooled down and dioxane evaporated. The residue is taken up in EtOAc and washed several times with water (3×10 mL). The organic phases are dried over MgSO$_4$, filtrated and evaporated. Crude material is purified by flash chromatography on silica gel (cyclohexane/ethylacetate, 50/50), affording the title compound as an oil (50 mg; 95%).

$^1$H NMR (DMSO-d$_6$, 300 MHz) δ 2.10 (s, 3H), 2.45 (s, 3H), 3.72 (m, 1H), 5.62 (m, 2H), 7.51 (s, 1H), 9.10 (m, 1H). M$^-$ (ESI): 310.2; M$^+$ (ESI): 312.2. HPLC (method A), Rt: 1.38 min (purity: 81.1%).

Step II: N-(4'-methyl-2-{[5-(1-methylpiperidin-4-yl)-1,2,4-oxadiazol-3-yl]methyl}-4,5'-bi-1,3-thiazol-2'-yl)acetamide (83)

N-{2-[(2E)-2-amino-2-(hydroxyimino)ethyl]-4'-methyl-4,5'-bi-1,3-thiazol-2'-yl}acetamide, obtained in step I as describe above (45 mg; 0.14 mmol; 1 eq.), is dissolved in DMF (3 ml) at RT. N-Methyl-4-piperidine carboxylic acid (102 mg; 0.72 mmol; 5 eq.), pre-activated with 1-ethyl-3-(3-dimethylaminopropyl)carbodiimide hydrochloride (138.5 mg; 0.72 mmol; 5 eq.) in DCM (3 ml), is added into the reaction mixture. It is stirred for 3 hours at RT. Upon completion of the reaction, water (1 ml) is added and solvents are concentrated to dryness. The residue is taken up in EtOAc and washed several times with water (3×5 mL). The organic phases are dried over MgSO$_4$, filtrated and evaporated. Residue is directly taken up in pyridine (3 mL) and heated up at 90° C. for 12 hours. Reaction mixture is cooled down and pyridine is evaporated to dryness. The crude material is purified by flash chromatography on silica gel (cyclohexane/ethylacetate, 10/90), affording Compound (83) as an oil (30 mg; 66%).

$^1$H NMR (DMSO-d$_6$, 300 MHz) δ 1.90 (m, 2H), 2.10 (s, 3H), 2.30 (m, 2H), 2.40 (s, 3H), 2.75 (s, 3H), 3.10 (m, 2H), 3.40 (m, 1H), 3.50 (m, 2H), 4.60 (s, 2H), 7.66 (s, 1H), 9.50 (m, 1H), 12.10 (m, 1H). M$^-$ (ESI): 417.5; M$^+$ (ESI): 419.5. HPLC (method A), Rt: 1.96 min (purity: 86.9%).

EXAMPLE 56

Biological Assays

The compounds of the present invention may be subjected to the following assays:

a) High Throughput PI3K Lipid Kinase Assay (Binding Assay):

The efficacy of compounds of the invention in inhibiting the PI3K induced-lipid phosphorylation may be tested in the following binding assay.

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 µl of the test compound of Formula (I) (solubilized in 6% DMSO; to yield a concentration of 100, 30, 10, 3, 1, 0.3, 0.1, 0.03, 0.01, 01 µM of the test compound), the following assay components are added. 1) 5 µl (58 ng) of Human recombinant GST-PI3Kγ (in Hepes 40 mM, pH 7.4, DTT 1 mM and ethylenglycol 5%) 2) 10 µl of lipid micelles and 3) 10 µl of Kinase buffer ([$^{33}$P]γ ATP. 45 µM/60 nCi, MgCl mM, DTT 1 mM, β Glycerophosphate 1 mM, NVO$_4$ 100 µM, Na Cholate 0.3%, in Hepes 40 mM, pH 7.4). After incubation at room temperature for 180 minutes, with gentle agitation, the reaction is stopped by addition of 60 µl of a solution containing 100 µg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table I below refer to the IC$_{50}$ (µM) with respect to PI3Kγ, i.e. the amount necessary to achieve 50% inhibition of said target. Said values show a considerable inhibitory potency of thiazole compounds with regard to PI3Kγ.

Examples of inhibitory activities for compounds of the invention are set out in Table I below.

TABLE I

IC$_{50}$ values of thiazole derivatives against PI3Kγ

| Example No | PI3Kγ<br>IC$_{50}$ (μM) |
|---|---|
| 1 | 0.870 |
| 4 | 0.494 |
| 6 | 0.355 |
| 8 | 0.186 |
| 9 | 0.601 |
| 10 | 2.201 |
| 13 | 0.013 |
| 23 | 0.328 |
| 25 | 1.54 |
| 36 | 0.795 |
| 54 | 1.420 | b) Cell Based ELISA to Monitor PI3K Inhibition:

The efficacy of compounds of the invention in inhibiting the PI3K induced Akt/PKB phosphorylation may be tested in the following cell based assay.

Measurement of Akt/PKB phosphorylation in macrophages after stimulation with Complement 5a: Raw 264: Raw 264-7 macrophages (cultured in DMEM-F12 medium containing 10% Fetal Calf serum and antibiotics) are plated at 20'000 cells/well in a 96 MTP 24 h before cell stimulation. Prior to the stimulation with 50 nM of Complement 5a during 5 minutes, Cells are serum starved for 2 h, and pretreated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% $H_2O_2$ and 0.1% Sodium Azide in PBS/Triton and washed 3 times in PBS/Triton. Cells are then blocked by 60 minutes incubation with 10% fetal calf serum in PBS/Triton. Next, phosphorylated Akt/PKB is detected by an overnight incubation at 4° C. with primary antibody (anti phospho Serine 473 Akt IHC, Cell Signaling) diluted 800-fold in PBS/Triton, containing 5% bovine serum albumin (BSA). After 3 washes in PBS/Triton, cells are incubated for 60 minutes with a peroxidase conjugated goat-anti-rabbit secondary antibody (¹/₄₀₀ dilution in PBS/Triton, containing 5% BSA), washed 3 times in PBS/Triton, and 2 times in PBS and further incubated in 100 μl of luminescent substrate reagent solution (Pierce) for 2 minutes, followed by the reading (1 s/well).

The values indicated in Table II below reflect the percentage of inhibition of AKT phosphorylation as compared to basal level. Said values show a clear effect of the thiazole compounds on the activation of AKT phosphorylation in macrophages.

Examples of inhibitory activities for compounds of the invention are set out in Table II below.

TABLE II

IC$_{50}$ values of thiazole derivatives in Cell Assay

| Example No | Cell Assay (P-Akt, Elisa)<br>IC$_{50}$ [nM] |
|---|---|
| 2 | 710 |
| 8 | 910 |

EXAMPLE 57

Thioglycollate-induced Peritoneal Cavity Cell Recruitment Model

The in vivo efficacy of compounds of the invention in inhibiting the migration of leukocytes upon intraperitoneal challenge of thioglycollate may be tested with the following assay.

Experimental Protocol:

8-10 weeks old female C3H mice are fasted during 18 hours. 15 minutes prior the intraperitoneal injection of thioglycollate (1.5%, 40 ml/kg), the mice are treated orally with Thiazoles of Formula (I). Control mice receive CMC/Tween as vehicle (10 ml/kg). The mice are then sacrificed by $CO_2$ inhalation and the peritoneal cavity is washed two times with 5 ml of ice-cold PBS/1 mM EDTA. The ravages are done 4 h. or 48 h. after thioglycollate challenge to evaluate neutrophils or macrophages recruitment, respectively. The white blood cells (neutrophils, lymphocytes or macrophages) are counted using a Beckman Coulter® A$^c$T 5diff™. Dexamethasone is used as reference drug.

EXAMPLE 58

Preparation of a Pharmaceutical Formulation

Formulation 1—Tablets

A compound of Formula (I) is admixed as a dry powder with a dry gelatin binder in an approximate 1:2 weight ration. A minor amount of magnesium stearate is added as a lubricant. The mixture is formed into 240-270 mg tablets (80-90 mg) of active thiazole compound per tablet in a tablet press.

Formulation 2—Capsules

A compound of Formula (I) is admixed as a dry powder with a starch diluent in an approximate 1:1 weight ratio. The mixture is filled into 250 mg capsules (125 mg of active thiazole compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active thiazole compound) in a tablet press.

Formulation 5—Injection

A compound of Formula (I) is dissolved in a buffered sterile saline injectable aqueous medium to a concentration of approximately 5 mg/ml.

The invention claimed is:

1. A thiazole derivative according to Formula (I),

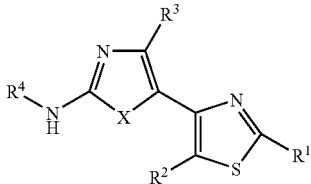

wherein $R^1$ is selected from —C(O)$R^5$, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl;

$R^2$ is selected from H, halogen, $C_1$-$C_6$-alkyl, $C_2$-$C_6$-alkenyl or $C_2$-$C_6$-alkynyl;

$R^3$ is selected from H, halogen, $C_1$-$C_6$-alkyl, $C_2$-$C_6$-alkenyl or $C_2$-$C_6$-alkynyl;

$R^4$ is selected from —C(O)$R^6$, aryl, heteroaryl, heterocycloalkyl or $C_3$-$C_8$ cycloalkyl;

$R^5$ is selected from H, hydroxyl, alkoxy, amino, aryl, heteroaryl, $C_3$-$C_8$ cycloalkyl or heterocycloalkyl;

$R^6$ is selected from H, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl or amino; and X is S;

and isomers, enantiomers, diastereomers, racemates or pharmaceutically acceptable salts thereof.

2. The thiazole derivative according to claim 1, wherein $R^1$ is —C(O)$R^5$.

3. The thiazole derivative according to claim 1, wherein $R^1$ is selected from $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl.

4. The thiazole derivative according to claim 1, wherein $R^2$ is H.

5. The thiazole derivative according to claim 1, wherein $R^3$ is methyl.

6. The thiazole derivative according to claim 1, wherein $R^4$ is selected from aryl, heterocycloalkyl or $C_3$-$C_8$ cycloalkyl.

7. The thiazole derivative according to claim 1, wherein $R^4$ is —C(O)$R^6$.

8. The thiazole derivative according to claim 1, wherein $R^5$ is selected from hydroxyl or alkoxy.

9. The thiazole derivative according to claim 1, wherein $R^5$ is amino.

10. The thiazole derivative according to claim 1, wherein $R^5$ is selected from aryl, heteroaryl, $C_3$-$C_8$ cycloalkyl or heterocycloalkyl.

11. The thiazole derivative according to claim 1, wherein $R^6$ is selected from $C_1$-$C_6$-alkyl, $C_2$-$C_6$-alkenyl, $C_2$-$C_6$-alkynyl, aryl $C_1$-$C_6$-alkyl or $C_1$-$C_6$-alkyl.

12. The thiazole derivative according to claim 1, wherein $R^6$ is optionally substituted amino.

13. The thiazole derivative according to claim 1, wherein X is S.

14. The thiazole derivative according to claim 1, wherein $R^1$ is —C(O)$R^5$, $R^2$ is H and $R^3$ is methyl.

15. The thiazole derivative according to claim 1, wherein $R^1$ is selected from $C_1$-$C_6$-alkyl, $C_2$-$C_6$-alkenyl, $C_2$-$C_6$-alkynyl, aryl $C_1$-$C_6$-alkyl or heteroaryl $C_1$-$C_6$-alkyl;

$R^2$ is H and $R^3$ is methyl.

16. The thiazole derivative according to claim 1, said thiazole derivative being selected from the following group:

Ethyl 2'-(acetylamino)-4'-methyl-4,5'-bi-1,3-thiazole-2-carboxylate;
2'-(acetylamino)-N-allyl-4'-methyl-4,5'-bi-1,3-thiazole-2-carboxamide;
N-[2-(cyanomethyl)-4'-methyl-4,5'-bi-1,3-thiazol-2'-yl]acetamide;
2'-(acetylamino)-4'-methyl-4,5'-bi-1,3-thiazole-2-carboxylic acid;
2'-(acetylamino)-N-(2-methoxyethyl)-4'-methyl-4,5'-bi-1,3-thiazole-2-carboxamide;
2'-(acetylamino)-4'-methyl-N-(tetrahydrofuran-2-ylmethyl)-4,5'-bi-1,3-thiazole-2-carboxamide;
2'-(acetylamino)-N-[2-(dimethylamino)ethyl]-4'-methyl-4,5'-bi-1,3-thiazole-2-carboxamide;
N-[4'-methyl-2-(morpholin-4-ylcarbonyl)-4,5'-bi-1,3-thiazol-2'-yl]acetamide;
N-{4'-methyl-2-[(4-methylpiperazin-1-yl)carbonyl]-4,5'-bi-1,3-thiazol-2'-yl}acetamide;
2'-(acetylamino)-N-[3-(dimethylamino)propyl]-4'-methyl-4,5'-bi-1,3-thiazole-2-carboxamide;
2'-(acetylamino)-N-(2-hydroxyethyl)-4'-methyl-4,5-bi-1,3-thiazole-2-carboxamide;
2'-(acetylamino)-N-(2-cyanoethyl)-4'-methyl-4,5'-bi-1,3-thiazole-2-carboxamide;
2'-(acetylamino)-4'-methyl-N-1H-tetrazol-5-yl-4,5'-bi-1,3-thiazole-2-carboxamide:
4-({[2'-(acetylamino)-4'-methyl-4,5'-bi-1,3-thiazol-2-yl]carbonyl}amino)benzoic acid;
3-({[2'-(acetylamino)-4'-methyl-4,5'-bi-1,3-thiazol-2-yl]carbonyl}amino)benzoic acid;
2'-(acetylamino)-4'-methyl-N-[3-(1H-tetrazol-5-yl)phenyl]-4,5'-bi-1,3-thiazole-2-carboxamide;
2'-(acetylamino)-N-benzyl-4'-methyl-4,5'-bi-1,3-thiazole-2-carboxamide;
2'-(acetylamino)-4'-methyl-N-propyl-4,5'-bi-1,3-thiazole-2-carboxamide;
2'-(acetylamino)-4'-methyl-N-[4-(1H-tetrazol-5-yl)phenyl]-4,5'-bi-1,3-thiazole-2-carboxamide;
3-({[2'-(acetylamino)-4'-methyl-4,5'-bi-1,3-thiazol-2-yl]carbonyl}amino)-2-hydroxy benzoic acid;
1-{[2'-(acetylamino)-4'-methyl-4,5'-bi-1,3-thiazol-2-yl]carbonyl}piperidine-3-carboxylic acid;
5-({[2'-(acetylamino)-4'-methyl-4,5'-bi-1,3-thiazol-2-yl]carbonyl}amino)-2-hydroxy benzoic acid;
N-[4'-methyl-2-(2H-tetrazol-5-ylmethyl)-4,5'-bi-1,3-thiazol-2'-yl]acetamide;
1-{[2'-(acetylamino)-4'-methyl-4,5'-bi-1,3-thiazol-2-yl]carbonyl}piperidine-4-carboxylic acid;
2'-(acetylamino)-N-[3-(5-amino-1,3,4-thiadiazol-2-yl)phenyl]-4'-methyl-4,5'-bi-1,3-thiazole-2-carboxamide;
N-{2-[(3-hydroxypiperidin-1-yl)carbonyl]-4'-methyl-4,5'-bi-1,3-thiazol-2'-yl}acetamide;
N-(2-{[4-(hydroxymethyl)piperidin-1-yl]carbonyl}-4'-methyl-4,5'-bi-1,3-thiazol-2'-yl)acetamide;
N-(2-{[4-(2-hydroxyethyl)piperidin-1-yl]carbonyl}-4'-methyl-4,5'-bi-1,3-thiazol-2'-yl)acetamide;
N-{2-[(4-hydroxypiperidin-1-yl)carbonyl]-4'-methyl-4,5'-bi-1,3-thiazol-2'-yl}acetamide;
2'-(acetylamino)-N-1H-1,2,3-benzotriazol-5-yl-4'-methyl-4,5'-bi-1,3-thiazole-2-carboxamide;
4-({[2'-(acetylamino)-4'-methyl-4,5'-bi-1,3-thiazol-2-yl]carbonyl}amino)-2-hydroxy benzoic acid;
4-({[2'-(acetylamino)-4'-methyl-4,5'-bi-1,3-thiazol-2-yl]carbonyl}amino)-2-fluoro benzoic acid;

2'-(acetylamino)-N-[3-(5-hydroxy-1,3,4-oxadiazol-2-yl)
  phenyl]-4'-methyl-4,5'-bi-1,3-thiazole-2-carboxamide;
2'-(acetylamino)-N-[4-(5-hydroxy-1,3,4-oxadiazol-2-yl)
  phenyl]-4'-methyl-4,5'-bi-1,3-thiazole-2-carboxamide;
N-[2-(hydroxymethyl)-4'-methyl-4,5'-bi-1,3-thiazol-2'-
  yl]acetamide;
N-(2-methoxyethyl)-N'-[4'-methyl-2-(morpholin-4-ylcar-
  bonyl)-4,5'-bi-1,3-thiazol-2'-yl]urea;
Ethyl N-({[4'-methyl-2-(morpholin-4-ylcarbonyl)-4,5'-bi-
  1,3-thiazol-2'-yl]amino}carbonyl)-beta-alaninate;
N-[2-(1,4-dioxa-8-azaspiro[4.5]dec-8-ylcarbonyl)-4'-me-
  thyl-4,5'-bi-1,3-thiazol-2'-yl]acetamide;
2'-(acetylamino)-N-(2,3-dihydroxypropyl)-4'-methyl-4,
  5'-bi-1,3-thiazole-2-carboxamide;
N-[4'-methyl-2-(morpholin-4-ylcarbonyl)-4,5'-bi-1,3-
  thiazol-2'-yl]urea;
N-{4'-methyl-2-[(3-oxopiperazin-1-yl)carbonyl]-4,5'-bi-
  1,3-thiazol-2'-yl}acetamide;
N-{4'-methyl-2-[(4-oxopiperidin-1-yl)carbonyl]-4,5'-bi-
  1,3-thiazol-2'-yl}acetamide;
N-{2-[(3-hydroxypyrrolidin-1-yl)carbonyl]-4'-methyl-4,
  5'-bi-1,3-thiazol-2'-yl}acetamide;
2'-(acetylamino)-4'-methyl-N-prop-2-yn-1-yl-4,5'-bi-1,3-
  thiazole-2-carboxamide;
N-{2-[(4-acetylpiperazin-1-yl)carbonyl]-4'-methyl-4,5'-
  bi-1,3-thiazol-2'-yl}acetamide;
N~1~,N~1~-dimethyl-N~2~-({[4'-methyl-2-(morpholin-
  4-ylcarbonyl)-4,5'-bi-1,3-thiazol-2'-yl]
  amino}carbonyl)glycinamide;
N-({[4'-methyl-2-(morpholin-4-ylcarbonyl)-4,5'-bi-1,3-
  thiazol-2'-yl]amino}carbonyl)-beta-alanine;
N-{2-[(4-fluoropiperidin-1-yl)carbonyl]-4'-methyl-4,5'-
  bi-1,3-thiazol-2'-yl}acetamide;
N-(2-{[(1S,5S,7S)-7-(hydroxymethyl)-6,8-dioxa-3-
  azabicyclo[3.2.1]oct-3-yl]carbonyl}-4'-methyl-4,5'-bi-
  1,3-thiazol-2'-yl)acetamide;
Ethyl N-({[2-(cyanomethyl)-4'-methyl-4,5'-bi-1,3-thia-
  zol-2'-yl]amino}carbonyl)-beta-alaninate;
N-(2-{[(1R,5R,7R)-7-(hydroxymethyl)-6,8-dioxa-3-
  azabicyclo[3.2.1]oct-3-yl]carbonyl}-4'-methyl-4,5'-bi-
  1,3-thiazol-2'-yl)acetamide;
Tert-butyl N-({[2-(cyanomethyl)-4'-methyl-4,5'-bi-1,3-
  thiazol-2'-yl]amino}carbonyl)-beta-alaninate;
[4'-methyl-2'-(pyrazin-2-ylamino)-4,5'-bi-1,3-thiazol-2-
  yl]acetonitrile;
Ethyl 4'-methyl-2'-(pyrazin-2-ylamino)-4,5'-bi-1,3-thiaz-
  ole-2-carboxylate;
[4'-methyl-2'-(1H-pyrazol-3-ylamino)-4,5'-bi-1,3-thiazol-
  2-yl]acetonitrile;
N-[4'-methyl-2-(2-morpholin-4-yl-2-oxoethyl)-4,5'-bi-1,
  3-thiazol-2'-yl]acetamide;
2-[2'-(acetylamino)-4'-methyl-4,5'-bi-1,3-thiazol-2-yl]ac-
  etamide;
tert-butyl 4-{[2-(cyanomethyl)-4'-methyl-4,5'-bi-1,3-thia-
  zol-2'-yl]amino}-4-oxobutanoate;
methyl 5-{[2-(cyanomethyl)-4'-methyl-4,5'-bi-1,3-thia-
  zol-2'-yl]amino}-5-oxopentanoate;
methyl 6-{[2-(cyanomethyl)-4'-methyl-4,5'-bi-1,3-thia-
  zol-2'-yl]amino}-6-oxohexanoate;
2'-(acetylamino)-N,N,4'-trimethyl-4,5'-bi-1,3-thiazole-2-
  carboxamide;
2'-(acetylamino)-4'-methyl-4,5'-bi-1,3-thiazole-2-car-
  boxamide;
4-{[2-(cyanomethyl)-4'-methyl-4,5'-bi-1,3-thiazol-2'-yl]
  amino}-4-oxobutanoic acid;
5-{[2-(cyanomethyl)-4'-methyl-4,5'-bi-1,3-thiazol-2'-yl]
  amino}-5-oxopentanoic acid;
tert-butyl N-({[2-(cyanomethyl)-4'-methyl-4,5'-bi-1,3-
  thiazol-2'-yl]amino}carbonyl)glycinate;
tert-butyl 4-[({[2-(cyanomethyl)-4'-methyl-4,5'-bi-1,3-
  thiazol-2'-yl]amino}carbonyl)amino]butanoate;
N~2~-({[2-(cyanomethyl)-4'-methyl-4,5'-bi-1,3-thiazol-
  2'-yl]amino}carbonyl)-N~1~,N~1~-dimethylglycina-
  mide;
tert-butyl N-({[4'-methyl-2-(morpholin-4-ylcarbonyl)-4,
  5'-bi-1,3-thiazol-2'-yl]amino}carbonyl)-beta-alaninate;
N-[4'-methyl-2-(morpholin-4-ylcarbonyl)-4,5'-bi-1,3-
  thiazol-2'-yl]-N-(2-morpholin-4-yl-2-oxoethyl)urea;
N-[2-(cyanomethyl)-4'-methyl-4,5'-bi-1,3-thiazol-2'-yl]-
  N-(2-morpholin-4-yl-2-oxoethyl)urea;
methyl N-({[2-(cyanomethyl)-4'-methyl-4,5'-bi-1,3-thia-
  zol-2'-yl]amino}carbonyl)-beta-alaninate;
N~3~-({[2-(cyanomethyl)-4'-methyl-4,5'-bi-1,3-thiazol-
  2'-yl]amino}carbonyl)-N~1~,N~1~-diisopropyl-beta-
  alaninamide;
N~3~-({[2-(cyanomethyl)-4'-methyl-4,5'-bi-1,3-thiazol-
  2'-yl]amino}carbonyl)-N~1~-(2-hydroxy-1,1-dimeth-
  ylethyl)-beta-alaninamide;
N~1~-(tert-butyl)-N~3~-({[2-(cyanomethyl)-4'-methyl-4,
  5'-bi-1,3-thiazol-2'-yl]amino}carbonyl)-beta-alanina-
  mide;
N-[2-(cyanomethyl)-4'-methyl-4,5'-bi-1,3-thiazol-2'-yl]-
  N-[3-(2,2-dimethyl-1,3-thiazolidin-3-yl)-3-oxopropyl]
  urea;
N-[2-(cyanomethyl)-4'-methyl-4,5'-bi-1,3-thiazol-2'-yl]-
  N-[3-(4,4-dimethyl-1,3-oxazolidin-3-yl)-3-oxopropyl]
  urea;
N~2~-({[2-(cyanomethyl)-4'-methyl-4,5'-bi-1,3-thiazol-
  2'-yl]amino}carbonyl)-N~1~-(2,2-dimethylpropyl)gly-
  cinamide;
N-(3-azocan-1-yl-3-oxopropyl)-N-[2-(cyanomethyl)-4'-
  methyl-4,5'-bi-1,3-thiazol-2'-yl]urea;
N-[2-(cyanomethyl)-4'-methyl-4,5'-bi-1,3-thiazol-2'-yl]-
  N'-[2-(1-isopropyl-1H-imidazol-4-yl)ethyl]urea;
N-[2-(cyanomethyl)-4'-methyl-4,5'-bi-1,3-thiazol-2'-yl]-
  N'-[2-(1-ethyl-1H-imidazol-4-ypethyl]urea;
N-[2-(5-tert-butyl-1,2,4-oxadiazol-3-yl)ethyl]-N'-[2-
  (cyanomethyl)-4'-methyl-4,5'-bi-1,3-thiazol-2'-yl]urea;
N-[2-(cyanomethyl)-4'-methyl-4,5'-bi-1,3-thiazol-2-yl]-
  N'[2-(5-isopropyl-1,2,4-oxadiazol-3-yl)ethyl]urea; or
N-(4'-methyl-2-{[5-(1-methylpiperidin-4-yl)-1,2,4-oxa-
  diazol-3-yl]methyl}-4,5'-bi-1,3-thiazol-2'-yl)aceta-
  mide.

17. A thiazole derivative according to Formula (Ia)

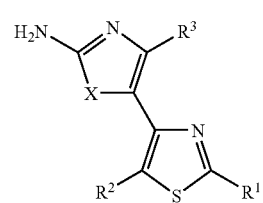

Ia wherein $R^1$ is selected from —C(O)$R^5$, $C_1$-$C_6$-alkyl,
  $C_2$-$C_6$-alkenyl, $C_2$-$C_6$-alkynyl, aryl $C_1$-$C_6$-alkyl, het-
  eroaryl $C_1$-$C_6$-alkyl, $C_3$-$C_8$ cycloalkyl $C_1$-$C_6$-alkyl or
  heterocycloalkyl $C_1$-$C_6$-alkyl;
$R^2$ is selected from H, halogen, $C_1$-$C_6$-alkyl, $C_2$-$C_6$-alkenyl
  or $C_2$-$C_6$-alkynyl;
$R^3$ is selected from H, halogen, $C_1$-$C_6$-alkyl, $C_2$-$C_6$-alkenyl
  or $C_2$-$C_6$-alkynyl;

$R^5$ is selected from H, hydroxyl, alkoxy, amino, aryl, heteroaryl, $C_3$-$C_8$ cycloalkyl or heterocycloalkyl;

X is S;

and isomers, enantiomers, diastereomers, racemates or pharmaceutically acceptable salts thereof, with the proviso that the compounds of formula Ia are not the following compounds:

[4,5'-bithiazole]-2-acetonitrile, 2'-amino-4'-methyl;

2'-amino-4'-methyl-(phenylhydrazono)-[4,5'-bithiazole]-2-acetonitrile;

2'-amino-[(4-chlorophenyl)hydrazono]-4'-methyl-[4,5'-bithiazole]-2-acetonitrile; or

[4,5'-bithiazole]-4'-carboxylic acid, 2'-amino-2-methyl-, ethyl ester.

18. The thiazole derivative according to claim 17, wherein $R^1$ is —C(O)$R^5$.

19. The thiazole derivative according to claim 17, wherein $R^1$ is selected from $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl, $C_1$-$C_6$-alkyl or heterocycloalkyl $C_1$-$C_6$-alkyl.

20. The thiazole derivative according to claim 17, wherein $R^2$ is H.

21. The thiazole derivative according to claim 17, wherein $R^3$ is methyl.

22. A method of treating autoimmune disorders, inflammatory diseases, cardiovascular diseases, neurodegenerative diseases, bacterial or viral infections, kidney diseases, platelet aggregation, transplantation, erythrocyte deficiency, graft rejection or lung injuries comprising the administration of a pharmaceutically effective amount of a compound of Formula I,

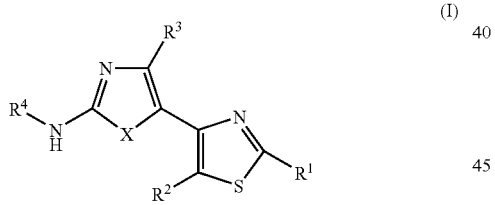

(I)

wherein $R^1$ is selected from —C(O)$R^5$, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$ alkyl;

$R^2$ is selected from H, halogen, $C_1$-$C_6$-alkyl, $C_2$-$C_6$-alkenyl or $C_2$-$C_6$-alkynyl;

$R^3$ is selected from H, halogen, $C_1$-$C_6$-alkyl, $C_2$-$C_6$-alkenyl or $C_2$-$C_6$-alkynyl;

$R^4$ is selected from —C(O)$R^6$, aryl, heteroaryl, heterocloalkyl or $C_3$-$C_8$ cycloalkyl;

$R^5$ is selected from H, hydroxyl, alkoxy, amino, aryl, heteroaryl, $C_3$-$C_8$ cycloalkyl or heterocycloalkyl;

$R^6$ selected from H, $C_1$-$C_6$-alkenyl, $C_2$-$C_6$-alkynyl, aryl $C_1$-$C_6$-alkyl, heteroaryl $C_1$-$C_6$-alkyl or amino; and X is S;

and isomers, enantiomers, diastereomers, racemates or pharmaceutically acceptable salts thereof or Formula Ia,

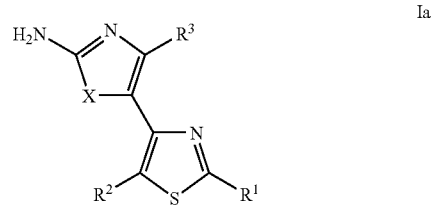

Ia wherein $R^1$ is selected from —C(O)$R^5$, $C_1$-$C_6$-alkyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl;

$R^2$ is selected from H, halogen, $C_1$-$C_6$-alkyl, $C_2$-$C_6$-alkenyl or $C_2$-$C_6$-alkynyl;

$R^3$ is selected from H, halogen, $C_1$-$C_6$-alkyl, $C_2$-$C_6$-alkenyl or $C_2$-$C_6$-alkynyl;

$R^5$ is selected from H, hydroxyl, alkoxy, amino, aryl, heteroaryl, $C_3$-$C_8$ cycloalkyl or heterocycloalkyl;

X is S;

and isomers, enantiomers, diastereomers, racemates or pharmaceutically acceptable salts thereof, with the proviso that the compounds of formula Ia are not the following compounds:

[4,5'-bithiazole]-2-acetonitrile, 2'-amino-4'-methyl;

2'-amino-4'-methyl-(phenylhydrazono)-[4,5'-bithiazolel]-2-acetonitrile;

2'amino-[(4-chlorophenyl)hydrazonol]-4'-methyl-[4,5'-bithiazole]-2-acetonitrile; or

[4,5'-bithiazole]-4'-carboxylic acid, 2'-amino-2-methyl-, ethyl ester to an individual in need of treatment, wherein said autoimmune disorders, inflammatory diseases, cardiovascular diseases, neurodegenerative diseases, bacterial or viral infections, kidney diseases, platelet aggregation, transplantation, erythrocyte deficiency, graft rejection or lung injuries are selected from multiple sclerosis, psoriasis, rheumatoid arthritis, systemic lupus erythematosis, inflammatory bowel disease, lung inflammation, thrombosis, brain inflammation, Alzheimer's disease, Huntington's disease, CNS trauma, stroke, ischemic conditions, atherosclerosis, heart hypertrophy, cardiac myocyte dysfunction, elevated blood pressure, vasoconstriction, chronic obstructive pulmonary disease, anaphylactic shock fibrosis, psoriasis, allergic diseases, asthma, stroke, ischemic conditions, ischemia-reperfusion, platelet aggregation/activation skeletal muscle atrophy/hypertrophy, acute and chronic bacterial and viral infections, sepsis, graft rejection, glomerulo sclerosis, glomerulo nephritis, progressive renal fibrosis, endothelial and epithelial injuries in the lung, or general lung airway inflammation.

23. The method according to claim 22, wherein said autoimmune disorders or inflammatory diseases are selected from multiple sclerosis, psoriasis, rheumatoid arthritis, systemic lupus erythematosis, inflammatory bowel disease, lung inflammation, thrombosis or brain inflammation.

24. The method according to claim 22, wherein said neurodegenerative diseases are selected from Alzheimer's disease, Huntington's disease, CNS trauma, stroke or ischemic conditions.

25. The method according to claim 22, wherein said cardiovascular diseases are selected from atherosclerosis, heart hypertrophy, cardiac myocyte dysfunction, elevated blood pressure or vasoconstriction.

26. The method according to claim 22, wherein said autoimmune disorders, inflammatory diseases, cardiovascular diseases, neurodegenerative diseases, bacterial or viral infections, kidney diseases, platelet aggregation, transplantation, erythrocyte deficiency, graft rejection or lung injuries are selected from chronic obstructive pulmonary disease, anaphylactic shock, fibrosis, psoriasis, allergic diseases, asthma, stroke or ischemic conditions, ischemia-reperfusion, platelet aggregation/activation, skeletal muscle atrophy/hypertrophy, acute and chronic bacterial and viral infections, sepsis, graft rejection, glomerulo sclerosis, glomerulo nephritis, progressive renal fibrosis, endothelial and epithelial injuries in the lung, or general lung airway inflammation.

27. A pharmaceutical composition comprising at least one thiazole derivative of Formula I,

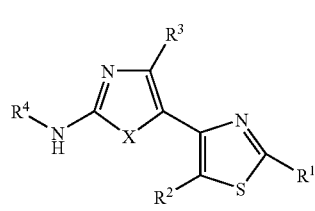

(I)

wherein $R^1$ is selected from —C(O)$R^5$, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl;

$R^2$ is selected from H, halogen, $C_1$-$C_6$-alkyl, $C_2$-$C_6$-alkenyl or $C_2$-$C_6$-alkynyl:

$R^3$ is selected from H, halogen, $C_1$-$C_6$-alkyl, $C_2$-$C_6$-alkenyl or $C_2$-$C_6$-alkynyl;

$R^4$ is selected from —C(O)$R^6$, aryl, heteroaryl, heterocycloalkyl or $C_3$-$C_8$ cycloalkyl;

$R^5$ is selected from H, hydroxyl, alkoxy, amino, aryl, heteroaryl, $C_3$-$C_8$ cycloalkyl or heterocycloalkyl;

$R^6$ selected from H, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl or amino; and X is S;

and isomers, enantiomers, diastereomers, racemates or pharmaceutically acceptable salts thereof, or Formula Ia,

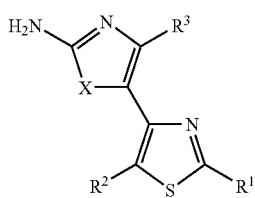

Ia wherein $R^1$ is selected from —C(O)$R^5$, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl;

$R^2$ is selected from H, halogen, $C_1$-$C_6$-alkyl, $C_2$-$C_6$-alkenyl or $C_2$-$C_6$-alkynyl;

$R^3$ is selected from H, halogen, $C_1$-$C_6$-alkyl, $C_2$-$C_6$-alkenyl or $C_2$-$C_6$-alkynyl;

$R^5$ is selected from H, hydroxyl, alkoxy, amino, aryl, heteroaryl, $C_3$-$C_8$ cycloalkyl or heterocycloalkyl;

X is S;

and isomers, enantiomers, diastereomers, racemates or pharmaceutically acceptable salts thereof, with the proviso that the compounds of formula Ia are not the following compounds:

[4,5'-bithiazole]-2-acetonitrile, 2'-amino-4'-methyl;

2'-amino-4'-methyl-(phenylhydrazono)-[4,5'-bithiazole]-2-acetonitrile;

2'-[(4-chlorophenyl)hydrazono]-4'-methyl-[4,5'-bithiazole]-2-acetonitrile; or

[4,5'-bithiazole]-4'-carboxylic acid, 2'-amino-2-methyl-, ethyl ester, and a pharmaceutically acceptable carrier, diluent or excipient thereof.

28. A method of treating cancer comprising the administration of a pharmaceutically effective amount of a compound of Formula I, (I)

wherein $R^1$ is selected from —C(O)$R^5$, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl;

$R^2$ is selected from H, halogen, $C_1$-$C_6$-alkyl, $C_2$-$C_6$-alkenyl or $C_2$-$C_6$-alkynyl;

$R^3$ is selected from H, halogen, $C_1$-$C_6$-alkyl, $C_2$-$C_6$-alkenyl or $C_2$-$C_6$-alkynyl;

$R^4$ is selected from —C(O)$R^6$, aryl, heteroaryl, heterocycloalkyl or $C_3$-$C_8$ cycloalkyl;

$R^5$ is selected from H, hydroxyl, alkoxy, amino, aryl, heteroaryl, $C_3$-$C_8$ cycloalkyl or heterocycloalkyl;

$R^6$ selected from H, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl or amino; and X is S;

and isomers, enantiomers, diastereomers, racemates or pharmaceutically acceptable salts thereof or Formula Ia,

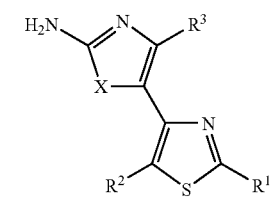

Ia wherein $R^1$ is selected from —C(O)$R^5$, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, $C_3$-$C_8$ cycloalkyl $C_1$-$C_6$-alkyl or heterocycloalkyl $C_1$-$C_6$-alkyl;

$R^2$ is selected from H, halogen, $C_1$-$C_6$-alkyl, $C_2$-$C_6$-alkenyl or $C_2$-$C_6$-alkynyl;

R³ is selected from H, halogen, C₁-C₆-alkyl, C₂-C₆-alkenyl or C₂-C₆-alkynyl;

R⁵ is selected from H, hydroxyl, alkoxy, amino, aryl, heteroaryl, C₃-C₈ cycloalkyl or heterocycloalkyl;

X is S;

and isomers, enantiomers, diastereomers, racemates or pharmaceutically acceptable salts thereof, with the proviso that the compounds of formula la are not the following compounds:

[4,5'-bithiazole]-2-acetonitrile, 2'-amino-4'-methyl;

2'-amino-4'-methyl-(phenylhydrazono)-[4,5'-bithiazole]-2-acetonitrile;

2'-amino-[(4-chlorophenyl)hydrazono]-4'-methyl-[4,5'-bithiazole]-2-acetonitrile; or

[4,5'-bithiazole]-4'-carboxylic acid, 2'-amino-2-methyl-, ethyl ester, wherein said cancer is selected from invasion metastasis, melanoma, or Kaposi's sarcoma.

* * * * *

UNITED STATES PATENT AND TRADEMARK OFFICE
CERTIFICATE OF CORRECTION

PATENT NO. : 7,799,814 B2
APPLICATION NO. : 11/915476
DATED : September 21, 2010
INVENTOR(S) : Anna Quattropani et al.

It is certified that error appears in the above-identified patent and that said Letters Patent is hereby corrected as shown below:

Column 2,
Line 15, "(Vanhaesebraeck" should read --(Vanhaesebroeck--.

Column 4,
Line 38, "it can longer" should read --it can no longer--.

Column 7,
Line 48, "one a compound" should read --one compound--.

Column 12,
Line 22, "like "Pharmaceutically" should read
    --like.
        Pharmaceutically--.

Column 24,
Lines 24-25, "pathways for the will be described" should read
    --pathways will be described--.

Column 28,
Line 62, "person skills in" should read --person skilled in--.

Column 38,
Line 44, "$R_f 0.4$." should read --$R_f=0.4$.--.

Column 39,
Line 41, "N-[2-cyanomethyl)-4'" should read --N-[2-(cyanomethyl)-4'--.

Column 40,
Line 48, "reduce pressure" should read --reduced pressure--.

Signed and Sealed this
Fifteenth Day of March, 2011

David J. Kappos
*Director of the United States Patent and Trademark Office*

Column 44,
Line 20, "and rinced" should read --and rinsed--.

Column 45,
Line 65, "describe above" should read --described above--.

Column 46,
Line 46, "describe above" should read --described above--.

Column 48,
Line 48, "describe above" should read --described above--.

Column 51,
Line 43, "describe above" should read --described above--.
Line 45, "two equals" should read --two equal--.

Column 57,
Line 40, "N-[4'-methyl-2-(morpholin-4-ylcarbonyl)-4,5-bi-1,3-thiazol-2'-yl] acetamide" should read
--N-[4'-methyl-2-(morpholin-4-ylcarbonyl)-4,5'-bi-1,3-thiazol-2'-yl] acetamide--.

Column 64,
Line 5, "product is in" should read --product is crystallyzed in--.

Column 65,
Line 1, "Step I: 2mL(acetylamino)" should read --Step I: 2'-(acetylamino)--.

Column 72,
Line 60, "(3211" should read --(321 μl--.

Column 74,
Line 22, "(511" should read --(51 μl--.
Line 50, "5-bi" should read --5'-bi--.

Column 78,
Line 3, "2-vn-1" should read --2-yn-1--.
Line 29, "C—CH)" should read --C≡CH)--.

Column 80,
Line 59, "according to literature" should read --according to the literature--.

Column 82,
Line 22, "according to literature" should read --according to the literature--.

Column 83,
Line 44, "rinsed -with" should read --rinsed with--.

Column 98,
Line 16, "4,5-bi" should read --4,5'-bi--.

Column 100,
Line 51, "MgCl mM" should read --MgCl 30mM--.

Column 102,
Line 20, "The ravages are" should read --The lavages are--.

Column 104,
Line 23, "4,5-bi-1" should read --4,5'-bi-1--.

Column 106,
Line 39, "ypethyl]urea" should read --yl)ethyl]urea--.
Line 42, "thiazol-2-yl]" should read --thiazol-2'-yl]--.

Column 107,
Line 65, "H, $C_1$-$C_6$-alkenyl" should read --H, $C_1$-$C_6$-alkyl, $C_2$-$C_6$-alkenyl--.

Column 108,
Lines 14-15, "$C_1$-$C_6$-alkyl, $C_2$-$C_6$-alkynyl" should read
--$C_1$-$C_6$-alkyl, $C_2$-$C_6$-alkenyl, $C_2$-$C_6$-alkynyl--.

Column 110,
Line 13, "2'-[(4" should read --2'-amino-[(4--.